United States Patent
Sabatini et al.

(10) Patent No.: US 10,126,303 B2
(45) Date of Patent: Nov. 13, 2018

(54) METHODS FOR IDENTIFYING COMPOUNDS AS MODULATORS OF SLC38A9 INTERACTIONS

(71) Applicant: Whitehead Institute for Biomedical Research, Cambridge, MA (US)

(72) Inventors: David M. Sabatini, Cambridge, MA (US); Shuyu Wang, Cambridge, MA (US); Zhi Tsun, Sunnyvale, CA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/308,605

(22) PCT Filed: May 1, 2015

(86) PCT No.: PCT/US2015/028885
§ 371 (c)(1),
(2) Date: Nov. 2, 2016

(87) PCT Pub. No.: WO2015/168617
PCT Pub. Date: Nov. 5, 2015

(65) Prior Publication Data
US 2017/0082633 A1 Mar. 23, 2017

Related U.S. Application Data

(60) Provisional application No. 61/987,769, filed on May 2, 2014, provisional application No. 62/095,512, filed on Dec. 22, 2014.

(51) Int. Cl.
*G01N 33/50* (2006.01)
*G01N 33/53* (2006.01)
*G01N 33/58* (2006.01)
*G01N 33/68* (2006.01)
*A61K 31/00* (2006.01)

(52) U.S. Cl.
CPC ............. *G01N 33/68* (2013.01); *A61K 31/00* (2013.01); *G01N 2333/4706* (2013.01); *G01N 2500/04* (2013.01)

(58) Field of Classification Search
None
See application file for complete search history.

(56) References Cited

U.S. PATENT DOCUMENTS

| 2014/0249045 A1 | 9/2014 | Kim et al. |
| 2017/0027897 A1 | 2/2017 | Sabatini et al. |
| 2017/0285043 A1 | 10/2017 | Sabatini et al. |

FOREIGN PATENT DOCUMENTS

| WO | WO 2013/043012 A2 | 3/2013 |
| WO | WO 2013/053919 A2 | 4/2013 |
| WO | WO 2014/153118 A1 | 9/2014 |
| WO | WO 2015/061607 A1 | 4/2015 |
| WO | WO 2015/168617 | 11/2015 |
| WO | WO2015/173398 | 11/2015 |
| WO | WO 2016/040824 | 3/2016 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Bar-Peled, Liron, and David M. Sabatini. "Regulation of mTORC1 by amino acids." *Trends in cell biology* 24.7 (2014): 400-406.
Wang, Shuyu, et al, "Lysosomal amino acid transporter SLC38A9 signals arginine sufficiency to mTORC1." *Science* 347.6218 (2015): 188-194.
Jewell, Jenna L., et al. "Differential regulation of mTORC1 by leucine and glutamine." Science 347.6218 (2015): 194-198.
Rebsamen, Manuele, et al. "SLC38A9 is a component of the lysosomal amino acid sensing machinery that controls mTORC1." Nature 519.7544 (2015): 477-481.
Sabatini, David M., Abstract "Cell Growth Signaling in Cancer Development," National Institutes of Health Grant No. R01 CA129105-01A1, funded on Apr. 8, 2008, through R01 CA129105-09, funded on Jan. 27, 2016.
Sabatini, David M., Abstract "Regulation of the MTOR Growth Pathway by Nutrients," National Institutes of Health Grant No. R01 CA103866-01, funded on Mar. 23, 2004, through R01 CA103866-13, funded on May 20, 2016.
Sabatini, David M., Abstract "Translational Control by Rapamycinsensitive Signaling," National Institutes of Health Grant No. R01 A1047389-01, funded on Apr. 1, 2000, through R37 A1047389-17, funded on Apr. 21, 2016.
International Search Report and Written Opinion issued in International Application No. PCT/US2015/028885, dated Nov. 2, 2015.
Maiese, Kenneth, et al. "mTOR: on target for novel therapeutic strategies in the nervous system." *Trends in molecular medicine* 19.1 (2013): 51-60.
Lamming, Dudley W., et al. "Rapalogs and rnTOR inhibitors as anti-aging therapeutics." *The Journal of clinical investigation* 123.3 (2013): 980-989.
Ben-Sahra, I., et al. "Sestrin2 integrates Akt and mTOR signaling to protect cells against energetic stress-induced death." *Cell Death & Differentiation*, Dec. 14, 2013, vol. 20, pp. 611-619.
Bar-Peled, Liron, et al. "A Tumor suppressor complex with GAP activity for the Rag GTPases that signal amino acid sufficiency to mTORC1." Science, May 31, 2013, vol. 340, No. 6136, pp. 1100-1106.

(Continued)

Primary Examiner — Joanne Hama
Assistant Examiner — Jon M Lockard
(74) Attorney, Agent, or Firm — Lisa M. Warren, Esq.; Morse, Barnes-Brown & Pendleton, P.C.

(57) ABSTRACT

The invention relates to methods of identifying compounds that modulate mTORC1 activity in a cell by modulating the activity of SLC38A9 (NCBI Gene ID: 153129), as well as to the use of such identified compounds in the modulation of mTORC1 and the treatment of diseases and conditions characterized by aberrant mTORC1 activity.

6 Claims, 35 Drawing Sheets

Specification includes a Sequence Listing.

(56) References Cited

OTHER PUBLICATIONS

Parkhitko, A. A., et al. "Kinase mTOR: regulation and role in maintenance of cellular homeostasis, tumor development, and aging." *Biochemistry (Moscow)*, Feb. 2014, vol. 79, No, 2, pp. 88-101.

Chantranupong, Lynne, et al. "The Sestrins interact with GATOR2 to negatively regulate the amino-acid-sensing pathway upstream of mTORC1." *Cell Reports*, Sep. 14, 2014, vol. 9, pp. 1-8.

Parmigiani, Anita, et al. "Sestrins inhibit mTORC1 kinase activation through the GATOR complex." *Cell Reports*, Oct. 19, 2014, vol. 9, pp. 1281-1291.

Kim, Jeong Sig, et al. "Sestrin2 inhibits mTORC1 through modulation of GATOR complexes." *Scientific Reports*, Mar. 30, 2015, vol. 5, pp. 1-10.

Kitada, Munehiro, et al., "Nutrient Sensing and Regulation of Cellular Functions," Kagaku to seibutsu (*Chemistry and Biology*), 2013, vol. 51, pp. 294-301.

Extended European Search Report in Application No. EP 15 78 6697 dated Aug. 9, 2017.

International Search Report and Written Opinion for International Application No. PCT/US2015/049727, dated Apr. 11, 2016.

Extended European Search Report in Application No. EP 15840013.4, dated Jan. 24, 2018.

Non-Final Office Action in U.S. Appl. No. 15/511,007 dated Dec. 21, 2017.

Notice of Allowance and Fee(s) Due in U.S. Appl. No. 15/511,007, dated Aug. 8, 2018.

\* cited by examiner

SEQUENCE LISTING

<160> NUMBER OF SEQ ID NOS: 12

<210> SEQ ID NO 1
<211> LENGTH: 561
<212> TYPE: PRT
<213> ORGANISM: Homo sapiens

<400> SEQUENCE: 1

Met Ala Asn Met Asn Ser Asp Ser Arg His Leu Gly Thr Ser Glu Val
1               5                   10                  15

```
Asp His Glu Arg Asp Pro Gly Pro Met Asn Ile Gln Phe Glu Pro Ser
             20                  25                  30

Asp Leu Arg Ser Lys Arg Pro Phe Cys Ile Glu Pro Thr Asn Ile Val
         35                  40                  45

Asn Val Asn His Val Ile Gln Arg Val Ser Asp His Ala Ser Ala Met
     50                  55                  60

Asn Lys Arg Ile His Tyr Tyr Ser Arg Leu Thr Thr Pro Ala Asp Lys
 65                  70                  75                  80

Ala Leu Ile Ala Pro Asp His Val Val Pro Ala Pro Glu Glu Cys Tyr
                 85                  90                  95

Val Tyr Ser Pro Leu Gly Ser Ala Tyr Lys Leu Gln Ser Tyr Thr Glu
            100                 105                 110

Gly Tyr Gly Lys Asn Thr Ser Leu Val Thr Ile Phe Met Ile Trp Asn
        115                 120                 125

Thr Met Met Gly Thr Ser Ile Leu Ser Ile Pro Trp Gly Ile Lys Gln
    130                 135                 140

Ala Gly Phe Thr Thr Gly Met Cys Val Ile Leu Met Gly Leu Leu
145                 150                 155                 160

Thr Leu Tyr Cys Cys Tyr Arg Val Val Lys Ser Arg Thr Met Met Phe
                165                 170                 175

Ser Leu Asp Thr Thr Ser Trp Glu Tyr Pro Asp Val Cys Arg His Tyr
            180                 185                 190

Phe Gly Ser Phe Gly Gln Trp Ser Leu Leu Phe Ser Leu Val Ser
        195                 200                 205

Leu Ile Gly Ala Met Ile Val Tyr Trp Val Leu Met Ser Asn Phe Leu
210                 215                 220

Phe Asn Thr Gly Lys Phe Ile Phe Asn Phe Ile His His Ile Asn Asp
225                 230                 235                 240

Thr Asp Thr Ile Leu Ser Thr Asn Asn Ser Asn Pro Val Ile Cys Pro
                245                 250                 255

Ser Ala Gly Ser Gly Gly His Pro Asp Asn Ser Ser Met Ile Phe Tyr
            260                 265                 270

Ala Asn Asp Thr Gly Ala Gln Gln Phe Glu Lys Trp Trp Asp Lys Ser
        275                 280                 285

Arg Thr Val Pro Phe Tyr Leu Val Gly Leu Leu Leu Pro Leu Leu Asn
    290                 295                 300

Phe Lys Ser Pro Ser Phe Ser Lys Phe Asn Ile Leu Gly Thr Val
305                 310                 315                 320

Ser Val Leu Tyr Leu Ile Phe Leu Val Thr Phe Lys Ala Val Arg Leu
                325                 330                 335

Gly Phe His Leu Glu Phe His Trp Phe Ile Pro Thr Glu Phe Phe Val
            340                 345                 350

Pro Glu Ile Arg Phe Gln Phe Pro Gln Leu Thr Gly Val Leu Thr Leu
        355                 360                 365

Ala Phe Phe Ile His Asn Cys Ile Ile Thr Leu Leu Lys Asn Asn Lys
    370                 375                 380

Lys Gln Glu Asn Asn Val Arg Asp Leu Cys Ile Ala Tyr Met Leu Val
385                 390                 395                 400

Thr Leu Thr Tyr Leu Tyr Ile Gly Val Leu Val Phe Ala Ser Phe Pro
                405                 410                 415

Ser Pro Pro Leu Ser Lys Asp Cys Ile Glu Gln Asn Phe Leu Asp Asn
            420                 425                 430

Phe Pro Ser Ser Asp Thr Leu Ser Phe Ile Ala Arg Ile Phe Leu Leu
```

```
                 435                 440                 445
Phe Gln Met Met Thr Val Tyr Pro Leu Leu Gly Tyr Leu Ala Arg Val
450                 455                 460

Gln Leu Leu Gly His Ile Phe Gly Asp Ile Tyr Pro Ser Ile Phe His
465                 470                 475                 480

Val Leu Ile Leu Asn Leu Ile Val Gly Ala Gly Val Ile Met Ala
                485                 490                 495

Cys Phe Tyr Pro Asn Ile Gly Ile Ile Arg Tyr Ser Gly Ala Ala
                500                 505                 510

Cys Gly Leu Ala Phe Val Phe Ile Tyr Pro Ser Leu Ile Tyr Ile Ile
                515                 520                 525

Ser Leu His Gln Glu Glu Arg Leu Thr Trp Pro Lys Leu Ile Phe His
530                 535                 540

Val Phe Ile Ile Ile Leu Gly Val Ala Asn Leu Ile Val Gln Phe Phe
545                 550                 555                 560

Met
```

<210> SEQ ID NO 2
<211> LENGTH: 271
<212> TYPE: PRT
<213> ORGANISM: Homo sapiens

<400> SEQUENCE: 2

```
Met Ala Ala Gly Gly Arg Met Glu Asp Gly Ser Leu Asp Ile Thr Gln
1               5                   10                  15

Ser Ile Glu Asp Asp Pro Leu Leu Asp Ala Gln Leu Leu Pro His His
                20                  25                  30

Ser Leu Gln Ala His Phe Arg Pro Arg Phe His Pro Leu Pro Thr Val
            35                  40                  45

Ile Ile Val Asn Leu Leu Trp Phe Ile His Leu Val Phe Val Val Leu
        50                  55                  60

Ala Phe Leu Thr Gly Val Leu Cys Ser Tyr Pro Asn Pro Asn Glu Asp
65                  70                  75                  80

Lys Cys Pro Gly Asn Tyr Thr Asn Pro Leu Lys Val Gln Thr Val Ile
                85                  90                  95

Ile Leu Gly Lys Val Ile Leu Trp Ile Leu His Leu Leu Glu Cys
                100                 105                 110

Tyr Ile Gln Tyr His His Ser Lys Ile Arg Asn Arg Gly Tyr Asn Leu
                115                 120                 125

Ile Tyr Arg Ser Thr Arg His Leu Lys Arg Leu Ala Leu Met Ile Gln
                130                 135                 140

Ser Ser Gly Asn Thr Val Leu Leu Ile Leu Cys Met Gln His Ser
145                 150                 155                 160

Phe Pro Glu Pro Gly Arg Leu Tyr Leu Asp Leu Ile Leu Ala Ile Leu
                165                 170                 175

Ala Leu Glu Leu Ile Cys Ser Leu Ile Cys Leu Leu Ile Tyr Thr Val
                180                 185                 190

Lys Ile Arg Arg Phe Asn Lys Ala Lys Pro Glu Pro Asp Ile Leu Glu
                195                 200                 205

Glu Glu Lys Ile Tyr Ala Tyr Pro Ser Asn Ile Thr Ser Glu Thr Gly
                210                 215                 220

Phe Arg Thr Ile Ser Ser Leu Glu Glu Ile Val Glu Lys Gln Gly Asp
225                 230                 235                 240

Thr Ile Glu Tyr Leu Lys Arg His Asn Ala Leu Leu Ser Lys Arg Leu
```

-continued

```
                        245                 250                 255
Leu Ala Leu Thr Ser Ser Asp Leu Gly Cys Gln Pro Ser Arg Thr
                260                 265                 270

<210> SEQ ID NO 3
<211> LENGTH: 914
<212> TYPE: PRT
<213> ORGANISM: Homo sapiens

<400> SEQUENCE: 3

Met Ala Ser Glu Ser Ser Pro Leu Leu Ala Tyr Arg Leu Leu Gly Glu
1               5                   10                  15

Glu Gly Val Ala Leu Pro Ala Asn Gly Ala Gly Pro Gly Gly Ala
            20                  25                  30

Ser Ala Arg Lys Leu Ser Thr Phe Leu Gly Val Val Pro Thr Val
        35                  40                  45

Leu Ser Met Phe Ser Ile Val Val Phe Leu Arg Ile Gly Phe Val Val
50                  55                  60

Gly His Ala Gly Leu Leu Gln Ala Leu Ala Met Leu Leu Val Ala Tyr
65                  70                  75                  80

Phe Ile Leu Ala Leu Thr Val Leu Ser Val Cys Ala Ile Ala Thr Asn
                85                  90                  95

Gly Ala Val Gln Gly Gly Gly Ala Tyr Phe Met Ile Ser Arg Thr Leu
            100                 105                 110

Gly Pro Glu Val Gly Gly Ser Ile Gly Leu Met Phe Tyr Leu Ala Asn
        115                 120                 125

Val Cys Gly Cys Ala Val Ser Leu Leu Gly Leu Val Glu Ser Val Leu
130                 135                 140

Asp Val Phe Gly Ala Asp Ala Thr Gly Pro Ser Gly Leu Arg Val Leu
145                 150                 155                 160

Pro Gln Gly Tyr Gly Trp Asn Leu Leu Tyr Gly Ser Leu Leu Leu Gly
                165                 170                 175

Leu Val Gly Gly Val Cys Thr Leu Gly Ala Gly Leu Tyr Ala Arg Ala
            180                 185                 190

Ser Phe Leu Thr Phe Leu Leu Val Ser Gly Ser Leu Ala Ser Val Leu
        195                 200                 205

Ile Ser Phe Val Ala Val Gly Pro Arg Asp Ile Arg Leu Thr Pro Arg
210                 215                 220

Pro Gly Pro Asn Gly Ser Ser Leu Pro Pro Arg Phe Gly His Phe Thr
225                 230                 235                 240

Gly Phe Asn Ser Ser Thr Leu Lys Asp Asn Leu Gly Ala Gly Tyr Ala
                245                 250                 255

Glu Asp Tyr Thr Thr Gly Ala Val Met Asn Phe Ala Ser Val Phe Ala
            260                 265                 270

Val Leu Phe Asn Gly Cys Thr Gly Ile Met Ala Gly Ala Asn Met Ser
        275                 280                 285

Gly Glu Leu Lys Asp Pro Ser Arg Ala Ile Pro Leu Gly Thr Ile Val
290                 295                 300

Ala Val Ala Tyr Thr Phe Phe Val Tyr Val Leu Leu Phe Phe Leu Ser
305                 310                 315                 320

Ser Phe Thr Cys Asp Arg Thr Leu Leu Gln Glu Asp Tyr Gly Phe Phe
                325                 330                 335

Arg Ala Ile Ser Leu Trp Pro Pro Leu Val Leu Ile Gly Ile Tyr Ala
            340                 345                 350
```

```
Thr Ala Leu Ser Ala Ser Met Ser Ser Leu Ile Gly Ala Ser Arg Ile
            355                 360                 365

Leu His Ala Leu Ala Arg Asp Asp Leu Phe Gly Val Ile Leu Ala Pro
        370                 375                 380

Ala Lys Val Val Ser Arg Gly Gly Asn Pro Trp Ala Ala Val Leu Tyr
385                 390                 395                 400

Ser Trp Gly Leu Val Gln Leu Val Leu Leu Ala Gly Lys Leu Asn Thr
                    405                 410                 415

Leu Ala Ala Val Val Thr Val Phe Tyr Leu Val Ala Tyr Ala Ala Val
                420                 425                 430

Asp Leu Ser Cys Leu Ser Leu Glu Trp Ala Ser Ala Pro Asn Phe Arg
            435                 440                 445

Pro Thr Phe Ser Leu Phe Ser Trp His Thr Cys Leu Leu Gly Val Ala
        450                 455                 460

Ser Cys Leu Leu Met Met Phe Leu Ile Ser Pro Gly Ala Ala Gly Gly
465                 470                 475                 480

Ser Leu Leu Leu Met Gly Leu Leu Ala Ala Leu Leu Thr Ala Arg Gly
                    485                 490                 495

Gly Pro Ser Ser Trp Gly Tyr Val Ser Gln Ala Leu Leu Phe His Gln
                500                 505                 510

Val Arg Lys Tyr Leu Leu Arg Leu Asp Val Arg Lys Asp His Val Lys
            515                 520                 525

Phe Trp Arg Pro Gln Leu Leu Leu Val Gly Asn Pro Arg Gly Ala
        530                 535                 540

Leu Pro Leu Leu Arg Leu Ala Asn Gln Leu Lys Lys Gly Gly Leu Tyr
545                 550                 555                 560

Val Leu Gly His Val Thr Leu Gly Asp Leu Asp Ser Leu Pro Ser Asp
                    565                 570                 575

Pro Val Gln Pro Gln Tyr Gly Ala Trp Leu Ser Leu Val Asp Arg Ala
                580                 585                 590

Gln Val Lys Ala Phe Val Asp Leu Thr Leu Ser Pro Ser Val Arg Gln
            595                 600                 605

Gly Ala Gln His Leu Leu Arg Ile Ser Gly Leu Gly Gly Met Lys Pro
        610                 615                 620

Asn Thr Leu Val Leu Gly Phe Tyr Asp Asp Ala Pro Pro Gln Asp His
625                 630                 635                 640

Phe Leu Thr Asp Pro Ala Phe Ser Glu Pro Ala Asp Ser Thr Arg Glu
                    645                 650                 655

Gly Ser Ser Pro Ala Leu Ser Thr Leu Phe Pro Pro Arg Ala Pro
                660                 665                 670

Gly Ser Pro Arg Ala Leu Asn Pro Gln Asp Tyr Val Ala Thr Val Ala
            675                 680                 685

Asp Ala Leu Lys Met Asn Lys Asn Val Val Leu Ala Arg Ala Ser Gly
        690                 695                 700

Ala Leu Pro Pro Glu Arg Leu Ser Arg Gly Ser Gly Thr Ser Gln
705                 710                 715                 720

Leu His His Val Asp Val Trp Pro Leu Asn Leu Leu Arg Pro Arg Gly
                    725                 730                 735

Gly Pro Gly Tyr Val Asp Val Cys Gly Leu Phe Leu Gln Met Ala
                740                 745                 750

Thr Ile Leu Gly Met Val Pro Ala Trp His Ser Ala Arg Leu Arg Ile
            755                 760                 765

Phe Leu Cys Leu Gly Pro Arg Glu Ala Pro Gly Ala Ala Glu Gly Arg
```

```
                    770                 775                 780
Leu Arg Ala Leu Leu Ser Gln Leu Arg Ile Arg Ala Glu Val Gln Glu
785                 790                 795                 800

Val Val Trp Gly Glu Gly Ala Gly Ala Gly Glu Pro Glu Ala Glu Glu
                    805                 810                 815

Glu Gly Asp Phe Val Asn Ser Gly Arg Gly Asp Ala Glu Glu Glu Ala
                    820                 825                 830

Leu Ala Arg Ser Ala Asn Ala Leu Val Arg Ala Gln Gln Gly Arg Gly
                    835                 840                 845

Thr Gly Gly Pro Gly Gly Pro Glu Gly Gly Asp Ala Glu Gly Pro
850                 855                 860

Ile Thr Ala Leu Thr Phe Leu Tyr Leu Pro Arg Pro Pro Ala Asp Pro
865                 870                 875                 880

Ala Arg Tyr Pro Arg Tyr Leu Ala Leu Leu Glu Thr Leu Thr Arg Asp
                    885                 890                 895

Leu Gly Pro Thr Leu Leu Val His Gly Val Thr Pro Val Thr Cys Thr
                    900                 905                 910

Asp Leu

<210> SEQ ID NO 4
<211> LENGTH: 805
<212> TYPE: PRT
<213> ORGANISM: Homo sapiens

<400> SEQUENCE: 4

Met Ala Asn Val Ser Lys Lys Val Ser Trp Ser Gly Arg Asp Arg Asp
1               5                   10                  15

Asp Glu Glu Ala Ala Pro Leu Leu Arg Arg Thr Ala Arg Pro Gly Gly
                20                  25                  30

Gly Thr Pro Leu Leu Asn Gly Ala Gly Pro Gly Ala Ala Arg Gln Ser
            35                  40                  45

Pro Arg Ser Ala Leu Phe Arg Val Gly His Met Ser Ser Val Glu Leu
        50                  55                  60

Asp Asp Glu Leu Leu Asp Pro Asp Met Asp Pro Pro His Pro Phe Pro
65                  70                  75                  80

Lys Glu Ile Pro His Asn Glu Lys Leu Leu Ser Leu Lys Tyr Glu Ser
                85                  90                  95

Leu Asp Tyr Asp Asn Ser Glu Asn Gln Leu Phe Leu Glu Glu Glu Arg
                100                 105                 110

Arg Ile Asn His Thr Ala Phe Arg Thr Val Glu Ile Lys Arg Trp Val
            115                 120                 125

Ile Cys Ala Leu Ile Gly Ile Leu Thr Gly Leu Val Ala Cys Phe Ile
        130                 135                 140

Asp Ile Val Val Glu Asn Leu Ala Gly Leu Lys Tyr Arg Val Ile Lys
145                 150                 155                 160

Gly Asn Ile Asp Lys Phe Thr Glu Lys Gly Gly Leu Ser Phe Ser Leu
                165                 170                 175

Leu Leu Trp Ala Thr Leu Asn Ala Ala Phe Val Leu Val Gly Ser Val
                180                 185                 190

Ile Val Ala Phe Ile Glu Pro Val Ala Ala Gly Ser Gly Ile Pro Gln
            195                 200                 205

Ile Lys Cys Phe Leu Asn Gly Val Lys Ile Pro His Val Val Arg Leu
        210                 215                 220

Lys Thr Leu Val Ile Lys Val Ser Gly Val Ile Leu Ser Val Val Gly
```

```
                225                 230                 235                 240
Gly Leu Ala Val Gly Lys Glu Gly Pro Met Ile His Ser Gly Ser Val
                    245                 250                 255

Ile Ala Ala Gly Ile Ser Gln Gly Arg Ser Thr Ser Leu Lys Arg Asp
                    260                 265                 270

Phe Lys Ile Phe Glu Tyr Phe Arg Arg Asp Thr Glu Lys Arg Asp Phe
                    275                 280                 285

Val Ser Ala Gly Ala Ala Gly Val Ser Ala Phe Gly Ala Pro
                    290                 295                 300

Val Gly Val Leu Phe Ser Leu Glu Glu Gly Ala Ser Phe Trp Asn
305                 310                 315                 320

Gln Phe Leu Thr Trp Arg Ile Phe Phe Ala Ser Met Ile Ser Thr Phe
                    325                 330                 335

Thr Leu Asn Phe Val Leu Ser Ile Tyr His Gly Asn Met Trp Asp Leu
                    340                 345                 350

Ser Ser Pro Gly Leu Ile Asn Phe Gly Arg Phe Asp Ser Glu Lys Met
                    355                 360                 365

Ala Tyr Thr Ile His Glu Ile Pro Val Phe Ile Ala Met Gly Val Val
                    370                 375                 380

Gly Gly Val Leu Gly Ala Val Phe Asn Ala Leu Asn Tyr Trp Leu Thr
385                 390                 395                 400

Met Phe Arg Ile Arg Tyr Ile His Arg Pro Cys Leu Gln Val Ile Glu
                    405                 410                 415

Ala Val Leu Val Ala Ala Val Thr Ala Thr Val Ala Phe Val Leu Ile
                    420                 425                 430

Tyr Ser Ser Arg Asp Cys Gln Pro Leu Gln Gly Gly Ser Met Ser Tyr
                    435                 440                 445

Pro Leu Gln Leu Phe Cys Ala Asp Gly Glu Tyr Asn Ser Met Ala Ala
                    450                 455                 460

Ala Phe Phe Asn Thr Pro Glu Lys Ser Val Val Ser Leu Phe His Asp
465                 470                 475                 480

Pro Pro Gly Ser Tyr Asn Pro Leu Thr Leu Gly Leu Phe Thr Leu Val
                    485                 490                 495

Tyr Phe Phe Leu Ala Cys Trp Thr Tyr Gly Leu Thr Val Ser Ala Gly
                    500                 505                 510

Val Phe Ile Pro Ser Leu Leu Ile Gly Ala Ala Trp Gly Arg Leu Phe
                    515                 520                 525

Gly Ile Ser Leu Ser Tyr Leu Thr Gly Ala Ala Ile Trp Ala Asp Pro
                    530                 535                 540

Gly Lys Tyr Ala Leu Met Gly Ala Ala Ala Gln Leu Gly Gly Ile Val
545                 550                 555                 560

Arg Met Thr Leu Ser Leu Thr Val Ile Met Met Glu Ala Thr Ser Asn
                    565                 570                 575

Val Thr Tyr Gly Phe Pro Ile Met Leu Val Leu Met Thr Ala Lys Ile
                    580                 585                 590

Val Gly Asp Val Phe Ile Glu Gly Leu Tyr Asp Met His Ile Gln Leu
                    595                 600                 605

Gln Ser Val Pro Phe Leu His Trp Glu Ala Pro Val Thr Ser His Ser
                    610                 615                 620

Leu Thr Ala Arg Glu Val Met Ser Thr Pro Val Thr Cys Leu Arg Arg
625                 630                 635                 640

Arg Glu Lys Val Gly Val Ile Val Asp Val Leu Ser Asp Thr Ala Ser
                    645                 650                 655
```

-continued

```
Asn His Asn Gly Phe Pro Val Val Glu His Ala Asp Asp Thr Gln Pro
        660                 665                 670

Ala Arg Leu Gln Gly Leu Ile Leu Arg Ser Gln Leu Ile Val Leu Leu
        675                 680                 685

Lys His Lys Val Phe Val Glu Arg Ser Asn Leu Gly Leu Val Gln Arg
        690                 695                 700

Arg Leu Arg Leu Lys Asp Phe Arg Asp Ala Tyr Pro Arg Phe Pro Pro
705                 710                 715                 720

Ile Gln Ser Ile His Val Ser Gln Asp Glu Arg Glu Cys Thr Met Asp
                725                 730                 735

Leu Ser Glu Phe Met Asn Pro Ser Pro Tyr Thr Val Pro Gln Glu Ala
        740                 745                 750

Ser Leu Pro Arg Val Phe Lys Leu Phe Arg Ala Leu Gly Leu Arg His
        755                 760                 765

Leu Val Val Val Asp Asn Arg Asn Gln Val Gly Leu Val Thr Arg
        770                 775                 780

Lys Asp Leu Ala Arg Tyr Arg Leu Gly Lys Arg Gly Leu Glu Glu Leu
785                 790                 795                 800

Ser Leu Ala Gln Thr
                805

<210> SEQ ID NO 5
<211> LENGTH: 25
<212> TYPE: PRT
<213> ORGANISM: Artificial
<220> FEATURE:
<223> OTHER INFORMATION: C-terminal 25 amino acids of H-Ras

<400> SEQUENCE: 5

Gln His Lys Leu Arg Lys Leu Asn Pro Pro Asp Glu Ser Gly Pro Gly
1               5                   10                  15

Cys Met Ser Cys Lys Cys Val Leu Ser
            20                  25

<210> SEQ ID NO 6
<211> LENGTH: 21
<212> TYPE: DNA
<213> ORGANISM: Artificial
<220> FEATURE:
<223> OTHER INFORMATION: shRNA targeting SLC38A9

<400> SEQUENCE: 6
gccttgacaa cagttctata t                                             21

<210> SEQ ID NO 7
<211> LENGTH: 21
<212> TYPE: DNA
<213> ORGANISM: Artificial
<220> FEATURE:
<223> OTHER INFORMATION: shRNA targeting SLC38A9

<400> SEQUENCE: 7
cctctactgt ttgggacagt a                                             21

<210> SEQ ID NO 8
<211> LENGTH: 21
<212> TYPE: DNA
<213> ORGANISM: Artificial
<220> FEATURE:
<223> OTHER INFORMATION: shRNA targeting SLC38A9
```

```
<400> SEQUENCE: 8
tgcccgacaa ccactacctg a                                               21

<210> SEQ ID NO 9
<211> LENGTH: 20
<212> TYPE: DNA
<213> ORGANISM: Artificial
<220> FEATURE:
<223> OTHER INFORMATION: AAVS1 CRISPR/CAS9 guide sequence

<400> SEQUENCE: 9
ggggccacta gggacaggat                                                 20

<210> SEQ ID NO 10
<211> LENGTH: 23
<212> TYPE: DNA
<213> ORGANISM: Artificial
<220> FEATURE:
<223> OTHER INFORMATION: SLC38A9-1 CRISPR/CAS9 guide sequence

<400> SEQUENCE: 10
ggctcaaact ggatattcat agg                                             23

<210> SEQ ID NO 11
<211> LENGTH: 23
<212> TYPE: DNA
<213> ORGANISM: Artificial
<220> FEATURE:
<223> OTHER INFORMATION: SLC38A9-2 CRISPR/CAS9 guide sequence

<400> SEQUENCE: 11
ggagctggaa ctacatggtc tgg                                             23

<210> SEQ ID NO 12
<211> LENGTH: 31
<212> TYPE: PRT
<213> ORGANISM: Artificial
<220> FEATURE:
<223> OTHER INFORMATION: SLC38A9.1 homolog F13H10.3 from C. elegans

<400> SEQUENCE: 12

Glu His Asn Asn Ala Leu Arg Tyr Arg Leu Tyr Asn Arg Leu Asp Pro
1               5                   10                  15

Gly Gly Glu His Leu Thr Met Pro Asp His Val Leu Pro Pro Asn
            20                  25                  30
```

METHODS FOR IDENTIFYING COMPOUNDS AS MODULATORS OF SLC38A9 INTERACTIONS

RELATED APPLICATIONS

This application is a national stage filing under 35 U.S.C. 371 of International Application No. PCT/US2015/28885, filed May 1, 2015, which claims the benefit of U.S. Provisional Application Ser. No. 62/095,512, filed Dec. 22, 2014, and U.S. Provisional Application Ser. No. 61/987,769, filed May 2, 2014, the entire teachings of which are incorporated herein by reference.

GOVERNMENT SUPPORT

This invention was made with government support under R01 CA129105, R01 CA103866, and R01 A1047389 awarded by the National Institutes of Health. The government has certain rights in the invention.

BACKGROUND OF THE INVENTION

The invention relates to methods of identifying compounds that modulate mTORC1 activity in a cell by modulating the activity of SLC38A9 (NCBI Gene ID: 153129), as well as to the use of such identified compounds in the modulation of mTORC1 and the treatment of diseases and conditions characterized by aberrant mTORC1 activity.

The mammalian (mechanistic) target of rapamycin (mTOR) is a master regulator of cell, organ and organismal growth in response to nutrients, growth factors and stress factors. mTOR is a serine/threonine kinase and nucleates at least two distinct complexes, mTOR complex 1, mTORC1, and mTOR complex 2, mTORC2. mTORC1 activity is regulated in part by amino acids. When activated, mTORC1 can stimulate cell growth by promoting anabolic processes such as mRNA translation and inhibiting catabolic processes such as autophagy through the actions of its downstream substrates. However, aberrant mTORC1 activation has been observed in a wide range of diseases including multiple types of cancer, metabolic dysfunction (e.g. type 2 diabetes, obesity), auto-immune diseases (e.g. psoriasis) and neurodegenerative diseases (e.g. Alzheimer's and Parkinson's disease), neuropsychiatric syndromes (e.g. autism and major depressive disorders), skeletal muscle dysfunction (e.g. sarcopenia, disease induced cachexia and disuse atrophy), as well as several rare diseases including those resulting from inherited and acquired mitochondrial dysfunction (e.g. Leigh Syndrome) and certain inherited growth defects.

The mechanism by which amino acids regulate mTORC1 signaling is complex and is centered on the lysosome. In amino acid replete conditions, amino acids cross the plasma membrane and accumulate within the lumen of the lysosome. In addition, the degradation of protein in the lysosomal lumen by lysosomal proteases and peptidases can also contribute to the accumulation of amino acids within the lysosome and lead to mTORC1 activation. mTORC1 is recruited to the lysosomal membrane where it interacts with the Rag GTPases—obligate heterodimers of RagA or RagB with RagC or RagD. The Rag GTPase heterodimer does not contain lipid anchors tethering the complex to the lysosome. Instead, it relies upon the pentameric Ragulator complex, which is tethered to the lysosomal membrane via lipidation of the Ragulator component LAMTOR1 (p18) for lysosomal localization. Furthermore, the Ragulator components LAMTOR2-5 (p14, MP1, C7orf59 and HBXIP, respectively) assembled with LAMTOR1 acts as a guanine nucleotide exchange factor for RagA and RagB, fostering their loading with GTP. As a result, Ragulator is not only necessary for localizing the Rag GTPase heterodimer to the lysosomal surface, but for also catalyzing the activated nucleotide binding state of the RagA/B. Additional protein complexes responsive to the availability of amino acids have been identified that regulate the activity of the Ragulator and Rag complexes, but the precise mechanism by which individual amino acids are physically sensed by the mTORC1 pathway has not been elucidated.

Given the known role that leucine and arginine play in activating mTORC1, we hypothesized that proteins exist that are able to specifically sense leucine or arginine at the lysosome and in response activate the lysosomal machinery upstream of mTORC1. We sought to identify such proteins through proteomic and biochemical approaches.

Given the importance of mTORC1 modulation in both anabolic processes and in certain disease states, there is a need to identify other members of the mTORC1 activation pathway as potential targets for modulation, which in turn can modulate mTORC1 activity.

SUMMARY OF THE INVENTION

The present invention solves this problem by identifying the protein isoforms of SLC38A9 as an important component of the mTORC1 regulatory pathway and as the putative amino acid sensor in that pathway that may be pharmacologically manipulated resulting in the selective modulation of mTORC1 activation.

In certain embodiments, disclosed herein are methods of identifying a modulator of mTORC1 activity, such methods comprising the steps of: (a) contacting a test compound with SLC38A9.1 or a fragment or mutant thereof that possesses an activity or characteristic of SLC38A9.1; (b) measuring an activity or characteristic of SLC38A9.1 in the presence of the test compound; and (c) comparing the measured activity or characteristic with the same activity or characteristic in the absence of the test compound, thereby determining whether the test compound is a modulator of SLC38A9.

In certain aspects, the test compound is contacted with SLC38A9.1, SLC38A9 Δ110, or amino acids 1-119 of SEQ ID NO:1 or a fusion protein comprising SLC38A9.1, SLC38 Δ110 or amino acids 1-119 of SEQ ID NO:1; and a heterologous fusion partner. In certain embodiments, the heterologous fusion partner is selected from a N-terminal His tag, a N-terminal poly-His tag, an epitope tag, a ligand tag, a N- or C-terminal plasma membrane signal sequence, a fluorescent polypeptide, or a luminescent polypeptide.

In certain embodiments, the activity or characteristic of SLC38A9.1 is the ability to transfer an amino acid across a membrane. In certain embodiments, the activity or characteristic of SLC38A9.1 is the ability to associate with components of one or more of Ragulator or a RagGTPase.

Also disclosed herein are methods for modulating the level or activity of mTORC1 in a cell, comprising contacting a cell with an agent or composition that modulates the level or activity of SLC38A9. In certain aspects, modulating the level or activity of mTORC1 in the cell comprises increasing the level or activity of mTORC1 in the cell. In certain embodiments, modulating the level or activity of mTORC1 in the cell comprises decreasing the level or activity of mTORC1 in the cell.

In certain embodiments, also disclosed herein are methods for increasing mTORC1 activity in a patient that requires an increase in mTORC1 activity, such methods comprising a step of administering to the patient an agent that activates or agonizes SLC38A9, thereby increasing mTORC1 activity in the patient.

In yet other embodiments, disclosed are methods for decreasing mTORC1 activity in a patient that requires a decrease in mTORC1 activity comprising the step of administering to the patient an agent that inhibits SLC38A9, thereby decreasing mTORC1 activity in the patient.

Also disclosed herein are methods for treating a disease, condition, or disorder which would benefit from increasing the level or activation of mTORC1 in a patient, such methods comprising administering to the subject an effective amount of an agent which activates or agonizes SLC38A9, and thereby treating the disease, condition, or disorder.

In certain aspects, disclosed herein are methods for treating a disease, condition, or disorder which would benefit from decreasing the level or activation of mTORC1 in a patient, the method comprising administering to the subject an effective amount of an agent which inhibits SLC38A9 activity, and thereby treating the disease, condition, or disorder.

The above discussed, and many other features and attendant advantages of the present inventions will become better understood by reference to the following detailed description of the invention.

BRIEF DESCRIPTION OF THE DRAWINGS

FIG. 1A depicts the interaction of full-length SLC38A9.1 or its N-terminal domain with endogenous Ragulator components (p18 and p14) and RagA and RagC GTPases. FIG. 1B depicts an alignment of the portion of the N-terminal domain of SLC38A9.1 required for interaction with Ragulator and Rag GTPases with the SLC38A9.1 homolog F13H10.3 from *C. elegans* as well as key amino acid residues required for such interaction (down arrows), as well as the interaction of SLC38A9.1 or various N-terminal mutants of SLC38A9.1 with endogenous Ragulator (p18 and p14) and RagA and RagC GTPases. FIG. 1C depicts the interaction of SLC38A9.1 with v-ATPase components V0di and V1B2.

FIG. 2A depicts an immunostain demonstrating the effect of amino acids on localization of SLC38A9.1 and the lysosomal membrane protein LAMP-2 in HEK-293T cells stably expressing FLAG-SLC38A9.1. FIG. 2B depicts an immunoblot depicting the effect of amino acids on mTORC1 and SLC38A9 production in HEK-293T cells expressing the indicated short hairpin RNAs.

FIG. 3A depicts the effect of all amino acids, as well as leucine and arginine in cells expressing metap2 (as a control) or SLC38A9.1. FIG. 3B depicts the effect of amino acids in cells expressing metap2, the lysosomal marker protein LAMP1, SLC38A9.1, or SLC38A9.2. FIG. 3C depicts the effect of amino acids in cells expressing metap2, LAMP1, SLC38A9.1, or SLC38A9.1 I68A. FIG. 3D depicts the effect of amino acids in cells expressing metap2, or SLC38A9.1 1-119.

FIG. 4A depicts the effect of amino acids, as well as leucine and arginine, in cells expressing Ragulator components p14 or p18. FIG. 4B depicts the effect of amino acids in cells expressing metap2, the SLC38A9 isoforms SLC38A9.1, SLC38A9.4, SLC38A9.1 1-119 or SLC38A9.2.

FIG. 5A depicts the time dependent uptake of [$^3$H]-arginine by proteoliposomes containing SCL38A9.1. FIG. 5B, left panel, depicts the time course of [$^3$H]arginine uptake, given fixed [$^3$H]arginine (0.5 µM) and increasing concentrations of unlabeled arginine. FIG. 5B, right panel, depicts velocity, calculated from left panel, as a function of total arginine concentration. Data were fitted to the Michaelis-Menton equation. FIG. 5C depicts the time-dependent efflux of SLC38A9.1 proteoliposomes following 1.5 hr loading with 0.5 µM [$^3$H]arginine. FIG. 5D depicts the competition of 0.5 µM [$^3$H]arginine transport by SLC38A9.1 using 100 mM of indicated unlabeled amino acids. The error bars in FIGS. 5A-5D represent standard deviation derived from at least 3 measurements. FIG. 5E is a series of immunoblots depicting impairment of leucine- or arginine-induced activation of the mTORC1 pathway in SLC38A9-null HEK-293T cells and negative control cells (sgAAVS1_1). Cells were starved of the indicated amino acid for 50 minutes and stimulated for 10 minutes using the indicated amino acid concentrations. The leucine and arginine concentrations in RPMI are, respectively, 381 µM and 1.14 mM.

FIG. 6A depicts the interaction with metap2, LAMP1, SLC38A9.1, SLC38A7 (a known lysosomal transporter from the same family as SLC38A9) and SLC36A1 (a known lysosomal membrane protein believed to be involved in mTORC1 regulation). FIG. 6B depicts the interaction with LAMP1, SLC38A9.1 and SLC38A9.2. FIG. 6C depicts the interaction with metap2, LAMP1, SLC38A9.1, SLC38A9.1 Δ110, SLC38A9.4, and SLC38A9.1 1-119.

FIGS. 7A and 7B depict immunostains demonstrating the localization of SLC38A9.2 and SLC38A9.4, as well as LAMP in HEK-293T cells stably expressing FLAG-tagged versions of those SLC38A9 isoforms. FIG. 7C depicts an immunoblot demonstrating the interaction between various isoforms of SLC38A9 and various mutants of Ragulator components in HEK-293T cells expressing the indicated isoforms and mutants. FIG. 7D depicts an immunoblot demonstrating the effect of amino acids on mTORC1 (as analyzed by phosphorylation of the mTORC1 substrate S6K1) in HEK-293T cells knocked down for SLC38A9 with short-interfering RNAs.

FIG. 8A depicts an immunoblot demonstrating the effect of transient overexpression of SLC38A9.1, SLC38A9.4, or SLC38A9.1 Δ110 on mTORC1 sensitivity to amino acids in HEK-293T cells. FIG. 8B depicts an immunoblot demonstrating the effect of stable overexpression of SLC38A9.1 in various cells on mTORC1 sensitivity to amino acids. FIG. 8C depicts an immunoblot demonstrating the effect of stable overexpression of SLC38A9.1 on arginine-starvation and chloroquine-induced autophagy, as measured by the markers of autophagy p62 and LC3 levels.

FIG. 10A depicts immunostaining of HEK-293T cells transiently overexpressing SLC38A9.1 at levels that cause spillover to the plasma membrane. FIGS. 10B-10D depict the effect of transient expression of various proteins in HEK-293T cells on the uptake of labelled amino acids (FIG. 10B—[$^{14}$C]arginine; FIG. 10 C—[$^{14}$C] amino acid mix; FIG. 10D—[$^{14}$C]leucine). FIG. 10E, left panel, depicts whole-cell recordings from HEK-293T cells expressing indicated cDNAs at −80 mV. Quantified is the change in steady-state current following local application of 2.4 mM arginine, 1.6 mM leucine, and 4 mM glutamine (4×DMEM concentrations). FIG. 10E, right panel, depicts representative examples of individual recordings. Grey bars indicate application of amino acids. FIG. 10F depicts the uptake of [$^3$H]-arginine by SLC38A9.1 proteoliposomes or LAMP1 proteoliposomes after incubation with 0.5 μM [$^3$H] arginine for 60 min. followed by chromatography on a column that traps free amino acids. The proteoliposomes pass through the column and were subjected to FLAG immunoblotting (top panel) and scintillation counting (bottom panel).

DETAILED DESCRIPTION OF THE INVENTION

Figure 1A:
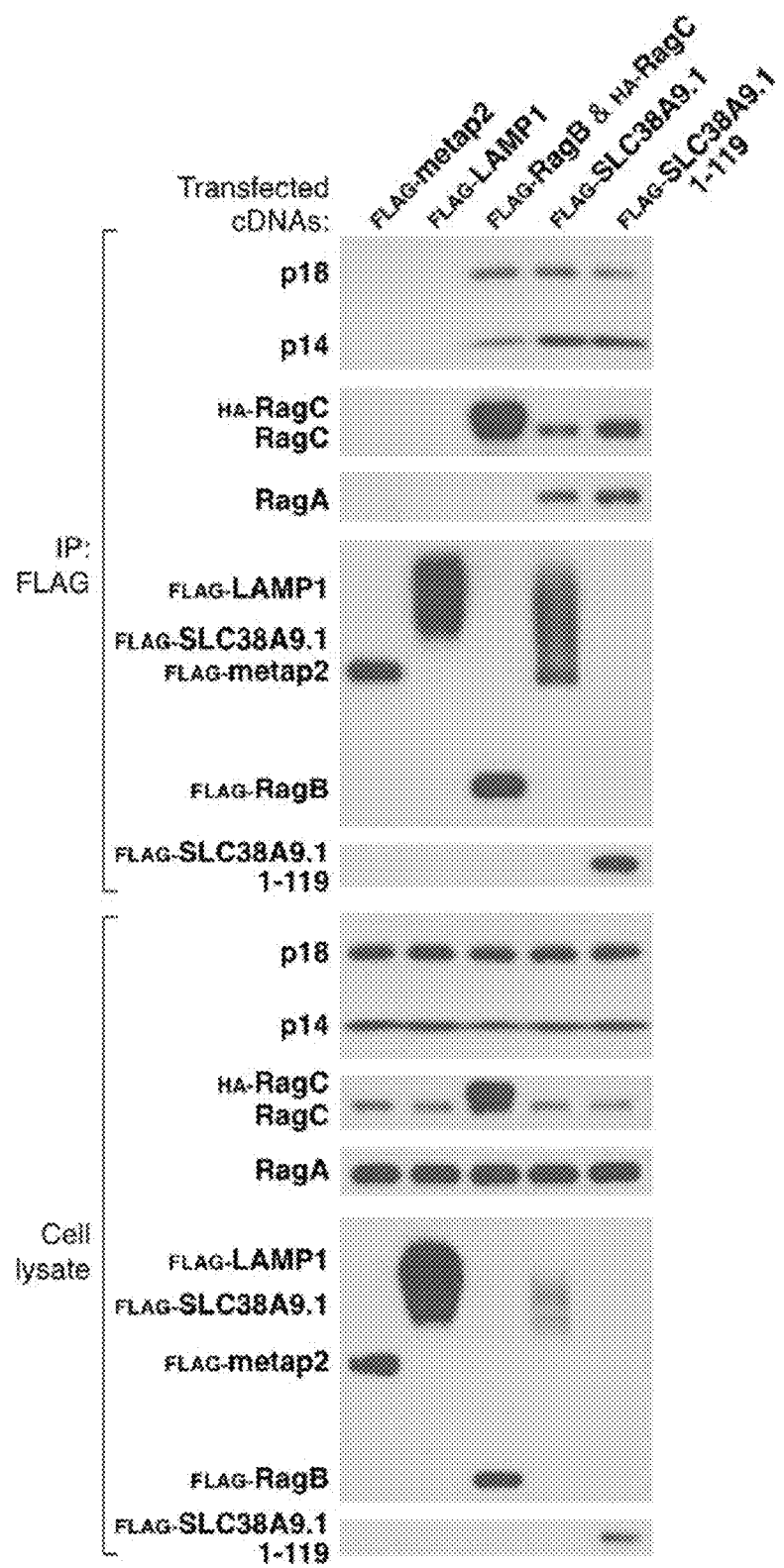
FIGS. 1A-1C depict immunoblots of cell lysates from HEK-293T cells transfected with various FLAG-tagged proteins. HEK-293T cells were transfected with the indicated cDNAs in expression vectors and lysates were prepared. A portion of the lysate was subjected to FLAG immunoprecipitation. Both the cell lysates and the FLAG-immunoprecipitated proteins from the cell lysates were immunoblotted for the indicated proteins.
Figure 1B:
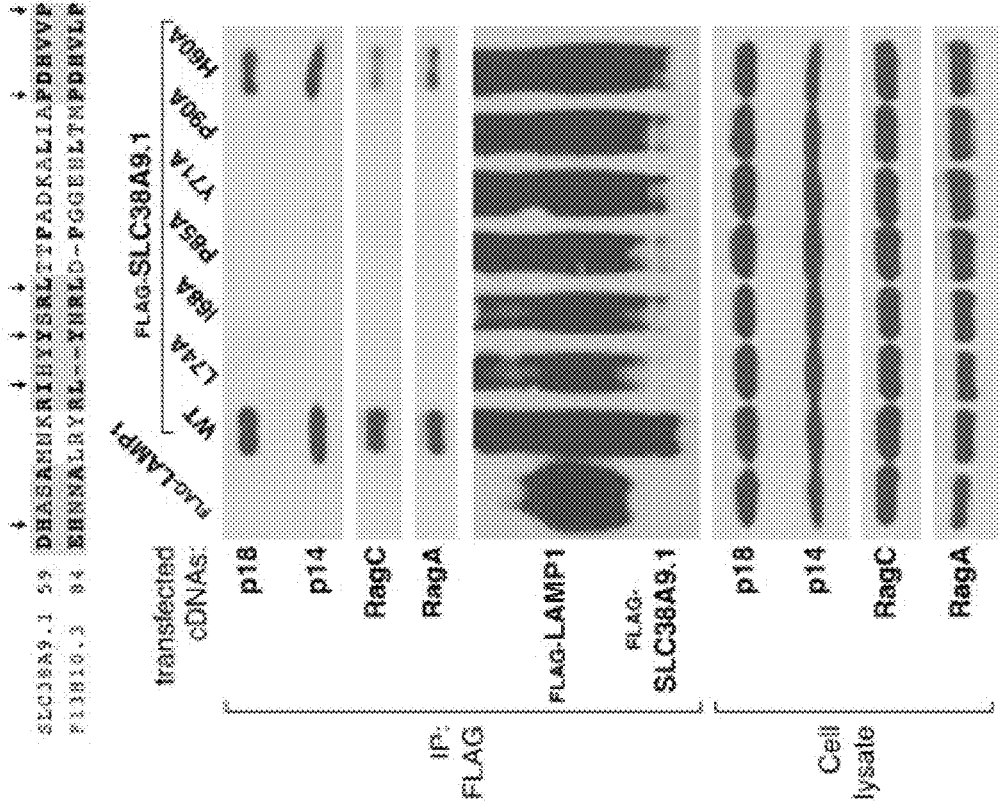

As used herein "modulating" (and verb forms thereof, such as "modulates") means causing or facilitating a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon.

The term "inhibitor" (and verb forms thereof, such as "inhibits"), as used herein means an agent that (a) reduces one or more activities normally associated with the protein being inhibited; (b) reduces or otherwise interferes with the ability of the protein being inhibited to associate with, e.g., bind to, another protein or ligand or nucleic acid; and/or (c) reduces the transcription or expression from a gene that encodes the protein being inhibited.

The terms "activator" and "agonist" (and verb forms thereof, such as "activates" and "agonizes"), as used herein means an agent that (a) increases one or more activities normally associated with the protein being activated; (b) increases or otherwise enhances the ability of the protein being activated to associate with, e.g., bind to, another protein or ligand or nucleic acid; and/or (c) increases the transcription or expression from a gene that encodes the protein being activated. In certain embodiments, modulating, inhibiting, activating and/or agonizing utilizing any of the activating, agonistic, or inhibitory systems, methods or agents described herein can be performed in vitro or ex vivo, for example, by contacting or exposing cells to the activating, agonistic, or inhibitory systems, methods or agents. In certain embodiments, modulating, inhibiting, activating and/or agonizing utilizing any of the activating, agonistic, or inhibitory systems, methods or agents described herein can be performed in vivo.

The term "SLC38A9", "full-length SLC38A9", "SLC38A9 isoform 1" and "SLC38A9.1" are used interchangeably and all refer to the full amino acid sequence set forth in SEQ ID NO:1.

The terms "SLC38A9.2" and "SLC38A9 isoform 2" are used interchangeably and refer to amino acids 64-561 of SEQ ID NO:1.

The terms "SLC38A9.4" and "SLC38A9 isoform 4" are used interchangeably and refer amino acids 120-561 of SEQ ID NO:1.

The term "SLC38A9 Δ110" refers to amino acids 111-564 of SEQ ID NO:1.

In certain embodiments, the invention provide peptides and polypeptides that correspond to a portion of SLC38A9 or polypeptides or peptides that have at least 70%, at least 7.5%, at least 80%, at least 85%, at least 90%, or at least 95% homology at the amino acid level to a portion of the SLC38A9 amino acid sequence (SEQ ID NO:1). In one particular aspect of these embodiments, the peptide or polypeptide fragment comprises at least amino acids 1-119 of SEQ ID NO:1. This amino terminal domain of SLC38A9 appears to be responsible for binding to Ragulator. In a more specific aspect of these embodiments, the peptide or polypeptide fragment corresponds to at least amino acids 59-90 of SEQ ID NO:1. In an alternate aspect the polypeptide or peptide comprises an amino acid sequence that is at least 70%, at least 75%, at least 80%, at least 85%, at least 90%, or at least 95% homologous to amino acids 1-119 or amino acids 59-90 of SEQ ID NO:1. In still another specific aspect the at least 70% homologous polypeptide differs from amino acid sequence of SEQ ID NO:1 by substitution of at least one or more of D59, H60, S62, S72, R73, P77, D86, and V88 with a different amino acid. In certain aspects, at least one or more of D59, H60, S62, S72, R73, P77, D86, and V88 is substituted with an alanine. In still another specific aspect the at least 70% homologous polypeptide comprises at least amino acids corresponding to I68, Y71, L74, P85, V89, and P90 of SEQ ID NO:1, In still another aspect of these embodiments, the peptide, polypeptide or homologue thereof lacks amino acid sequence corresponding to or that define any transmembrane domain of SLC38A9, e.g., none of amino acids 120-561 of SEQ ID NO:1. In certain embodiments, the peptide, polypeptide or homologue thereof is capable of entering a cell. This may be achieved by methods known in the art, including the addition of a cell adhesion amino acid sequence in the peptide or polypeptide, such as Arg-Gly-Asp, the use of conformationally stabilized "stapled" polypeptides and the use of fusion proteins wherein the fusion partner of the peptide, polypeptide or homolog thereof is a cell-permeable polypeptide sequence. In an alternate embodiment, the peptide or polypeptide fragment consists of amino acids 111-561 of SEQ ID NO:1.

In related aspects of this alternate embodiment, the peptide or polypeptide fragment consists essentially of a plasma membrane targeting sequence fused directly or through a linker to the N- or C-terminus of any of the above described peptides or polypeptide fragments thereof. In a more specific aspect, the peptide or polypeptide fragment consists essentially of a plasma membrane targeting sequence fused directly or through a linker to the N- or C-terminus of either amino acids 111-561 of SEQ ID NO:1 or to amino acids 1-561 of SEQ ID NO:1. Plasma membrane targeting sequences are well-known in the art (see, e.g., Bhardwaj, N., et al Bioinformatics 23:3110-3112 (2007)). In a more specific aspect, the plasma membrane targeting sequence is the C-terminal 25 amino acids of H-Ras (QHKLRKLNPPDESGPGCMSCKCVLS=SEQ ID NO: 5). In a related more specific aspect, the peptide or polypeptide fragment consists of a variant of any of SEQ ID NO:1 or any of the above described peptides or polypeptide fragments thereof, wherein the lysosomal targeting sequence has been eliminated by amino acids substitution(s), insertion(s) and/or addition(s).

In certain embodiments, the peptides, polypeptides, fusion proteins and homologs thereof of the invention are useful as competitive inhibitors for the binding of SLC38A9 to Ragulator. In other embodiments, the peptides, polypeptides, fusion proteins and homologs thereof of the invention are useful in assays to identify modulators of SLC38A9. Such modulators may alter the affinity of SLC38A9 for one or more amino acids, e.g., arginine, histidine or lysine, or alter the interaction between SLC38A9 and Ragulator.

In a related embodiment, the invention provides nucleic acid sequences coding for one or more the above-described peptides, polypeptides, fusion proteins and homologs thereof; vectors comprising such nucleic acid sequences; and cells transformed with such vectors and/or expressing the product of such nucleic acid sequences.

In another embodiment, the invention provides a protein scaffold modulator of SLC38A9. Protein scaffold modulators are small proteins that are capable of entering into a cell and binding to a target protein, and may be capable of altering the target protein's activity. Protein scaffold modulators include, but are not limited to, affibodies, two-helix antibodies, knottins, monobodies (also known as adnectins), anticalins, designed ankyrin repeat proteins (DARPins), Alpahbodies™, avimers, immunoglobulin-derived binding fragments, single chain antibodies and fragments thereof, as well as derivatives of natural ligands, such as VEGF, EGF and Annexin V. Protein scaffold modulators of the invention may be either SLC38A9-activating or SLC38A9-inhibitory. Appropriate protein scaffold modulators may be identified by screening of phage, cell or ribosomal display libraries, which are either commercially available or may be created by those of ordinary skill in the art. The activity of the protein scaffold modulators of SLC38A9 may be determined, e.g., by its ability to cause a change in the affinity of SLC38A9 for Ragulator or one or more other proteins we believe are associated with SLC38A9, e.g., TMEM192 (NCBI Gene ID: 201931; SEQ ID NO:2), SLC12A9 (NCBI Gene ID: 56996; SEQ ID NO:3) or CLCN7 (NCBI Gene ID: 1186; SEQ ID NO:4). Alternatively the activity of the protein scaffold modulators of SLC38A9 may be determined by its ability to cause a change in one or more activities of SLC38A9. In one aspect of this embodiment, the protein scaffold modulator is an inhibitor of SLC38A9. In an alternate embodiment, the protein scaffold modulator is an activator or agonist of SLC38A9.

In another embodiment, the invention provides a small molecule modulator of SLC38A9. In one aspect of this embodiment, the small molecule modulator is an inhibitor of SLC38A9 and causes a decrease in mTORC1 activity in a cell. In an alternate aspect of this embodiment, the small molecule modulator is an activator or agonist of SLC38A9 and causes an increase in mTORC1 activity in a cell. In a more specific embodiment, the small molecule modulator is an activator or agonist of SLC38A9 and is other than arginine, lysine, or leucine. In still another embodiment, the small molecule modulator is an activator or agonist of SLC38A9 and is a functional mimetic of arginine, lysine or leucine. The term "mimetic" as used herein refers to an agent that either emulates the biological effects of arginine, lysine, or leucine on mTORC1 activation in a cell, as measured by mTORC1 phosphorylation of an mTORC1 substrate (e.g., S6K) in response to the agent, or that increases, directly or indirectly, the level of arginine, lysine, or leucine in a cell. In certain aspects of these embodiments, the small molecule modulator is not a peptide or peptide analog having at least 10% arginine, lysine or leucine content (e.g. at least 10% of the amino acids in the peptide are one of arginine, lysine or leucine). Small molecule modulators of SLC38A9, may be identified by screening commercially available small molecule and natural product libraries and may be further optimized for SCL38A9 modulating activity by well-known medicinal chemistry manipulations and modifications.

In another embodiment, the invention provides a small molecule modulator of one or more of TMEM192 (NCBI Gene ID: 201931; SEQ ID NO:2), SLC12A9 (NCBI Gene ID: 56996; SEQ ID NO:3) or CLCN7 (NCBI Gene ID: 1186; SEQ ID NO:4). In one aspect of this embodiment, the small molecule modulator is an inhibitor of TMEM192, SLC12A9 or CLCN7 and causes a decrease in mTORC1 activity in a cell. In an alternate aspect of this embodiment, the small molecule modulator is an activator or agonist of TMEM192, SLC12A9 or CLCN7 and causes an increase in mTORC1 activity in a cell. In a more specific embodiment, the small molecule modulator is an activator or agonist of TMEM192, SLC12A9 or CLCN7 and is other than arginine, lysine, or leucine. In still another embodiment, the small molecule modulator is an activator or agonist of TMEM192, SLC12A9 or CLCN7 and is a mimetic of arginine, lysine or leucine. In certain aspects of these embodiments, the small molecule modulator is not a peptide or peptide analog having at least 10% arginine, lysine or leucine content (e.g. at least 10% of the amino acids in the peptide are one of arginine, lysine or leucine). Small molecule modulators of TMEM192, SLC12A9 or CLCN7, may be identified by screening commercially available small molecule libraries and may be further optimized for TMEM192, SLC12A9 or CLCN7 modulating activity by well-known medicinal chemistry manipulations and modifications.

In still another embodiment, the invention provides one or more oligonucleotides, e.g., a siRNA, shRNA or antisense oligonucleotide that is complementary to and specifically hybridizes to DNA or mRNA encoding one or more of SLC38A9, TMEM192, SLC12A9 or CLCN7. The oligonucleotides of this invention must be capable of decreasing the transcription and/or translation of the corresponding protein.

In another embodiment, the invention provides a CRISPR/CAS9 system and means that modulates expression of one or more of SLC38A9, TMEM192, SLC12A9 or CLCN7. CRISPR/CAS9 systems and means for their preparation and use are known in the art and may be utilized to either increase or decrease the expression of a specific gene.

Accordingly, in one aspect of this embodiment, the CRISPR/CAS9 system causes inhibition of expression of one or more of SLC38A9, TMEM192, SLC12A9 or CLCN7. In another aspect of this embodiment, the CRISPR/CAS9 system causes an increase in expression of one or more of SLC38A9, TMEM192, SLC12A9 or CLCN7.

In still another embodiment, the invention provides a small molecule modulator of transcription of one of more of SLC38A9, TMEM192, SLC12A9 or CLCN7 genomic open reading frames. Such a small molecule include those that modulate the presence and activity of one or more of activating transcription factors, transcriptional co-activators, and transcriptional repressors and/or the subsequent recruitment of the transcriptional machinery at the promoters of one of more of SLC38A9, TMEM192, SLC12A9 or CLCN7. In one aspect of this embodiment, the small molecule modulator increases transcription of one of more of SLC38A9, TMEM192, SLC12A9 or CLCN7 genomic open reading frames. In an alternate aspect of this embodiment, the small molecule modulator decreases transcription of one of more of SLC38A9, TMEM192, SLC12A9 or CLCN7 genomic open reading frames.

In still another embodiment, the invention provides a small molecule modulator of translation of one of more of SLC38A9, TMEM192, SLC12A9 or CLCN7 mRNA. In one aspect of this embodiment, the small molecule modulator increases translation of one of more of SLC38A9, TMEM192, SLC12A9 or CLCN7 mRNA. In an alternate aspect of this embodiment, the small molecule modulator decreases translation of one of more of SLC38A9, TMEM192, SLC12A9 or CLCN7 mRNA.

In still another embodiment, the invention provides a small molecule modulator of protein degradation of one of more of SLC38A9, TMEM192, SLC12A9 or CLCN7 protein levels. In one aspect of this embodiment, the small molecule modulator increases degradation of one of more of SLC38A9, TMEM192, SLC12A9 or CLCN7 proteins. In an alternate aspect of this embodiment, the small molecule modulator decreases degradation of one of more of SLC38A9, TMEM192, SLC12A9 or CLCN7 proteins In still another embodiment, the invention provides an agent that reduces or eliminates glycosylation of SLC38A9. In one aspect of this embodiment, the agent causes partial or complete deglycosylation at one or more of amino acid residues 117, 239, 248, 266 or 274 of SLC38A9.

In a related embodiment, the invention provides partially or completely deglycosylated forms of SLC38A9, polypeptide or peptide fragments of SLC38A9, or homologs of polypeptide or peptide fragments of SLC38A9. In this embodiment, the SLC38A9, or polypeptide or peptide fragment comprises at least one of amino acid residues 117, 239, 248, 266 or 274 of SLC38A9. Homologs useful in this embodiment may be mutated at one or more amino acids corresponding to a glycosylation signal in residue SLC38A9. These mutations can occur at any asparagine in SLC38A9 that is putatively N-glycosylated (i.e., amino acids corresponding to amino acid 117, 239, 248, 266 or 274 of SLC38A9) and/or at either of the two amino acids immediately C-terminal to those putative N-glycosylation sites, such that the three amino acid N-glycosylation signal is eliminated.

In another embodiment, the invention provides a method for increasing mTORC1 activity in a patient comprising the step of administering to the patient an agent that activates or agonizes SLC38A9. Any of the above-described SLC38A9-activating or agonistic systems, methods or agents may be employed for this purpose.

In a related embodiment, the invention provides a method for increasing mTORC1 activity in a patient comprising the step of administering to the patient an agent that activates or agonizes one of more of TMEM192, SLC12A9 or CLCN7. Any of the above-described TMEM192-, SLC12A9- or CLCN7-activating or agonistic systems, methods or agents may be employed for this purpose.

In some embodiments, the method of increasing mTORC1 is used to promote muscle anabolism, improve muscle function, increase muscle mass, reverse muscle atrophy or to prevent muscle atrophy. In some embodiments, the method is used to reverse muscle atrophy or to prevent muscle atrophy due to inactivity due to lifestyle, inactivity caused by orthopedic surgery, immobilization, or age of the subject or a disease or condition the subject has or suffers from. In some embodiments, the method is used to reverse muscle atrophy or to prevent muscle atrophy due to a broken bone, a severe burn, a spinal injury, an amputation, a degenerative disease, a condition wherein recovery requires bed rest for the subject, a stay in an intensive care unit, or long-term hospitalization. In some embodiments, the method is used to treat a disease, condition or disorder resulting in skeletal muscle atrophy, such as sarcopenia, muscle denervation, and muscular dystrophy.

In some embodiments, the subject that requires an increase in mTORC1 activity has decreased satiety, e.g., due to cachexia or anorexia. In some embodiments, the subject that requires an increase in mTORC1 activity has or suffers from a disease or condition known to be associated with cachexia and selected from cancer, AIDS, SARS, chronic heart failure, COPD, rheumatoid arthritis, liver disease, kidney disease and trauma. In some embodiments, the subject has or suffers from a disease or condition known to be associated with malabsorption. In some embodiments, the disease or condition is selected from Crohn's disease, irritable bowel syndrome, celiac disease, and cystic fibrosis. In some embodiments, the subject has or suffers from malnutrition, sarcopenia, muscle denervation, muscular dystrophy, an inflammatory myopathy, spinal muscular atrophy (SMA), amyotrophic lateral sclerosis (ALS), or myasthenia gravis. In some embodiments, the subject is preparing for, participating in or has recently returned from space travel. In some embodiments, the subject is preparing for, participating in or has recently returned from an armed conflict or military training.

In some embodiments, the method is used to treat a ribosomopathy. In some embodiments, the ribosomopathy is selected from Diamond-Blackfan anemia, 5q-syndrome, Shwachman-Diamond syndrome, X-linked dyskeratosis, cartilage hair hypoplasia, and Treacher Collins syndrome.

In some embodiments, the method is used to treat cohesinopathies (e.g. Roberts syndrome and Cornelia de Lange syndrome).

In some embodiments, the method of increasing mTORC1 activity is used to prevent autophagy in the patient. In some embodiments, the subject has or suffers from therapy resistant cancer in a manner dependent upon induction of autophagy.

In some embodiments, the method is used to treat or prevent depression. In some embodiments, the method is used to treat or prevent forms of autism that are characterized by depleted amino acid levels. In some embodiments, the method of increasing mTORC1 activity is used to treat or prevent jet lag.

In some embodiments, the method is used to prevent or reverse cardiac muscle atrophy in the subject. In some embodiments, the subject has or has had a disease or condition selected from heart attack, congestive heart failure, heart transplant, heart valve repair, atherosclerosis, other major blood vessel disease, and heart bypass surgery.

In some embodiments, the method of increasing mTORC1 activity is used to increase strength and/or to increase muscle mass following exercise. In some embodiments, the method is carried out in conjunction with physical therapy, as part of total parenteral nutrition, or to promote functional electrical stimulation.

In another embodiment, the invention provides a method for decreasing mTORC1 activity in a patient comprising the step of administering to the patient an agent that inhibits SLC38A9. Any of the above-described SLC38A9-inhibiting systems, methods or agents may be employed for this purpose. In one aspect of this embodiment, the patient is an organ transplant recipient, is in need of immunosuppression, is a stent recipient, has or suffers from or at risk of developing arterial stenosis, or has or suffers from cancer, in particular a cancer for which treatment with rapamycin is recommended or approved by a regulatory agency. In another aspect of this embodiment, the patient is suffering from a disease or condition selected from a metabolic disease (e.g., type 2 diabetes, obesity, non-alcoholic steatohepatitis (NASH), and hyperlipidemia), a neurodegenerative disease (e.g., Alzheimer's disease, Parkinson's Disease, Huntington's Disease, and amyotrophic lateral sclerosis), an autoimmune disease (e.g., psoriasis, rheumatoid arthritis, multiple sclerosis, systemic lupus erythematosus, gout, allergic rhinitis, Crohn's Disease, and ulcerative colitis), rare and mitochondrial disease (e.g., Leigh's Syndrome, Friedreich's Ataxia, Cardiomyopathy, Leber's Hereditary Optic Neuropathy, lymphangioleiomyomatosis, tuberous sclerosis, Pompe Disease (Glycogen storage disease II), and lysosomal storage diseases), cardiovascular disease (e.g., cardiomyopathy, heart failure, ischemic heart disease (atherosclerotic disease), ischemic stroke, and pulmonary arterial hypertension), renal disease (e.g., diabetic nephropathy, polycystic kidney disease, and acute kidney injury), neuropsychiatric disease (e.g., epilepsy, autism spectrum disorder, and depressive disorder), and oncological disease (e.g., renal cell carcinoma, solid tumors, hematological cancers.

In a related embodiment, the invention provides a method for decreasing mTORC1 activity in a patient comprising the step of administering to the patient an agent that inhibits one of more of TMEM192, SLC12A9 or CLCN7. Any of the above-described TMEM192-, SLC12A9- or CLCN7-inhibiting systems, methods or agents may be employed for this purpose. In one aspect of this embodiment, the patient is an organ transplant recipient, is in need of immunosuppression, is a stent recipient, has or suffers from or is at risk of developing arterial stenosis, or has or suffers from cancer, in particular a cancer for which treatment with rapamycin is recommended or approved by a regulatory agency, a cancer subtype that is characterized by genetic perturbations leading to increased activity through signaling pathways impinging upon or modulated by mTORC1, or a cancer subtype where autophagy is upregulated. In another related aspect of this embodiment, the patient has or suffers from obesity, a disease caused by metabolic dysfunction (e.g., type 2 diabetes, metabolic syndrome, beta-cell dysfunction), a cardiomyopathy, an auto-immune disease (e.g. psoriasis, lupus), a neurodegenerative diseases (e.g. Alzheimer's disease, Huntington's disease, Parkinson's disease), neurogenic disorders associated with aberrant mTORC1 activation (e.g., tuberous sclerosis complex, neurofibromatosis, fragile X syndrome, PTEN-associated conditions, autism and autism spectrum disorders, epilepsy and seizures), a genetic diseases that result in mitochondrial dysfunction (e.g. Leigh's Syndrome, Friedreich Ataxia), or a genetic diseases that result in hyperactive mTORC1 signaling (e.g. Tuberous Sclerosis, Lymphangioleiomyomatosis). In an alternate aspect of this embodiment, the patient is suffering from a disease or condition selected from a metabolic disease (e.g., type 2 diabetes, obesity, non-alcoholic steatohepatitis (NASH), and hyperlipidemia), a neurodegenerative disease (e.g., Alzheimer's disease, Parkinson's Disease, Huntington's Disease, and amyotrophic lateral sclerosis), an autoimmune disease (e.g., psoriasis, rheumatoid arthritis, multiple sclerosis, systemic lupus erythematosus, gout, allergic rhinitis, Crohn's Disease, and ulcerative colitis), rare and mitochondrial disease (e.g., Leigh's Syndrome, Friedreich's Ataxia Cardiomyopathy, Leber's Hereditary Optic Neuropathy, lymphangioleiomyomatosis, tuberous sclerosis, Pompe Disease (Glycogen storage disease II), and lysosomal storage diseases), cardiovascular disease (e.g., cardiomyopathy, heart failure, ischemic heart disease (atherosclerotic disease), ischemic stroke, and pulmonary arterial hypertension), renal disease (e.g., diabetic nephropathy, polycystic kidney disease, and acute kidney injury), neuropsychiatric disease (e.g., epilepsy, autism spectrum disorder, and depressive disorder), and ontological disease (e.g., renal cell carcinoma, solid tumors, hematological cancers.

In another embodiment, the invention provides a method of identifying modulators of SLC38A9 comprising the steps of: a) contacting a test compound with a polypeptide comprising SLC38A9.1, or a fragment or mutant of SLC38A9.1, wherein the polypeptide possesses an activity or characteristic of SLC38A9.1; b) measuring the activity or characteristic of SLC38A9.1 in the presence of the test compound; and c) comparing the measured activity or characteristic with the same activity or characteristic in the absence of the test compound, thereby determining whether the test compound is a modulator of SLC38A9.

These methods may employ cellular systems where the SLC38A9 or a fragment or mutant thereof is engineered to reside at the plasma membrane (e.g., by fusion of the N-terminus to a plasma membrane signal sequence, e.g., the last 25 amino acids of H-Ras—(QHKLRKLNPPDES-GPGCMSCKCVLS; SEQ ID NO:5); non-mammalian cellular systems that are engineered to express the SLC38A9 or a fragment or mutant thereof at the plasma membrane (e.g., *Xenopus oocytes*); in vitro systems where the SLC38A9 or a fragment or mutant thereof is attached to a solid support; and in vitro systems where the SLC38A9 or a fragment or mutant thereof is free in solution.

Activities or characteristics to be measured in these methods include uptake of labelled (e.g., radiolabelled, fluorescently labelled) amino acids (e.g., arginine, histidine or lysine) in cellular systems, uptake of sodium in cellular systems, changes in membrane potential across a membrane in cellular systems, binding of amino acids to SLC38A9 or a fragment or mutant thereof in in vitro systems; binding of test compound to SLC38A9 or a fragment or mutant thereof in in vitro systems; changes in the ability of SLC38A9 or a fragment or mutant thereof to bind to Ragulator in both in vivo and in vitro systems; and changes in one or more activities of mTORC1 (e.g., change in phosphorylation state of S6K1).

The measurement of these activities may be achieved by scintillation counting for radiolabelled amino acids; flow cytometry, fluorescence microplate or with a spectrofluorophotometer for fluorescent amino acids and to measure changes in membrane potential (e.g., dyes that change fluorescence in response to changes in membrane potential, e.g., FLIPR dyes (Molecular Devices); patch clamping for measuring electrical currents across a membrane; solid phase surface plasmon resonance to measure changes in amino acid binding or direct binding of test compound; and mass spectrometry to measure changes in amino acid binding or direct binding of test compound.

The choice of a fragment or mutant of SLC38A9.1 to be used in such methods will be dependent upon the activity to be measured. Fragments lacking amino acids 1-110, as well as SLC38A9 isoform 2 and 4, do not interact with Ragulator and therefore should be avoided when the activity to be measured is dependent upon Ragulator interaction. However, fragments lacking amino acid 1-110 do still bind to and transport amino acids and therefore can be employed in assays that measure amino acid binding and transport either directly or indirectly. In one embodiment, intact SLC38A9.1 or SLC38A9.1 Δ110 is used in assays that measure amino acid binding and transport either directly or indirectly.

The polypeptide comprising SLC38A9.1, or a fragment or mutant of SLC38A9, may also include other amino acid sequences that impart additional desirable properties to the polypeptide that are useful in these methods. In some embodiments, the polypeptide further comprises a tag at the N- or C-terminus that aids in the recombinant production of the polypeptide and/or isolation of the polypeptide. Such tags include histidine or poly-histidine tags, epitope tags (e.g., FLAG or HA polypeptide fusions) or ligand tags (e.g., biotin), which may be covalently bound directly to SLC38A9.1, or a fragment or mutant thereof or through a linker. In some embodiments, the polypeptide further comprises a signal sequence that targets the polypeptide to the plasma membrane (e.g., the last 25 amino acids of H-Ras—QHKLRKLNPPDESGPGCMSCKCVLS; SEQ ID NO:5). In some embodiments, the polypeptide further comprises a fluorescent or bioluminescent tag or polypeptide sequence (e.g., fusion to a green fluorescent protein, yellow fluorescence protein, red fluorescent protein, or luciferase).

Specific examples of these methods are set forth below in the Examples.

It is to be understood that the inventions disclosed herein are not limited in their application to the details set forth in the description or as exemplified. The inventions encompass other embodiments and are capable of being practiced or carried out in various ways. Also, it is to be understood that the phraseology and terminology employed herein is for the purpose of description and should not be regarded as limiting.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1. SLC38A9 Interacts with Ragulator

It remains unclear how the presence or absence of amino acids triggers the complex network of lysosomal proteins that mediate the translocation and activation of mTORC1. One hypothesis was that a putative amino acid sensor would directly interact with one of the lysosomal complexes involved in signaling to mTORC1. To test this hypothesis, we initially focused on the Ragulator complex and performed immunoprecipitation from HEK-293T cells stably expressing various FLAG-tagged proteins under conditions that would preserve protein-protein interactions.

The cDNAs for all human SLC38A9 isoforms, both native and codon-optimized, were gene-synthesized by GenScript. The cDNAs were amplified by PCR and the products were subcloned into Sal I and Not I sites of HA-pRK5 and FLAG-pRK5. The cDNAs were mutagenized using the QuikChange II kit (Agilent) with oligonucleotides obtained from Integrated DNA Technologies. All constructs were verified by DNA sequencing.

FLAG-tagged SLC38A9 isoforms and SLC38A9 N-terminal 1-119 were amplified by PCR and cloned into the Sal I and EcoR I sites of pLJM60 or into the Pac I and EcoR I sites of pMXs. After sequence verification, these plasmids were used, as described below, in cDNA transfections or to produce lentiviruses needed to generate cell lines stably expressing the proteins.

HEK-293T cells were cultured in DMEM supplemented with 10% inactivated fetal bovine serum, penicillin (100 IU/mL), and streptomycin (100 μg/mL) and maintained at 37° C. and 5% $CO_2$. Two million HEK-293T cells were plated in 10 cm culture dishes. Twenty-four hours later, cells were transfected with the pRK5-based cDNA expression plasmids indicated in the figures in the following amounts: 500 ng FLAG-metap2; 50 ng FLAG-LAMP1; 100 ng FLAG-RagB and 100 ng HA-RagC; 300 ng FLAG-SLC38A9.1; 600 ng FLAG-SLC38A9.1 Δ110; 200 ng FLAG-SLC38A9.4; 400 ng FLAG-N-terminal 119 fragment of SLC38A9.1; 200 ng FLAG-RagC; 200 ng FLAG-RagC S75N; 200 ng FLAG-RagC Q120L; 400 ng HAGST-RagB; 400 ng HAGST-RagB T54N; 400 ng HAGST-RagB Q99L.

Transfection mixes were taken up to a total of 5 μg of DNA using empty pRK5. HEK-293T cells stably expressing FLAG-tagged proteins were rinsed once with ice-cold PBS and lysed in ice-cold lysis buffer (40 mM HEPES pH 7.4, 1% Triton X-100, 10 mM β-glycerol phosphate, 10 mM pyrophosphate, 2.5 mM MgC12 and 1 tablet of EDTA-free protease inhibitor (Roche) per 25 ml buffer). The soluble fractions from cell lysates were isolated by centrifugation at 13,000 rpm for 10 min in a microcentrifuge. For immunoprecipitates 30 μL of a 50% slurry of anti-FLAG affinity gel (Sigma) were added to each lysate and incubated with rotation for 2-3 hr. at 4° C. Immunoprecipitates were washed three times with lysis buffer containing 500 mM NaCl. Immunoprecipitated proteins were denatured by the addition of 50 μL of sample buffer and incubation at RT for 30 min. It is critical that the samples containing SLC38A9 are neither boiled nor frozen prior to resolution by SDS-PAGE and analysis by immunoblotting. A similar protocol was employed when preparing samples for mass spectrometry.

Immunoprecipitates from 30 million HEK-293T cells stably expressing FLAG-metap2, FLAG-p18, FLAG-p14, FLAG-HBXIP, FLAG-c7orf59, and FLAG-RagB were prepared as described below. Proteins were eluted with the FLAG peptide (sequence DYKDDDDK) from the anti-FLAG affinity beads, resolved on 4-12% NuPage® gels (Invitrogen), and stained with SimplyBlue™ SafeStain (Invitrogen). Each gel lane was sliced into 10-12 pieces and proteins in each gel slice digested overnight with trypsin. The resulting digests were then subjected to liquid chromatography followed by tandem mass spectrometry (LC-MS-MS) for protein identification. SLC38A9 (NCBI Gene ID: 153129), a member of the amino acid/sodium family of co-transporters, was present in all Ragulator component-specific immunoprecipitations, as well as to some extent in immunoprecipitations of RagB, but not in immunoprecipitations of control protein Metap2.

Figure 6A:
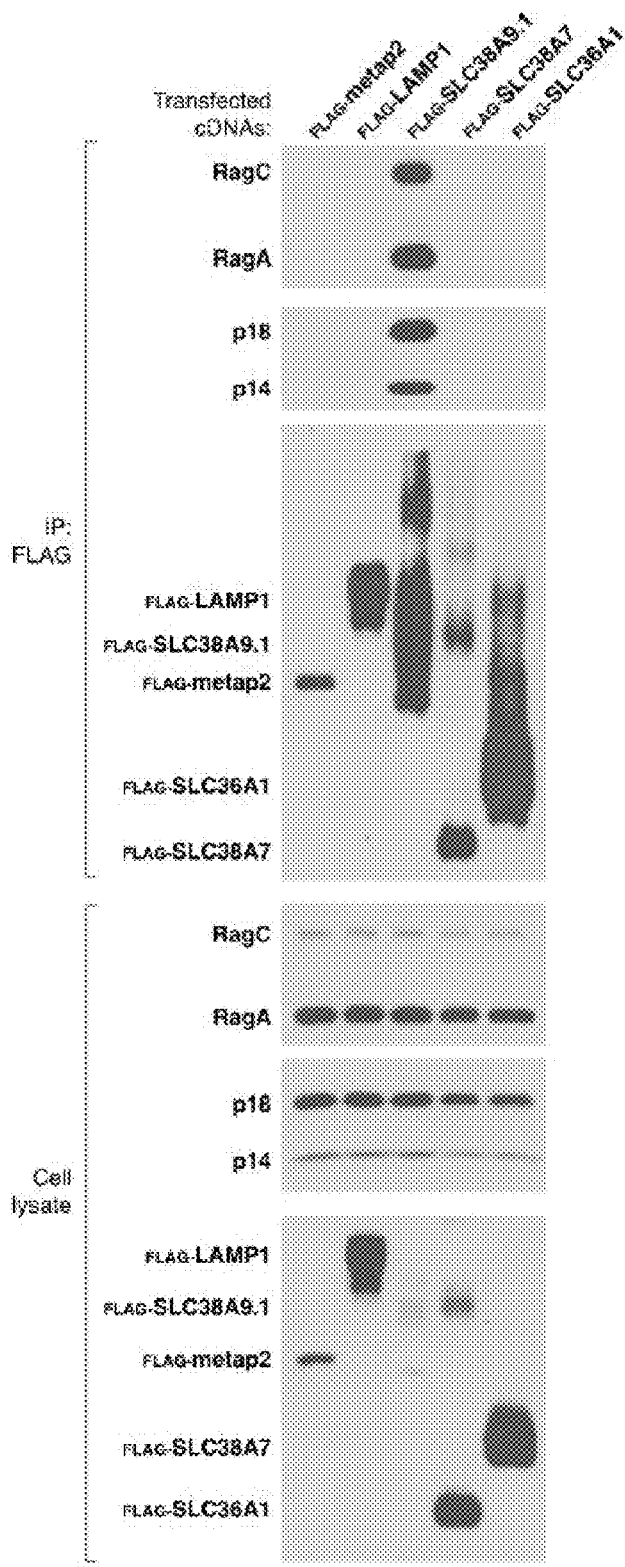
FIGS. 6A-6C depict immunoblots demonstrating that Ragulator and the Rag GTPases bind specifically to the N-terminal domain of SLC38A9.1 in HEK-293T cells expression various FLAG-tagged proteins.

To confirm the LC-MS-MS data, we transfected HEK-293T cells with FLAG-tagged constructs of SLC38A9.1 using the protocol described above and were able to immunoprecipitate endogenous Ragulator proteins (as detected by its p14 and p18 components) as well as RagA and RagC. Other FLAG-tagged lysosomal membrane proteins LAMP1, SC36A1 and SLC38A7 did not immunoprecipitate any of p14, p18, RagA or RagC (FIG. 1D and FIG. 6A). We were also able to demonstrate binding between recombinant epitope tagged SLC38A9 and co-expressed epitope tagged Ragulator proteins.

Figure 6B:
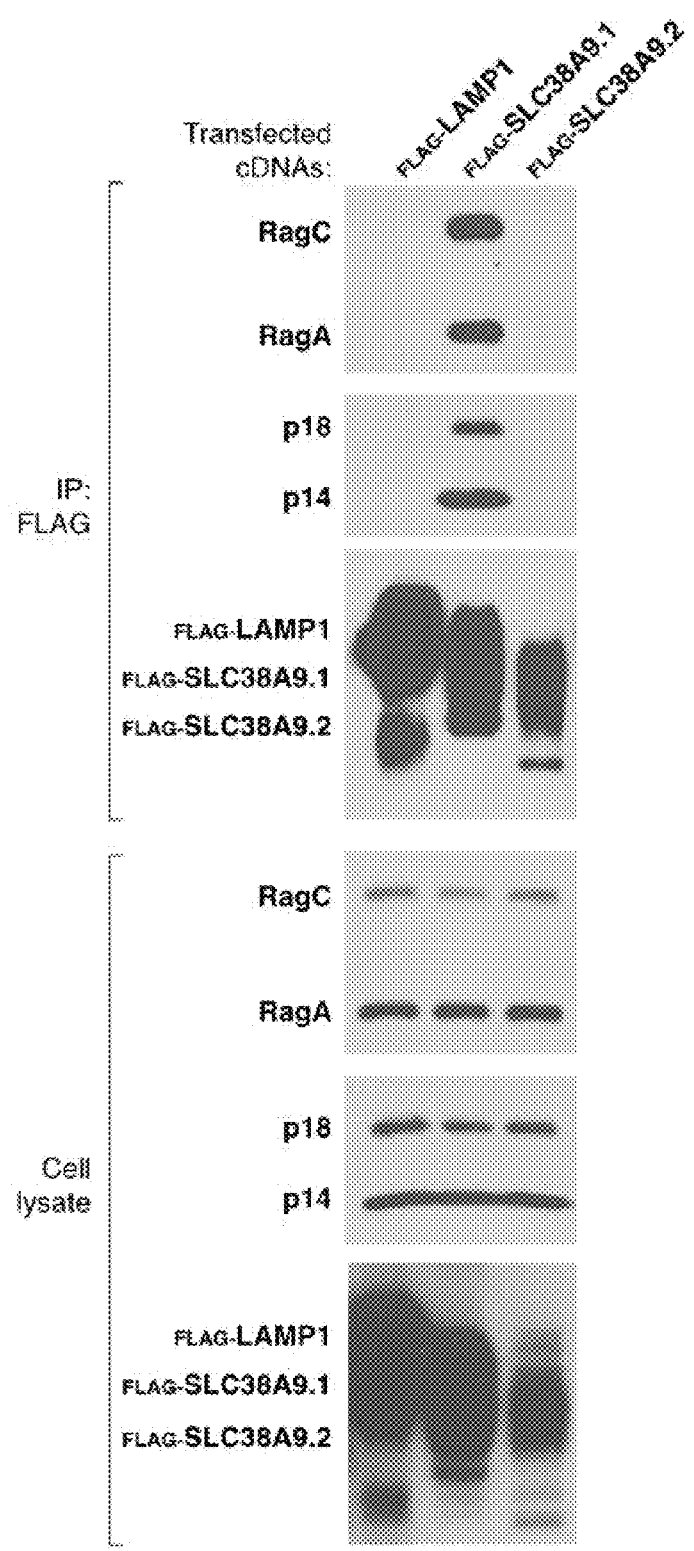

Having confirmed the mass-spectrometry data indicating that SLC38A9 interacts with Ragulator, we began to determine which region of SLC38A9 is responsible for its interaction with Ragulator. There are 4 distinct isoforms annotated by NCBI for SLC38A9; isoform 1 (SEQ ID NO:1) is the full-length protein; isoform 2 is missing the first 63 amino acids from the N-terminus of SEQ ID NO:1; isoform 3 has a shorter, modified N-terminus and truncated C-terminus; and isoform 4 is missing the entire N-terminus region that precedes the first transmembrane domain (AA1-119). We expressed isoforms 1, 2 and 4 in HEK-293T cells, as well as a mutant of SLC38A9.1 lacking its first 110 amino acids (SLC38A9.1 Δ110) and found that isoform 1 strongly binds to Ragulator, whereas neither isoforms 2, 4 or SLC38A9.1 Δ110 were able to immunoprecipitate endogenous or co-transfected Ragulator proteins (FIGS. 6, B and C).

Figure 6C:
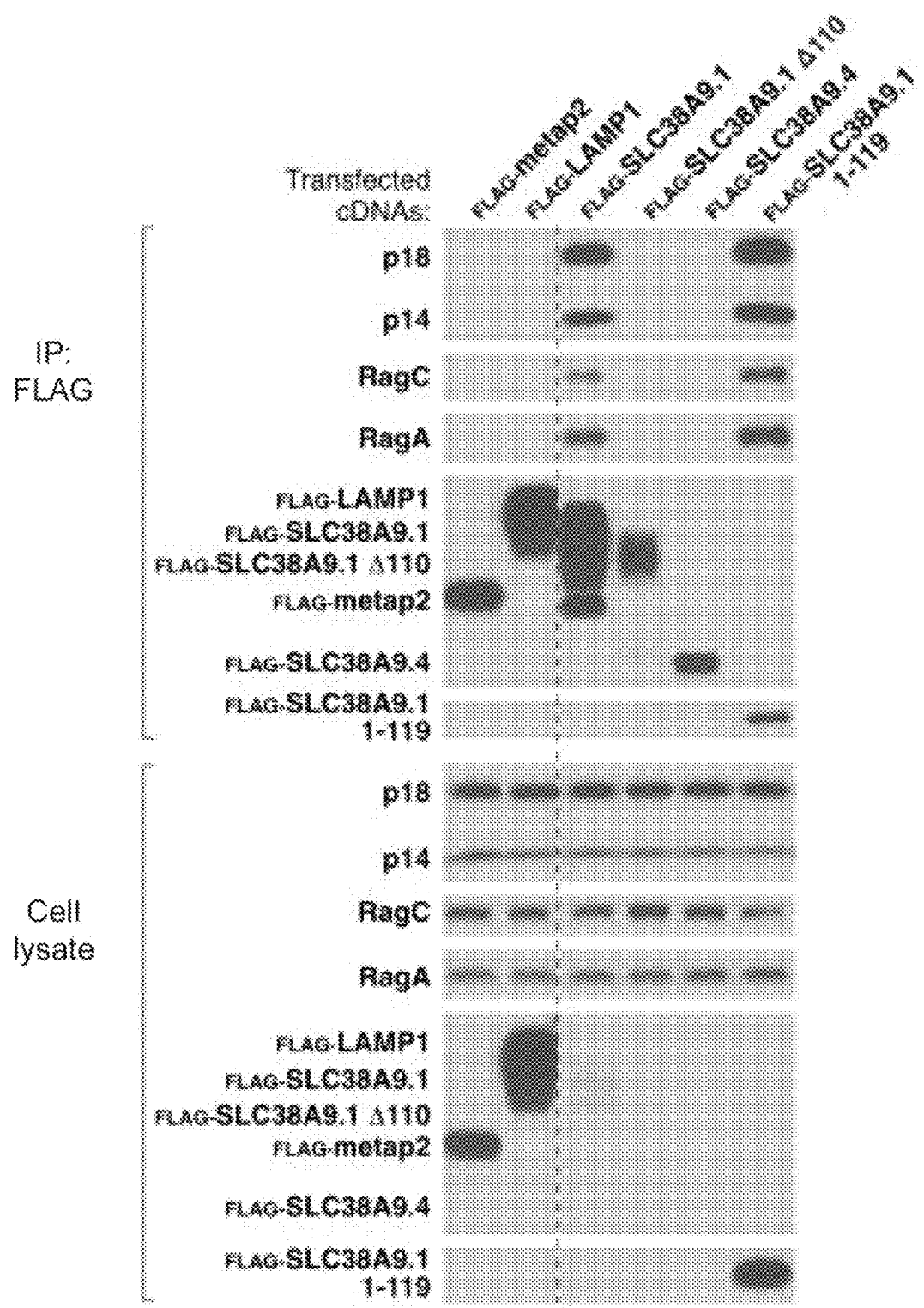

Given that isoform 4 was unable to precipitate Ragulator components, we focused on the N-terminus (AA1-119) as likely responsible for mediating the interaction between SLC38A9 and Ragulator. We developed an N-terminal FLAG-tagged construct consisting of just the N-terminus of SLC38A9, amino acid residues 1-119, and found that it was necessary and sufficient to immunoprecipitate Ragulator (FIG. 1A and FIG. 6C). We looked at conserved residues between humans, zebrafish and C. elegans and found that amino acids 59-90 are strongly conserved. Substituting each residue with alanine in the AA1-119 construct identified the following mutations as disrupting the binding of the N-terminal region of SLC38A9 with Ragulator: I68A, Y71A, L74A, P85A, V89A, P90A. Alanine substitutions within this region that did not disrupt the interaction include D59A, H60A, S62A, S72A, R73A, P77A, D86A, and V88A. We concluded that I68, Y71, L74, P85, and P90 were required for the Ragulator-SLC38A9.1 interaction (FIG. 1E).

Given its homology to other amino acid transporters, we performed immunoprecipitation assays between full-length SLC38A9 and Ragulator proteins under both amino acid replete and amino acid deficient culture conditions. We found the interaction between SLC38A9 and Ragulator proteins to be modulated by amino acid conditions similar to what is observed between Ragulator and Rag proteins. When this assay was repeated with just the N-terminus of SLC38A9 (amino acids 1-119 of SEQ ID NO:1), we did not observe any changes in response to amino acid levels. As a result, we believe that the interaction between SCL38A9 and Ragulator to be modified by amino acids, and that this modulation is important for its function as a regulator of mTORC1 signaling in response to amino acids. It is likely that the transmembrane region of SLC38A9 is needed to mediate the response to amino acids.

Figure 1C:
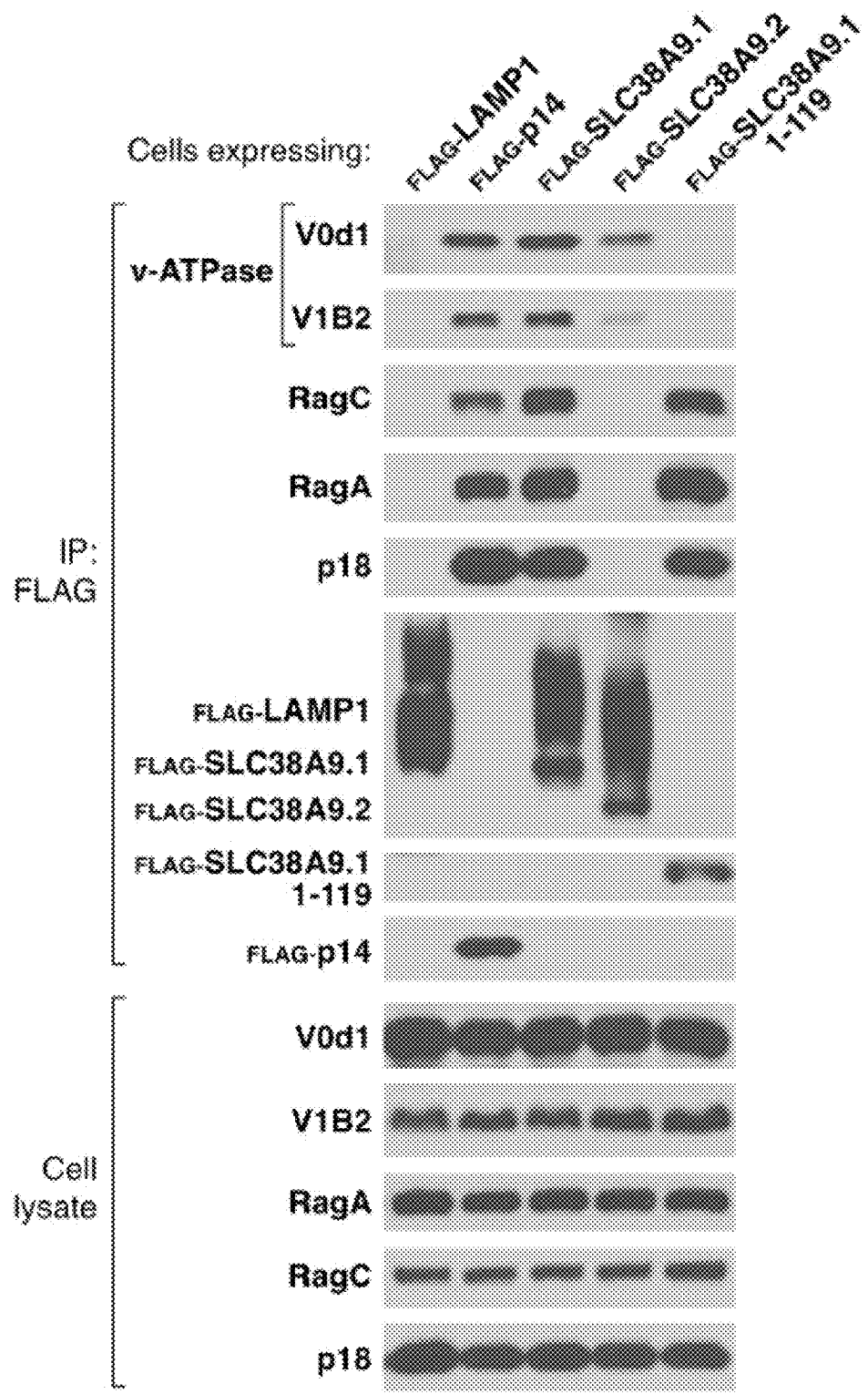

The v-ATPase and its activity are necessary for amino acid sensing by the mTORC1 pathway and, like SLC38A9.1, it co-immunoprecipitated with stably expressed FLAG-tagged Ragulator. This indicated the existence of a supercomplex of stably expressed SLC38A9.1, but not LAMP1, associated with endogenous components of the v-ATPase in addition to Ragulator and the Rag GTPases (FIG. 1C). Although SLC38A9.2 does not interact with Ragulator, it did co-immunoprecipitate the v-ATPase, albeit at lesser amounts than SLC38A9.1 (FIG. 1C). This suggests that the interaction between SLC38A9.1 and the v-ATPase is not mediated through Ragulator but directly or indirectly through the region of SLC38A9.1 that contains its transmembrane domains. Concordant with this interpretation, the N-terminal domain of SLC38A9.1, which interacts strongly with Ragulator, did not co-immunoprecipitate the vATPase (IG. 1C).

Example 2. SLC38A9 is Localized to the Lysosomal Membrane

Given its strong interaction with Ragulator and its homology to other SLC38 family members that contain canonical 5+5 transmembrane structures, we predicted that SLC38A9 is localized to the lysosomal membrane.

HEK-293T cells were plated on fibronectin-coated glass coverslips in 6-well tissue culture dishes, at 300,000 cells/well. 12-16 hours later, the slides were rinsed with PBS once and fixed and permeabilized in one step with ice-cold 100% methanol (for SLC38A9 detection) at −20° C. for 15 min. After rinsing twice with PBS, the slides were incubated with primary antibody (FLAG CST 1:300, LAMP2 1:400) in 5% normal donkey serum for 1 hr. at room temperature, rinsed four times with PBS, incubated with secondary antibodies produced in donkey (diluted 1:400 in 5% normal donkey serum) for 45 min at room temperature in the dark, and washed four times with PBS. Slides were mounted on glass coverslips using Vectashield with DAPI (Vector Laboratories) and imaged on a spinning disk confocal system (Perkin Elmer).

Figure 2A:
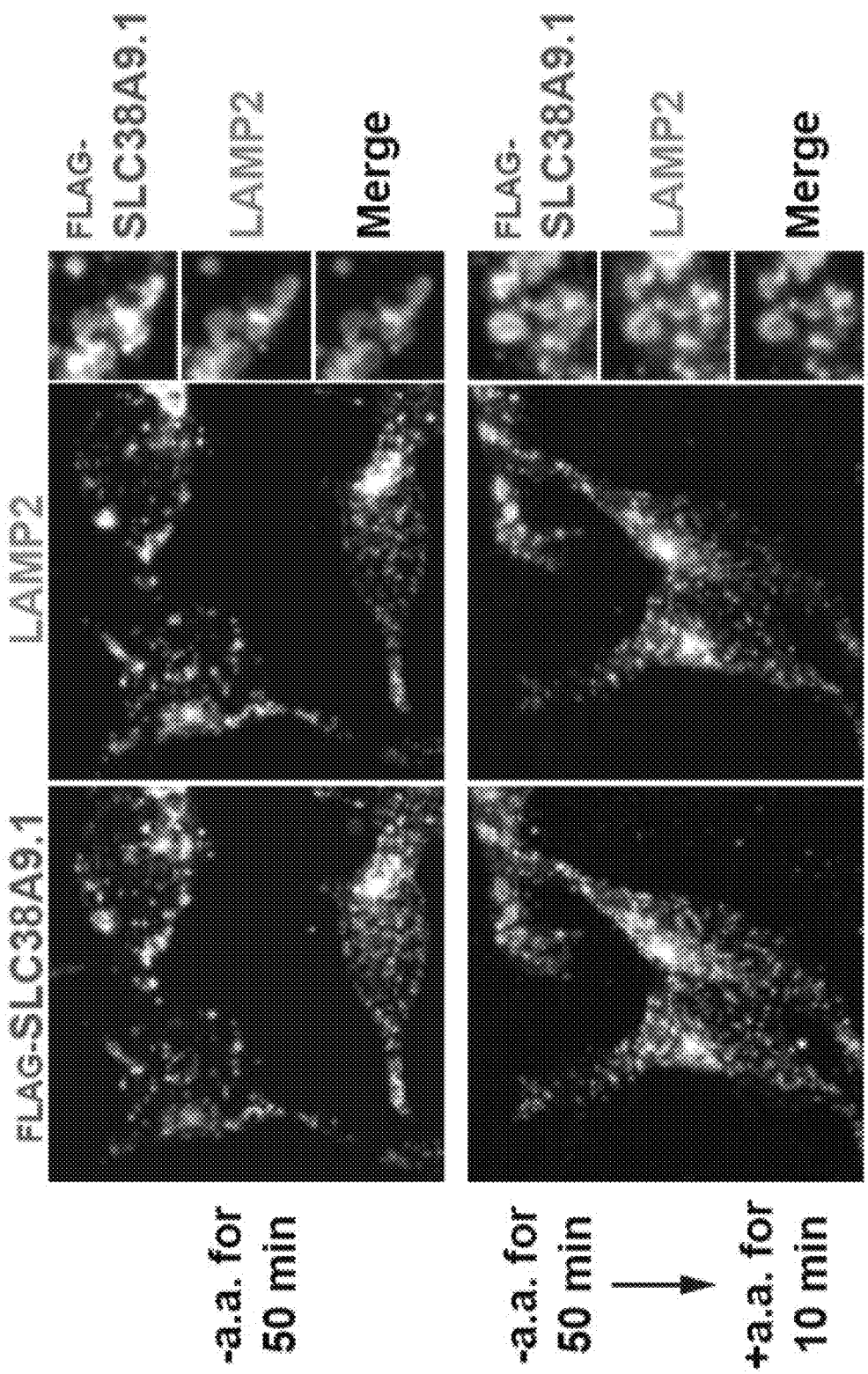
FIGS. 2A-2B depict the effects of amino acids on localization of SLC38A9.1 and the lysosomal membrane protein LAMP-2, as well as the effects of amino acids on mTORC1 and SLC38A9 production.

Immunofluorescence imaging determined that all epitope tagged isoforms of SLC38A9 co-localized with lamp2 indicating that SLC38A9 is a lysosomal membrane protein (FIG. 2A and FIGS. 7, A and B). We also stained for SLC38A9 and lamp2 in two different mouse embryonic fibroblasts deficient for a Ragulator component, and SLC38A9 continued to be localized to the lysosome indicating that it does not require Ragulator for its lysosomal localization. Consistent with this finding, localizing Ragulator to the cytoplasm by removing its lipid anchor does not alter the lysosomal localization of SLC38A9, nor does the mutant Ragulator interact with SLC38A9.1 (FIG. 7C). These data indicate that SLC38A9 is a lysosomal membrane protein that does not require its N-terminus or Ragulator for localization to the lysosome.

Lentiviruses encoding shRNAs were prepared and transduced into HEK-293T cells as described follows. Lentiviruses were produced by co-transfection of the pLJM1/pLJM60 lentiviral transfer vector with the VSV-G envelope and CMV AVPR packaging plasmids into viral HEK-293T cells 4 using the XTremeGene 9 transfection reagent (Roche). For infection of HeLa cells, LN229 cells, and MEFs, retroviruses were produced by co-transfection of the pMXs retroviral transfer vector with the VSV-G envelope and Gag/Pol packaging plasmids into viral HEK-293T cells. The media was changed 24 hours post-transfection to DME supplemented with 30% IFS. The virus-containing supernatants were collected 48 hours after transfection and passed through a 0.45 μm filter to eliminate cells. Target cells in 6-well tissue culture plates were infected in media containing 8 μg/mL polybrene and spin infections were performed by centrifugation at 2,200 rpm for 1 hour. 24 hours after infection, the virus was removed and the cells selected with the appropriate antibiotic.

The sequences of control shRNAs and those targeting human SLC38A9, which were obtained from The RNAi Consortium 3 (TRC3), are the following (5' to 3'):

```
SLC38A9 #1:
                        (SEQ ID NO: 6)
GCCTTGACAACAGTTCTATAT;
(TRCN0000151238)

SLC38A9 #2:
                        (SEQ ID NO: 7)
CCTCTACTGTTTGGGACAGTA;
(TRCN0000156474)

GFP:
                        (SEQ ID NO: 8)
TGCCCGACAACCACTACCTGA.
(TRCN0000072186)
```

For siRNA-based experiments, 200,000 HEK-293T cells were plated in a 6-well plate. 24 hours later, cells were transfected using DharmaFECT 1 (Dharmacon) with 250 nM of a pool of siRNAs (Dharmaeon) targeting SLC38A9 or a non-targeting pool. 48 hours post-transfection, cells were transfected again but this time with double the amount of siRNAs. 24 hours following the second transfection, cells were rinsed with ice-cold PBS, lysed, and subjected to immunoblotting as described above. The following siRNAs were used: Non-targeting: ON-TARGETplus Non-targeting Pool (D-001810-10-05) SLC38A9: SMARTpool: ON-TARGETplus SLC38A9 (L-007337-02-0005)

Figure 2B:
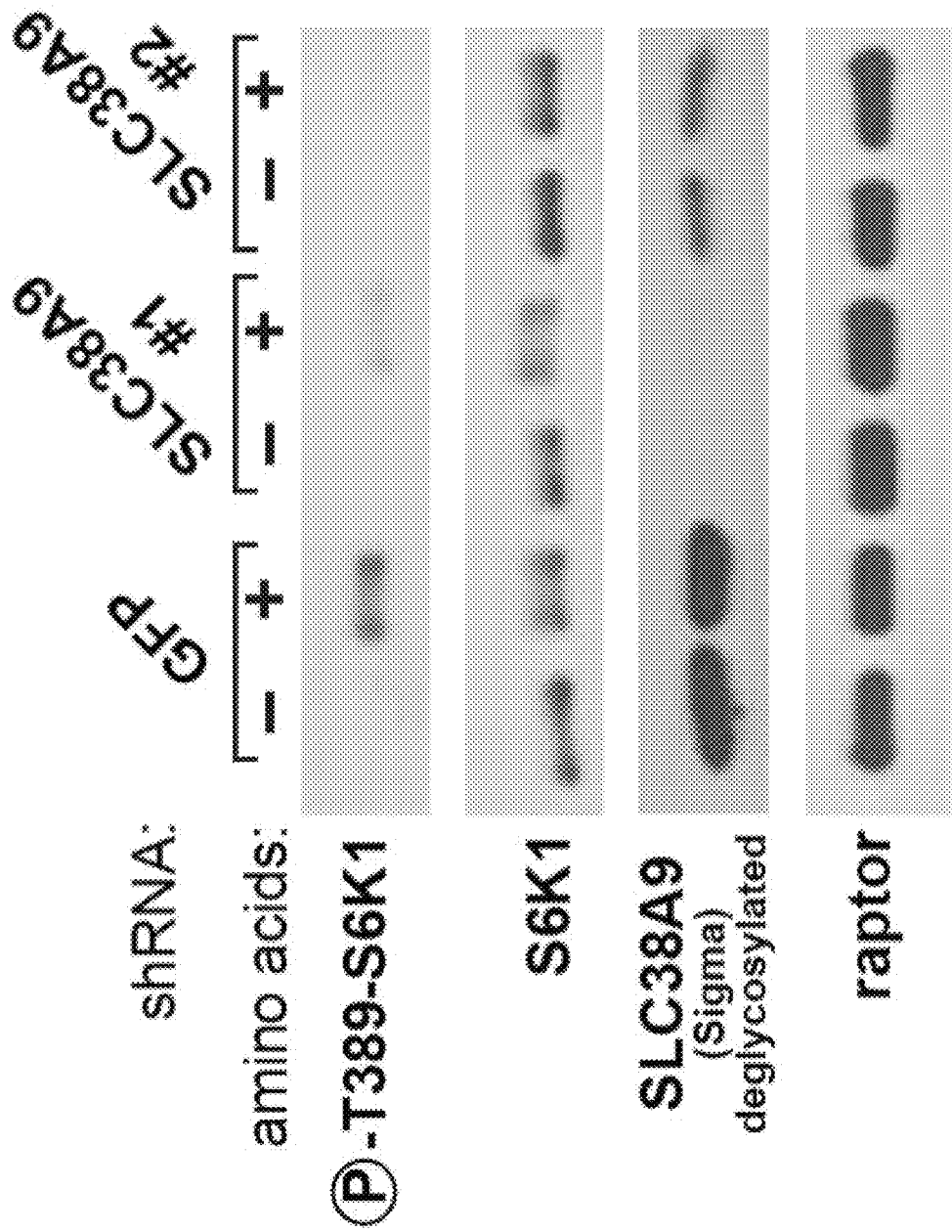
Figure 7A:
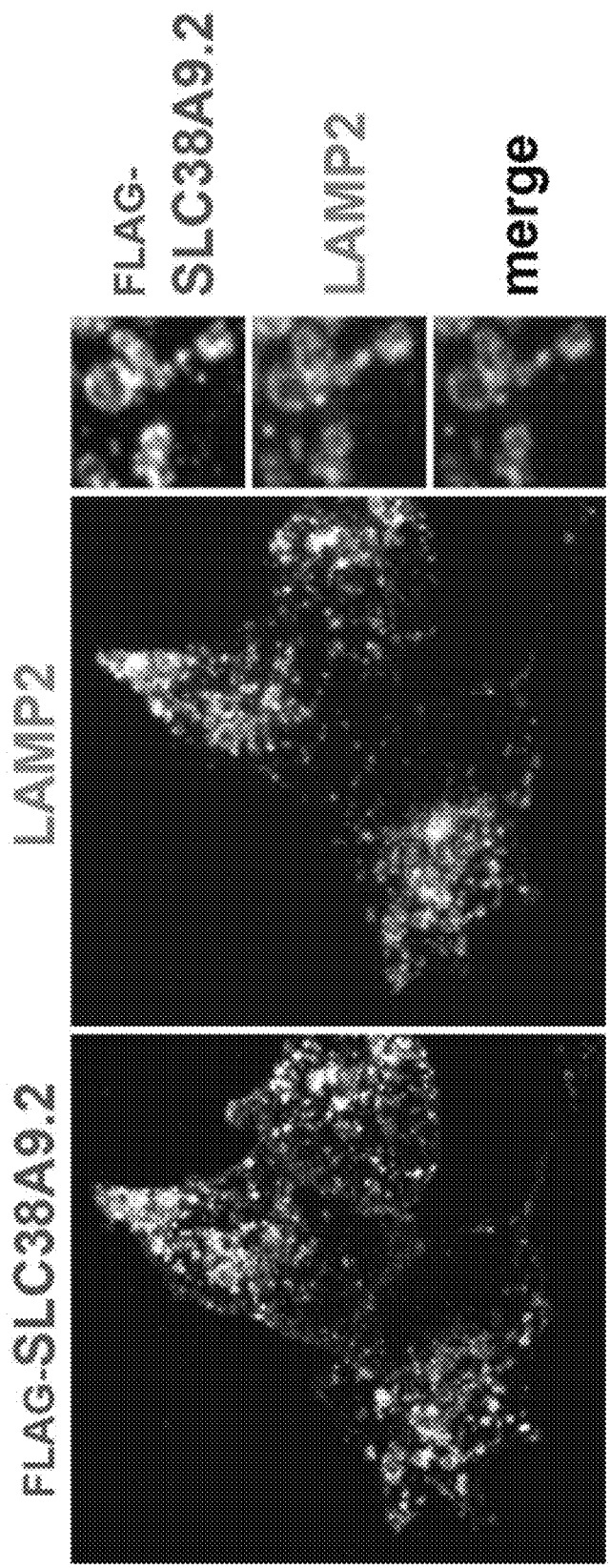
FIGS. 7A-7D depict the results of immunostain and immunoblot experiments performed.
Figure 7B:
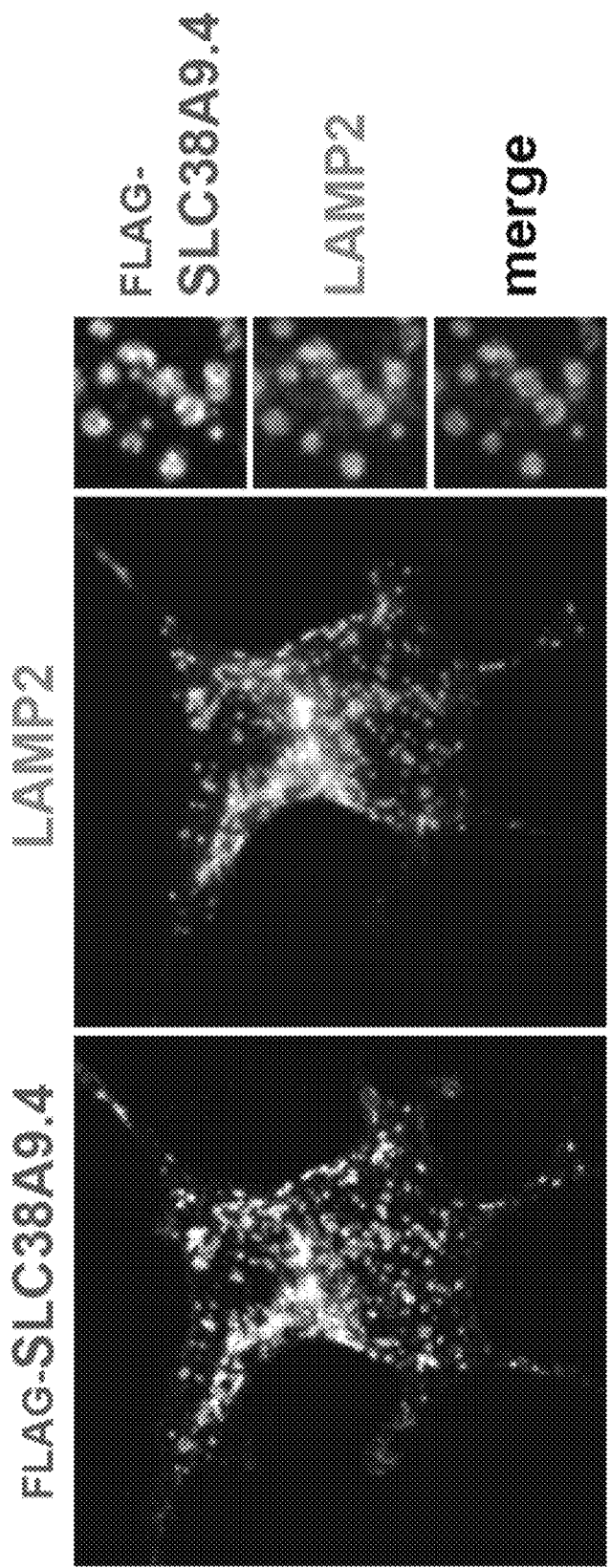
Figure 7C:
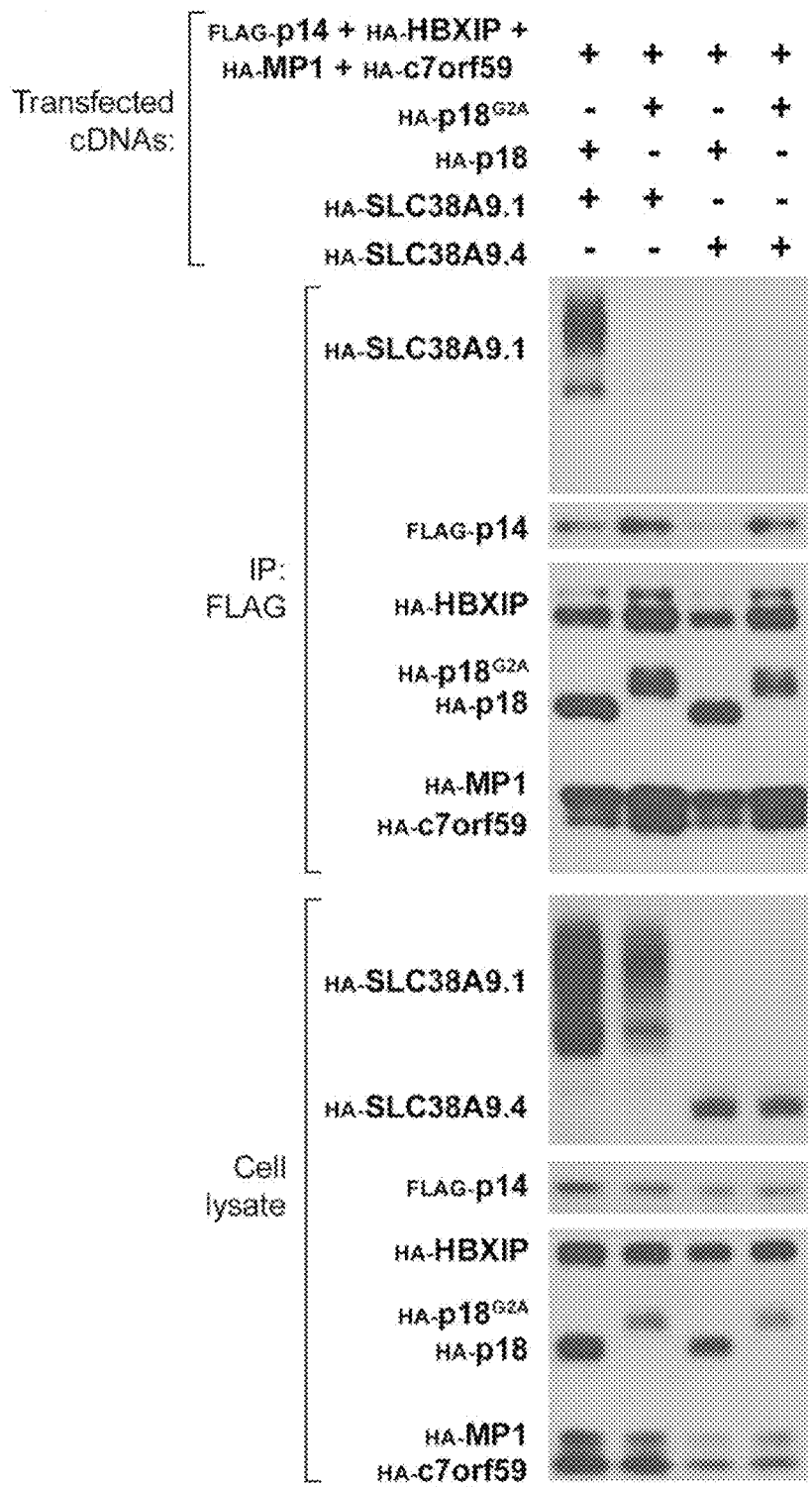
Figure 7D:
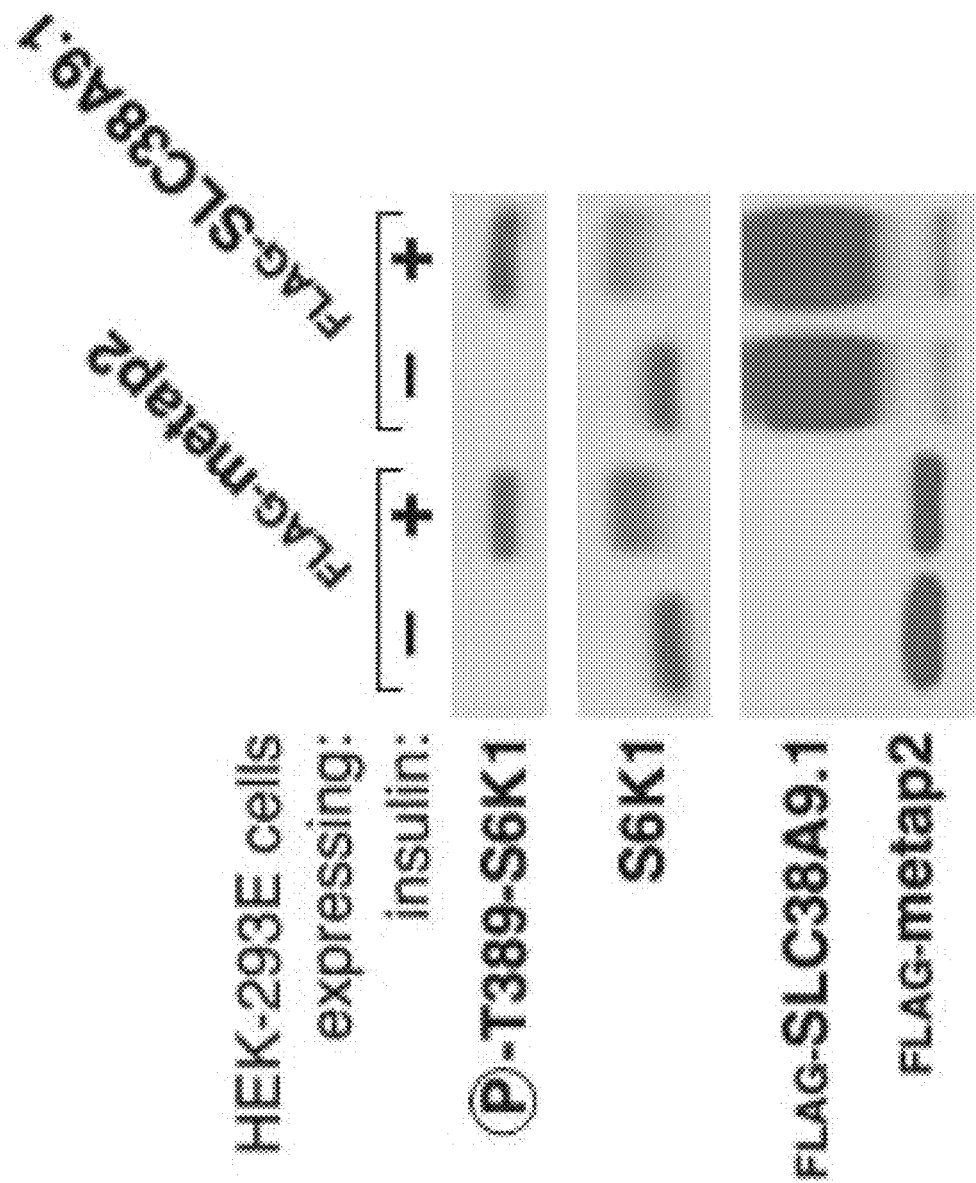

ShRNA- or siRNA-mediated depletion of SLC38A9 in HEK-293T cells suppressed activation of mTORC1 by amino acids, as detected by the phosphorylation of its established substrate ribosomal protein S6 Kinase 1 (S6K1) (FIG. 2B and FIG. 7D). Thus, like the five known subunits of Ragulator, SLC38A9.1 is a positive component of the mTORC1 pathway. Without being bound by theory we believe that SLC38A9.1 is a lysosomal membrane protein that interacts with Ragulator and the Rag GTPases through its N-terminal 119 amino acids ('Ragulator-binding domain') and is required for mTORC1 activation.

Example 3. SLC38A9 Overexpression Activates mTORCL

Having established that SCL38A9 strongly interacts with Ragulator at the lysosome, we wished to understand the function of SLC38A9 in regulating mTORC1 activity. Given that the SLC38 family is involved in transport of amino acids, we tested whether overexpression of SLC38A9 modulated mTORC1 signaling in response to amino acids. In wild-type cells in culture, amino acid withdrawal results in inhibition of mTORC1 signaling.

One million HEK-293T cells were plated in 10 cm culture dishes. 24 hours later, cells were transfected with the pRK5-based cDNA expression plasmids indicated in the figures in the following amounts: 500 ng HA-metap2; 50 ng HA-LAMP1; 200 ng HA-SLC38A9.1; 500 ng HA-SLC38A9.1 Δ110; 200 ng HASLC38A9.4; 100 ng HA-RagB T54N and 100 ng HA-RagC Q120L; 2 ng FLAG-S6K1. 72 hours post-transfection, cells were washed once prior to 50-min incubation with amino acid-free RPMI. Cells were stimulated with vehicle or amino acids (to a final concentration equivalent to RPMI) prior to harvest.

Figure 3A:
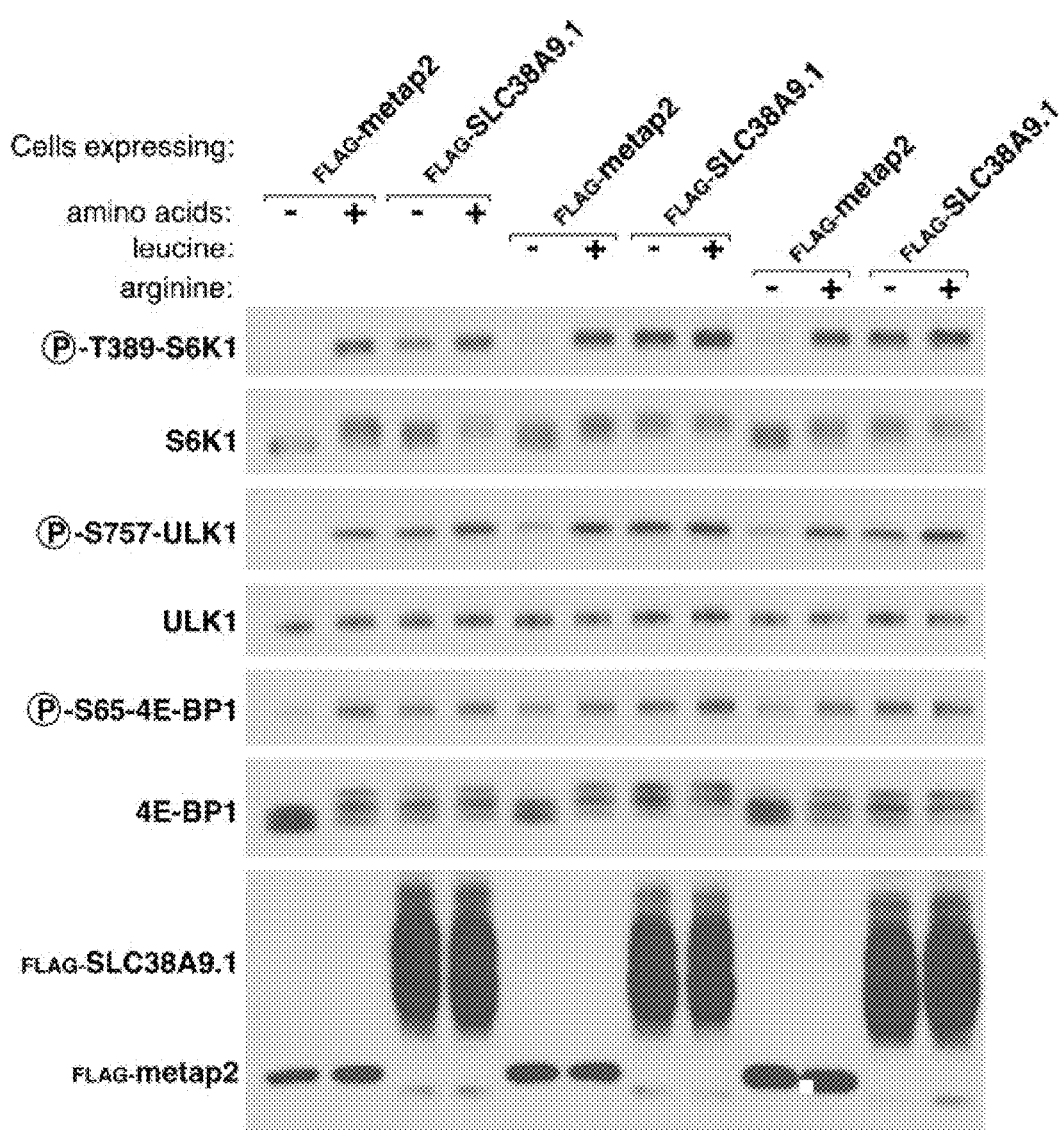
FIGS. 3A-3D depict immunoblots demonstrating the effect of amino acids on various mTORC1 components in HEK-293T cells transduced with lentiviruses encoding the indicated FLAG-tagged proteins.
Figure 3B:
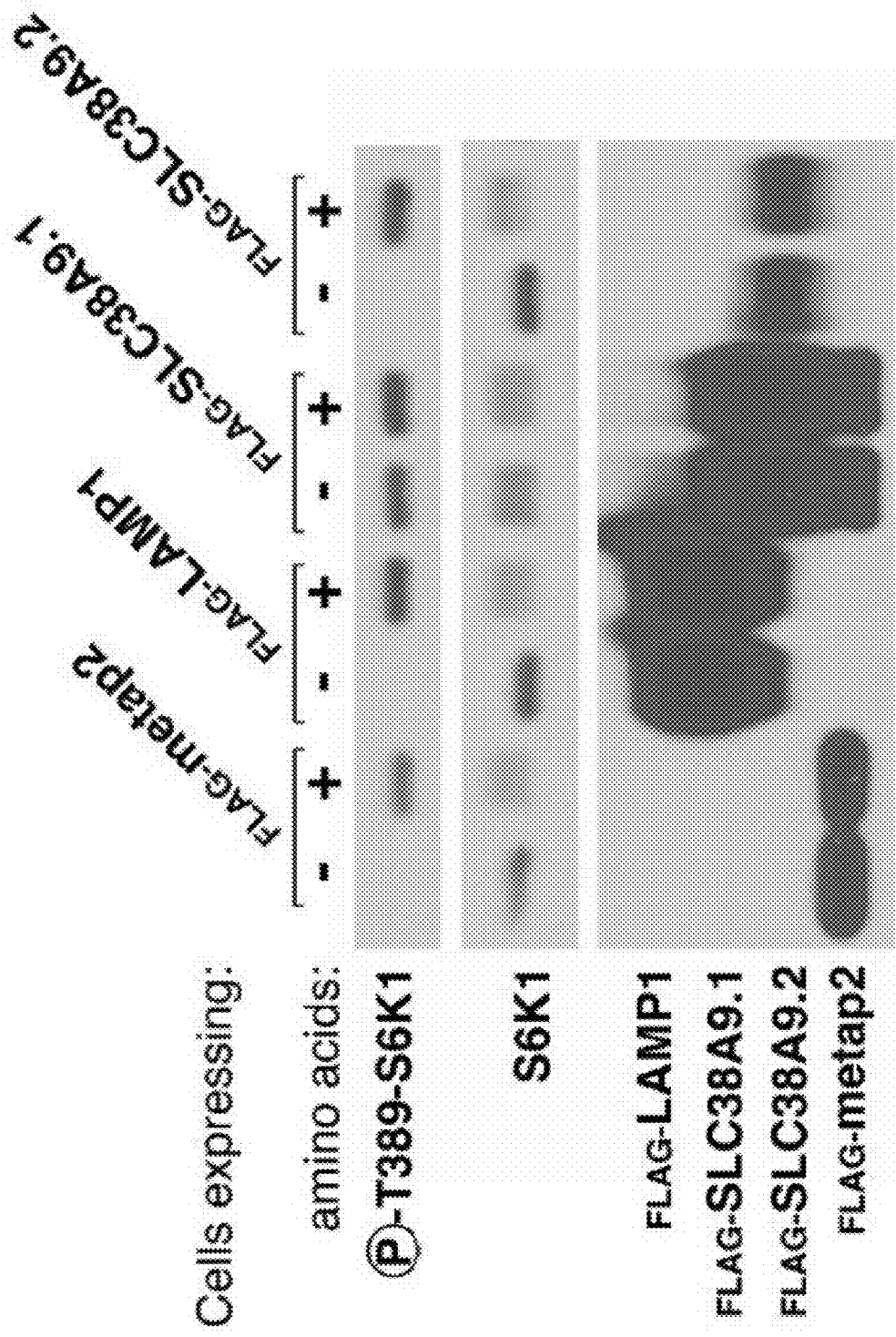
Figure 3C:
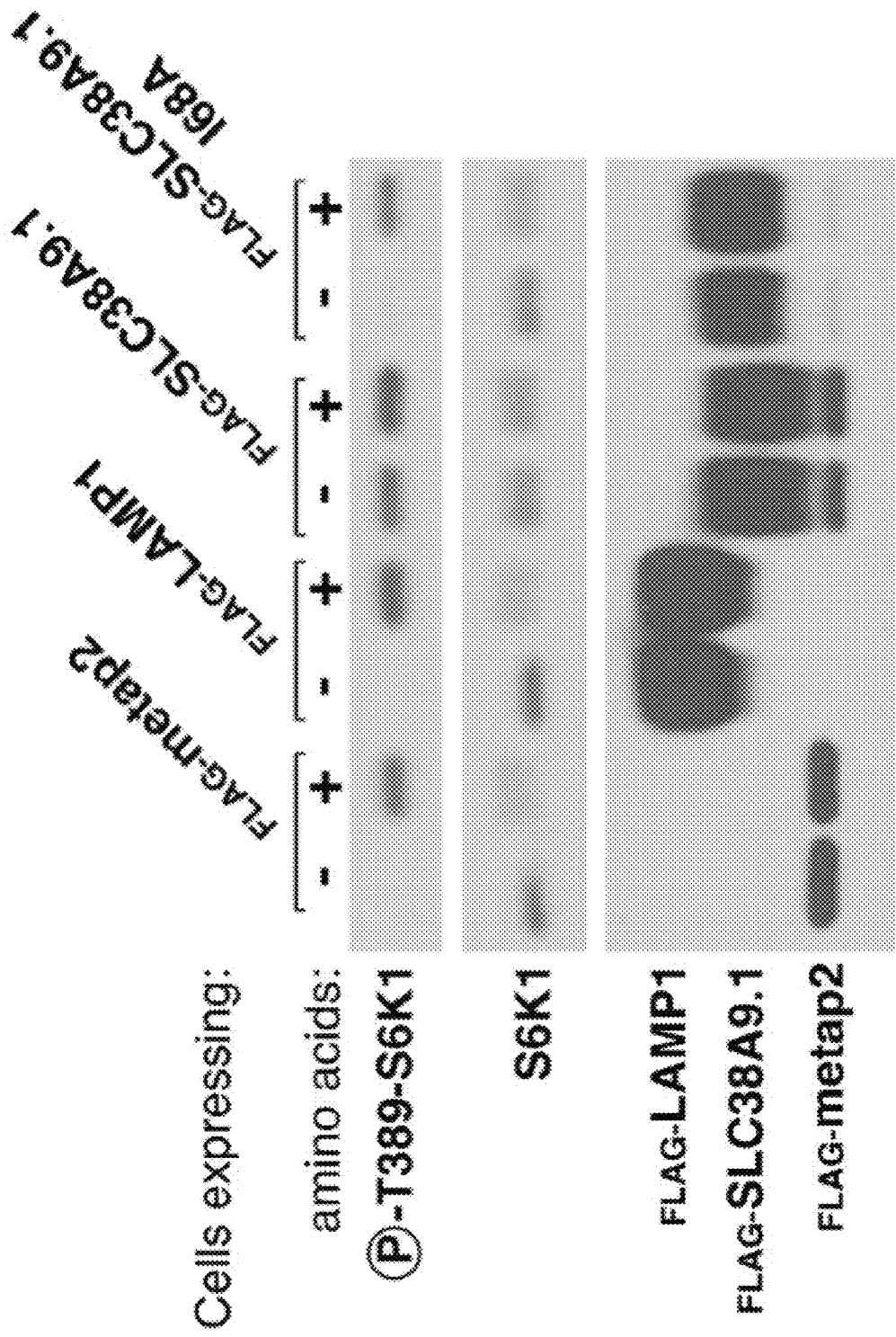
Figure 3D:
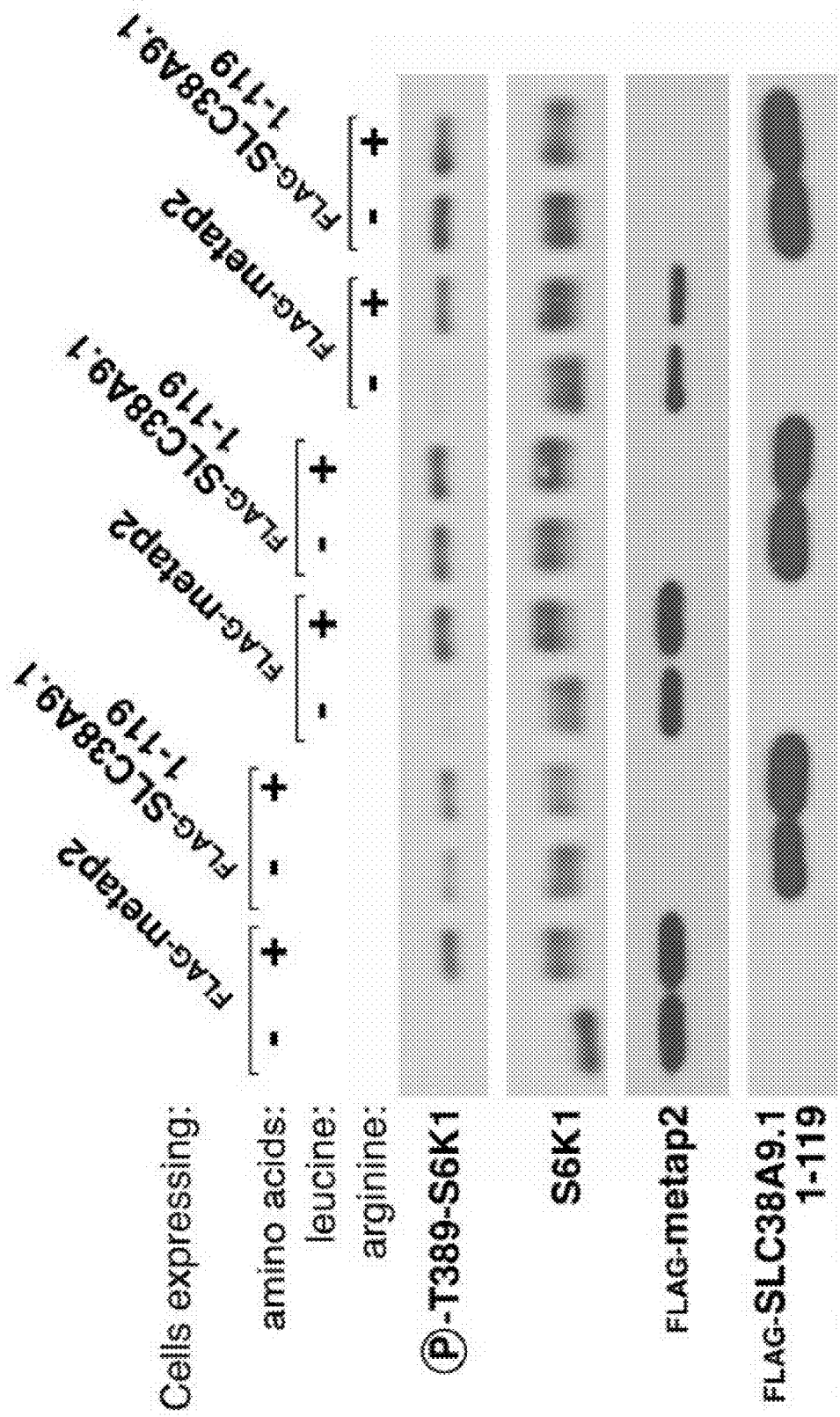
Figure 8A:
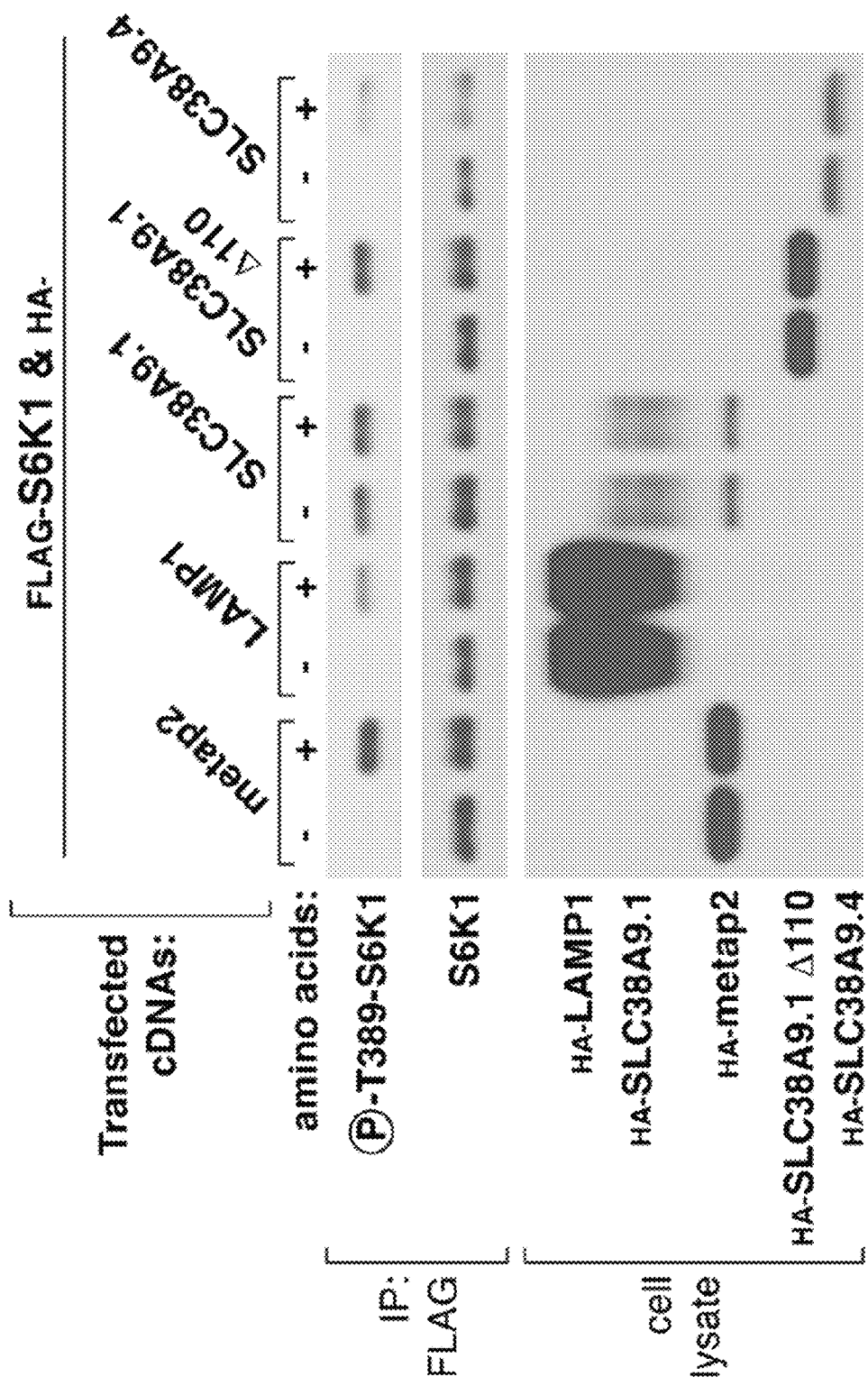
FIGS. 8A-8C depict immunoblots that demonstrate the effects of expression of SLC38A9.1, SLC38A9.4 and/or SLC38A9.1 Δ110.

Transient or stable overexpression of SLC38A9 isoform 1 in HEK-293T cells rendered mTORC1 signaling resistant to total amino acid starvation or to just starvation of leucine or arginine, as measured by the phosphorylation of Threonine 389 (T398) of exogenous S6K1—an established reporter for mTORC1 activity within cells (FIGS. 3A and 8A). Commensurate with its effects on mTORC1, SLC38A9.1 overexpression suppressed the induction of autophagy caused by amino acid starvation (FIG. 8C).

Transient overexpression of variants of SLC38A9 that do not interact with Ragulator and the Rag GTPases, including SLC38A9.2, SLC38A9.4, and the SLC38A9.1 Δ110 and SLC38A9.1 I68A mutants, failed to maintain mTORC1 signaling after amino acid withdrawal (FIGS. 3, B and C, and FIG. 8A).

Figure 8B:
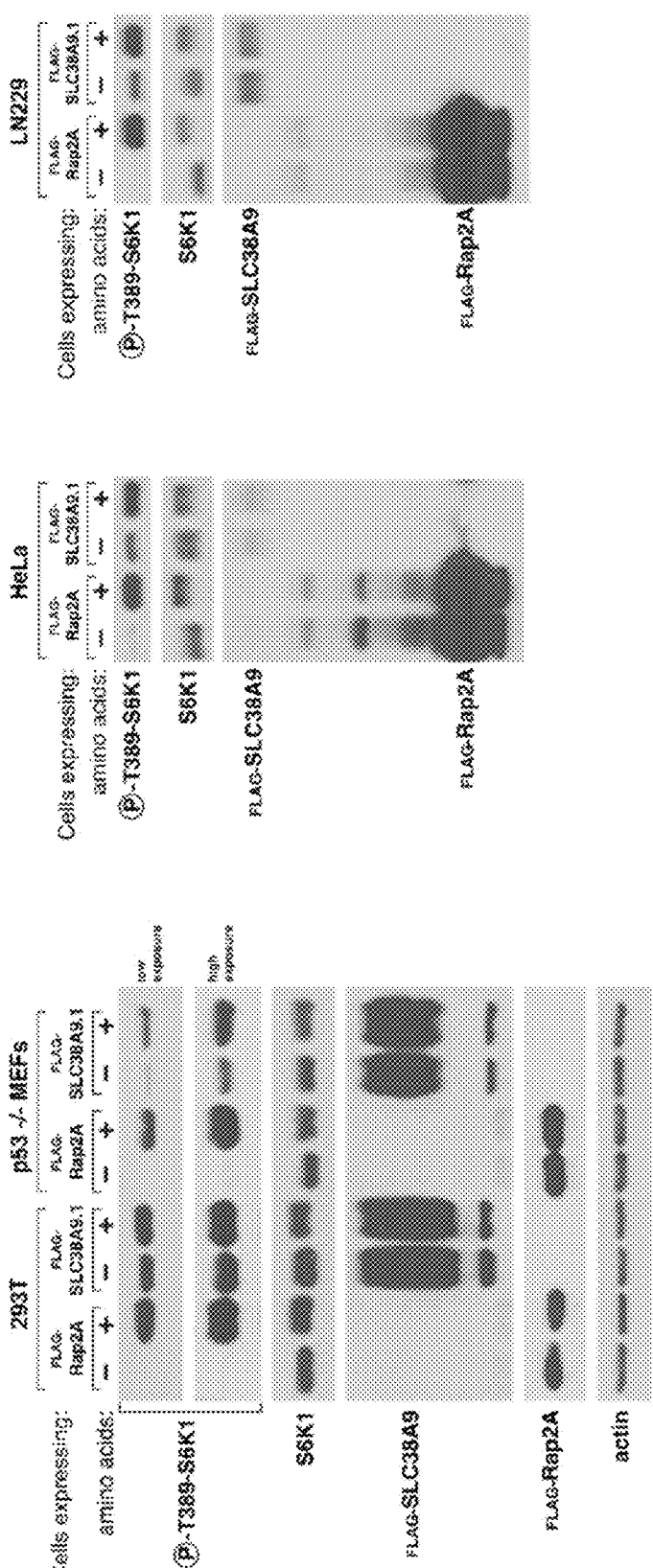
Figure 8C:
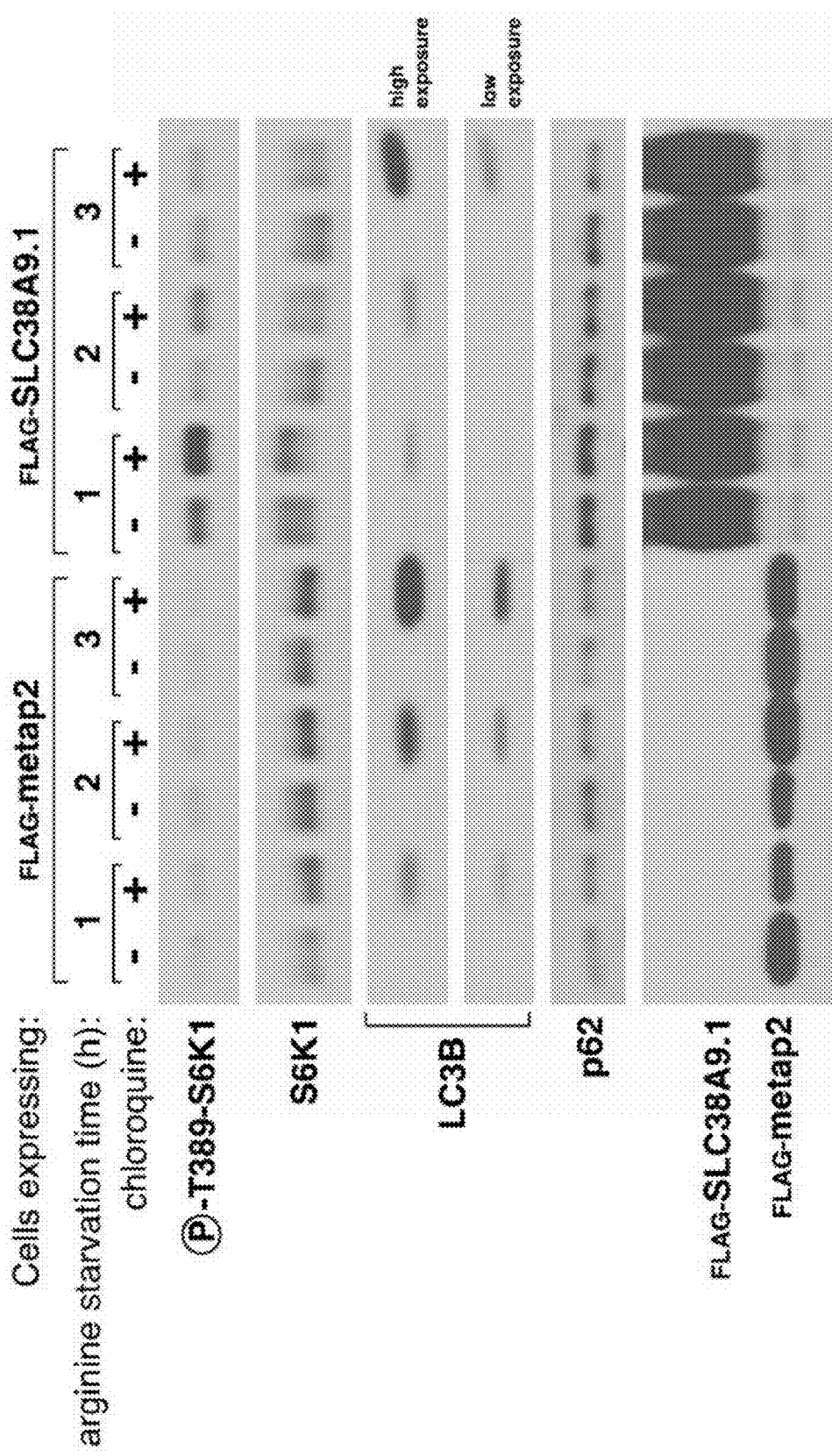

SLC38A9.1 overexpression also activated mTORC1 in the absence of amino acids in HEK-293E, HeLa, and LN229 cells, as well as in mouse embryonic fibroblasts (MEFs), with the degree of activation proportionate to the amount of SLC38A9.1 expressed (FIG. 8B). Interestingly, overexpression of just the Ragulator-binding domain of SLC38A9.1 mimicked the effects of the full-length protein on mTORC1 signaling (FIG. 3D), indicating that it can adopt an active state when separated from the transmembrane portion of SLC38A9.1.

We also prepared SLC38A9.1 knockouts using CRISPR/CAS9. The CRISPR/CAS9 guide sequences designed to the N-terminus (amino acids 1-119) of SLC38A9 or the AAVS1 locus disclosed below were cloned into pX459.

AAVS1:
GGGGCCACTAGGGACAGGAT (SEQ ID NO: 9)

SLC38A9_1:
GGCTCAAACTGGATATTCATAGG (SEQ ID NO: 10)

SLC38A9_2:
GGAGCTGGAACTACATGGTCTGG (SEQ ID NO: 11)

HEK-293T cells (750,000/well) were plated into 6 well dishes and transfected 16 hours later with 1 µg of pX459 expressing above guides using XtremeGene9. Cells were trypsinized 48 hours later, 2 mg/mL puromycin was applied for 72 hours, and allowed to recover for a few days. When cells were approaching confluency, they were single-cell sorted into 96-well dishes containing 30% serum and conditioned media. Clones were expanded and evaluated for knockout status by western analysis for SLC38A9. These clones were evaluated for amino acid response as described above.

HEK-293T cells depleted of SLC38A9 using CRISPR/CAS9 genome editing technology demonstrated partial inhibition of mTORC1 activation in response to amino acid stimulation. Based on these data, we hypothesize that SLC38A9 is a positive regulator of mTORC1 signaling in response to amino acids.

Example 4. LC-MS-MS Identification of Potential SLC38A9 Binding Partners

Using LC-MS-MS we identified TMEM192 (NCBI Gene ID: 201931), SLC12A9 (NCBI Gene ID: 56996) and CLCN7 (NCBI Gene ID: 1186) as potential protein binding partners with which SLC38A9 may homo-oligomerize and/or hetero-oligomerize. We believe that SLC38A9 may be associated with one or more of these other proteins as part of its function as an amino acid sensor upstream of mTORC1.

Example 5. Glycosylation Analysis of SLC38A9

In resolving expression of SLC38A9 by SDS-PAGE, we observed protein bands at higher molecular weight than expected. This is similar to patterns observed for glycosylated membrane proteins. Therefore, we conducted a bioinformatic analysis of the sequence of SLC38A9 and found that residues 117, 239, 248, 266 and 274 are potentially N-glycosylated. We believe, without being bound by theory, that glycosylation may play a role in the localization and function of SLC38A9 as an amino acid sensor and regulator of mTORC1 signaling. Glycosylation may also protect protein SLC38A9 from cleavage by lysosomal proteases.

Example 6. Modulation of the SLC38A9-Rag-Ragulator Interactions by Amino Acids

Amino acids modulate the interactions between many of the established components of the amino acid sensing pathway, so we tested if this was also the case for the SLC38A9.1—Ragulator-Rag complex.

HEK-293T cells (150,000/well) were plated onto fibronectin-coated 12-well dishes and transfected 12 hours later with the pRK5-based cDNA expression plasmids indicated in the figures in the following amounts using XtremeGene9: 400 ng LAMP1-FLAG, 400 ng FLAGSLC38A9.1, 400 ng SLC38A2-FLAG, 150 ng PQLC2-FLAG, and 50 ng GFP. Transfection mixes were taken up to a total of 2 µg of DNA using empty pRK5. Cells were assayed 48 hours later by washing twice in transport buffer (140 mM NaCl, 5 mM KCl, 2 mM MgCl2, 2 mM CaCl2, 30 mM Tris-HCl, pH 7.4, 5 mM glucose), incubating in transport buffer for 5 min. at 37° C. before replacing the buffer with fresh buffer supplemented with amino acids (unlabeled and 0.1 µCi of [$^{14}$C]leucine at a total concentration of 380 µM, or unlabeled and 0.1 µCi of [$^{14}$C]amino acid mix at total concentrations found in RPMI, or unlabeled and 0.2 µCi of [$^{14}$C]arginine at a total concentration of 3 mM) at the indicated pH (pH 5 buffered by MES, pH 8 buffered by Tris) for 10 minutes at 37° C. After uptake, cells were washed twice in ice-cold transport buffer and harvested in 0.5 mL of 1% SDS for scintillation counting.

Figure 4A:
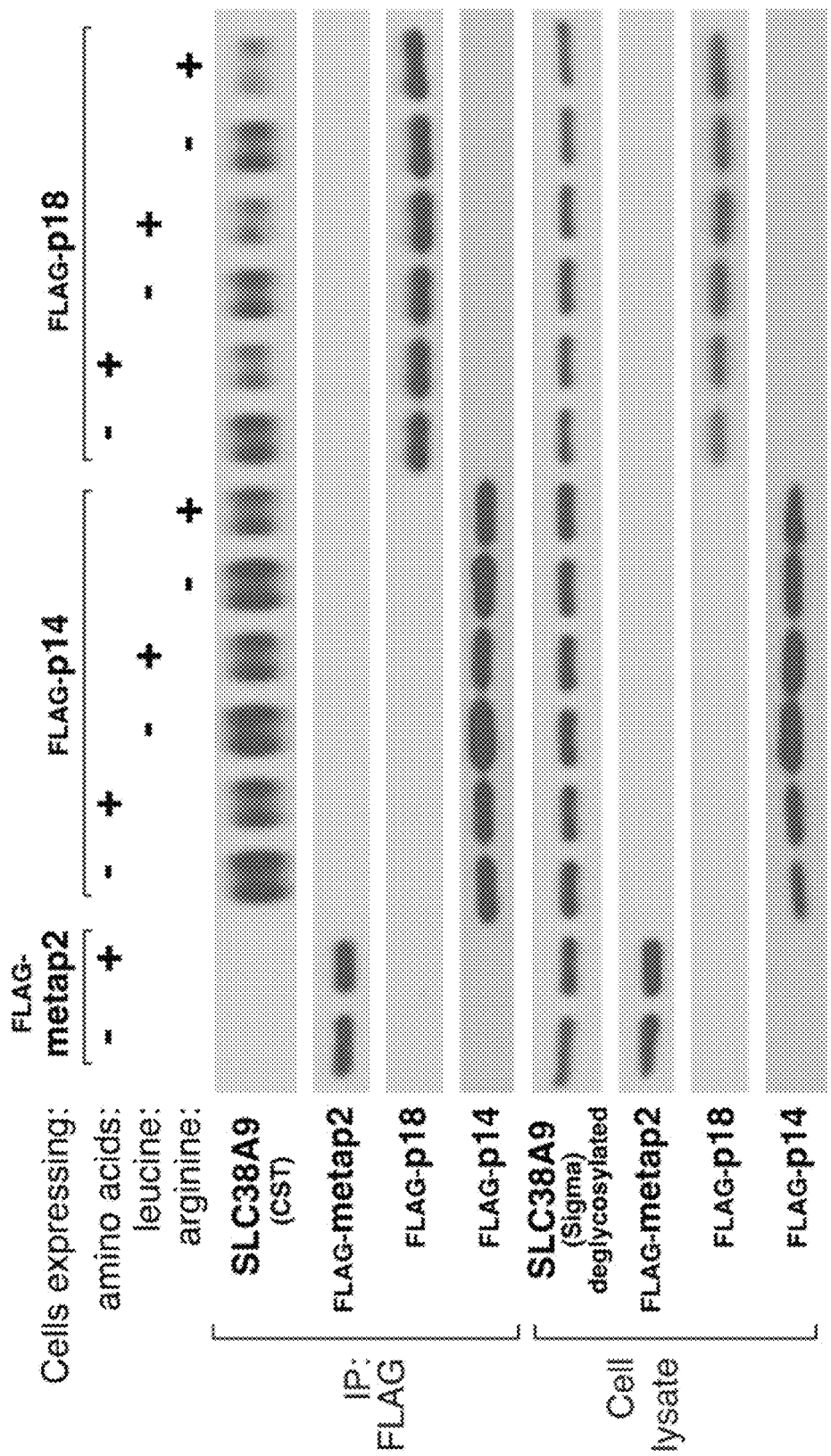
FIGS. 4A-4B depict immunoblots demonstrating the effect of amino acids on the interaction between SLC38A9.1 and Ragulator and the Rag GTPases in HEK-293T cells stably expressing the indicated FLAG-tagged protein.
Figure 4B:
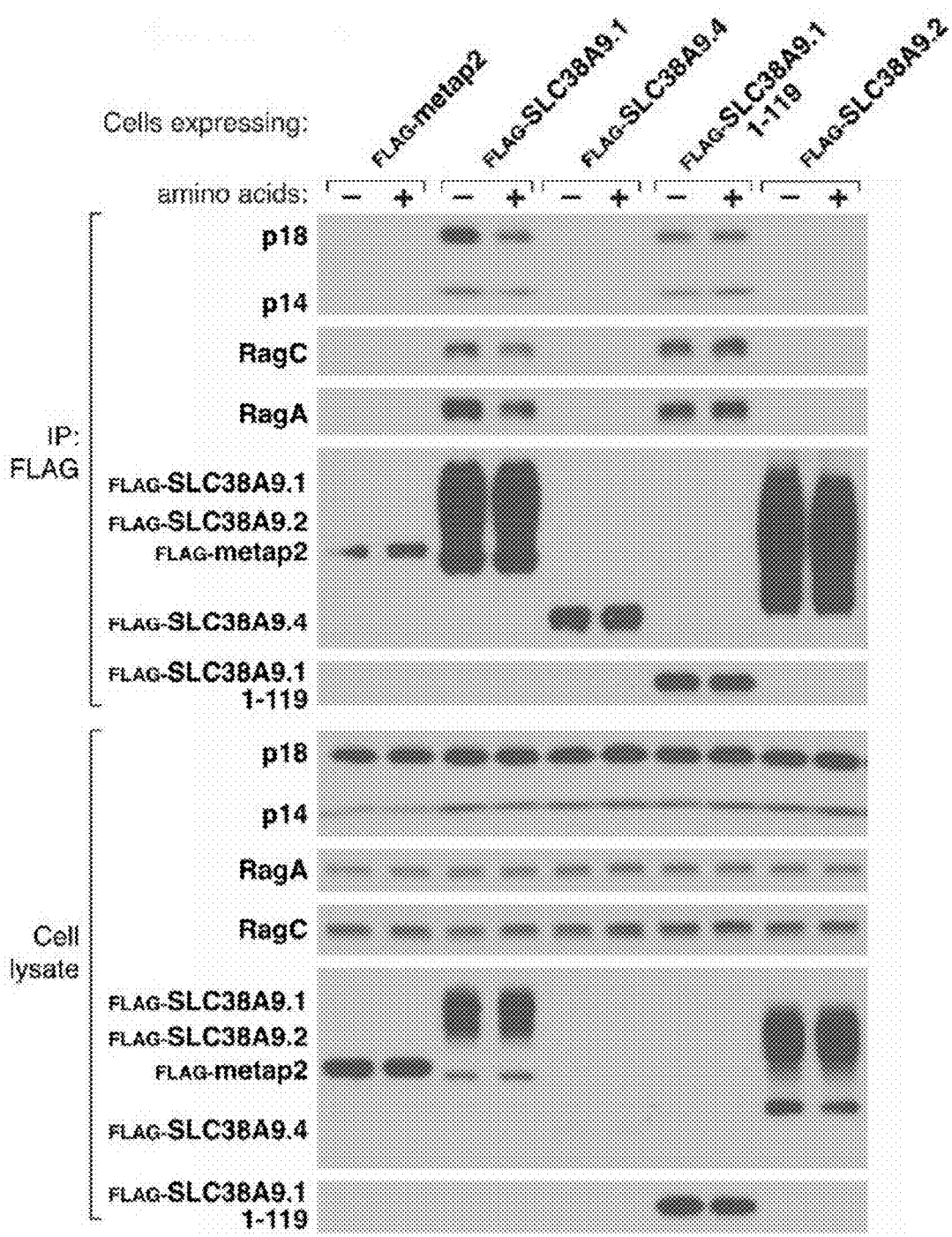
Figure 9:
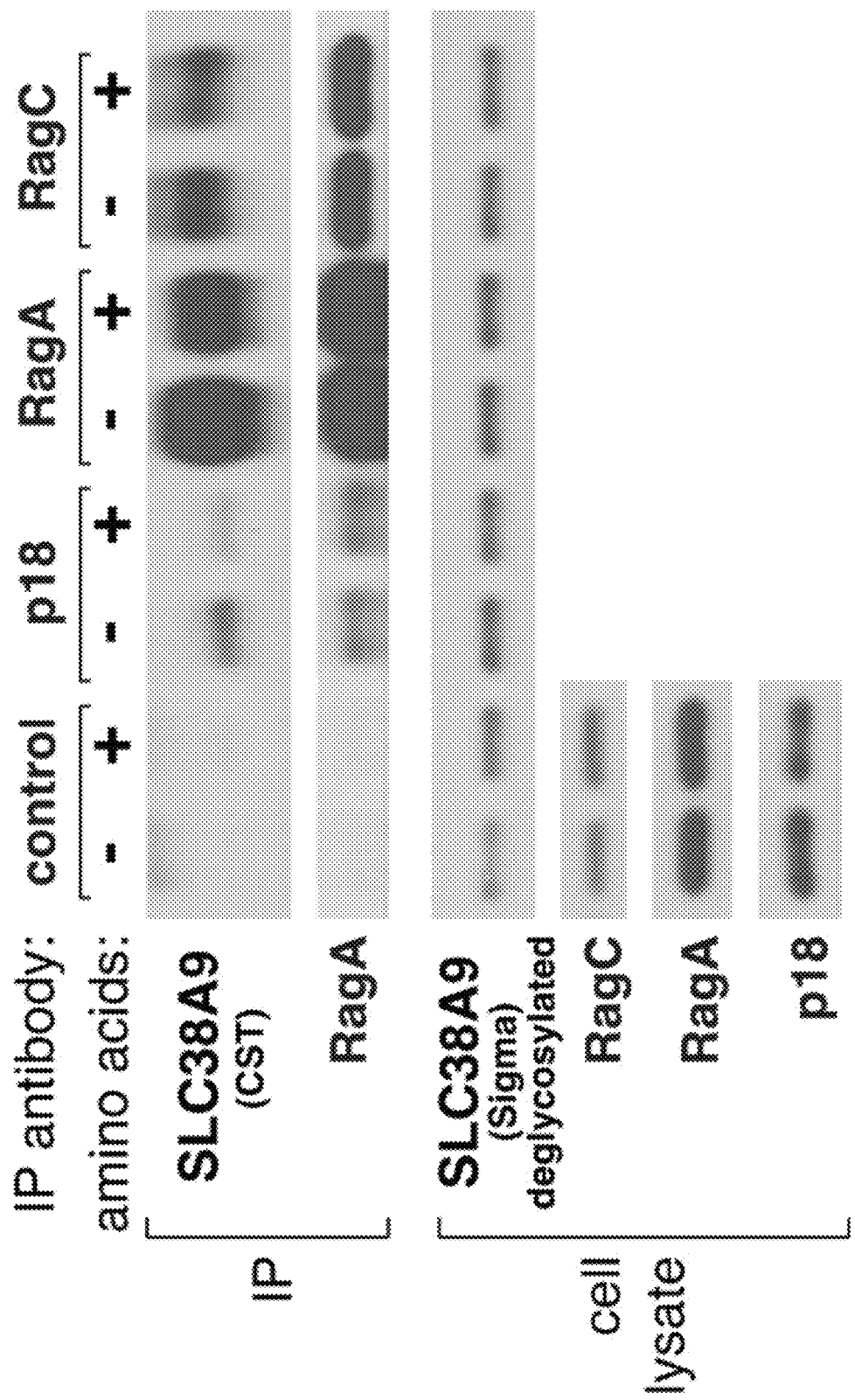
FIG. 9 depicts an immunoblot demonstrating the effect of amino acids on endogenous association of SLC38A9 with Rag and Ragulator components.

Indeed, amino acid starvation strengthened the interaction between stably expressed or endogenous Ragulator and endogenous SLC38A9 (FIG. 4A, FIG. 9); and between stably expressed SLC38A9.1 and endogenous Ragulator and Rags (FIG. 4B). We obtained similar results when cells were deprived of and stimulated with just leucine or arginine (FIG. 4A). Curiously, although the N-terminal domain of SLC38A9.1 readily bound Ragulator, the interaction was insensitive to amino acids (FIG. 4B), suggesting that the transmembrane region is required to confer amino acid responsiveness.

Figure 4C:
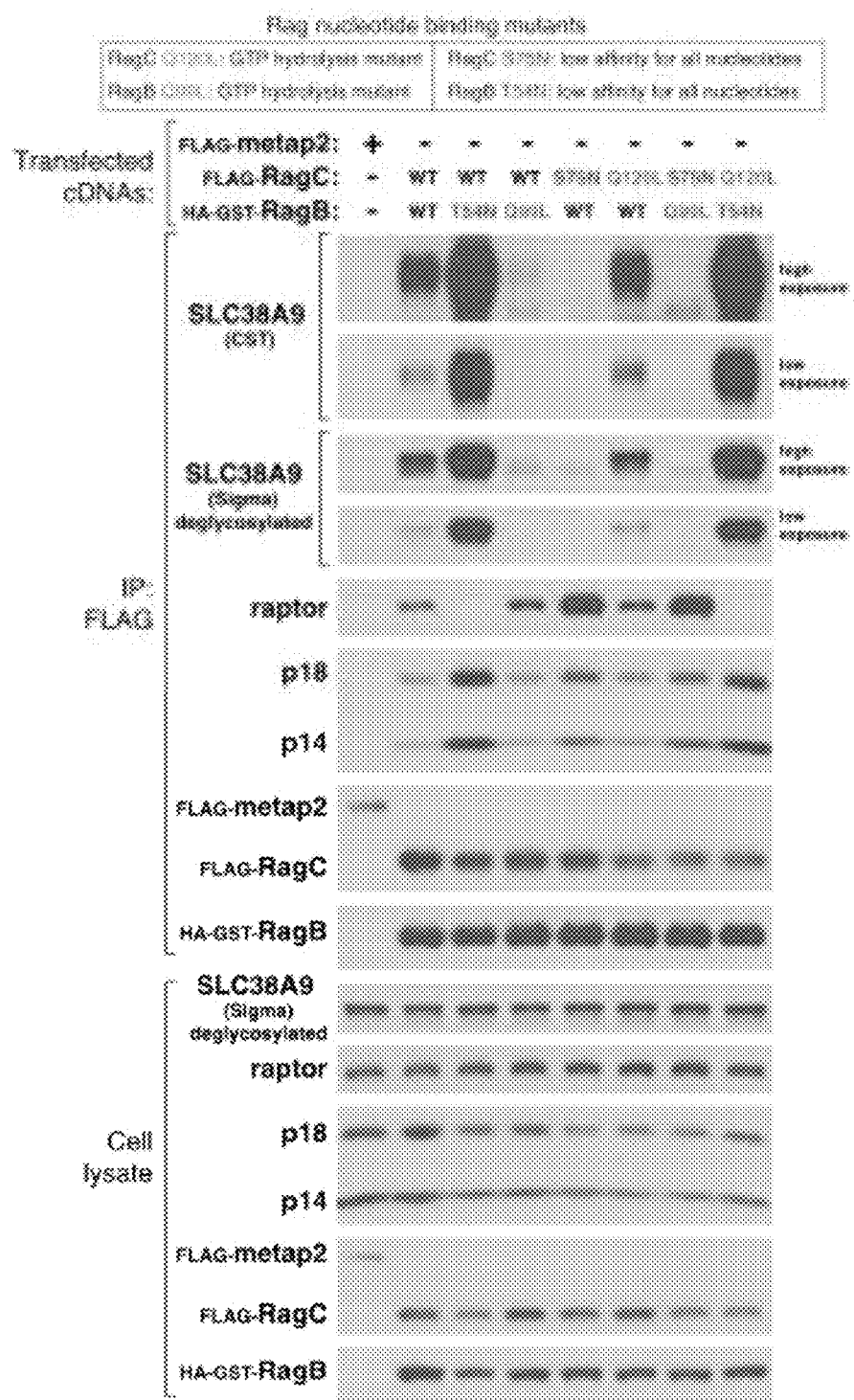
FIG. 4C depicts an immunoblot demonstrating the effects of various mutations in RagB and RagC on its association with endogenous SLC38A9 and Ragulator components in HEK-293T cells transfected with the indicated Rag B and/or RagC mutations.

As amino acid starvation alters the nucleotide state of the Rag GTPases, we tested whether SLC38A9 interacted differentially with mutants of the Rags that lock their nucleotide state. Heterodimers of epitope-tagged RagB-RagC containing RagBT54N, which mimics the GDP-bound state, were associated with more endogenous SLC38A9 than heterodimers containing wild-type RagB (FIG. 4C). In contrast, heterodimers containing RagBQ99L, which lacks GTPase activity and so is bound to GTP interacted very weakly with SLC38A9 (FIG. 4C). Thus, like Ragulator, SLC38A9 interacts best with Rag heterodimers in which RagA/B is GDP-loaded, which is consistent with SLC38A9 binding to Ragulator and with Ragulator being a GEF for RagA/B. These results suggest that amino acid modulation of the interaction of SLC38A9.1 with Rag-Ragulator largely reflects amino acid-induced changes in the nucleotide state of the Rag GTPases. Because the RagB mutations had greater effects on the interaction of the Rag GTPases with SLC38A9 than with Ragulator (in FIG. 4C compare the SLC38A9 blots with those for p14 and p18), it is very likely that the Rag heterodimers make Ragulator-independent contacts with SLC38A9 that affect the stability of Rag-SLC38A9 interaction.

Example 6. SLC38A9.1 is an Amino Acid Transporter

We failed to detect SLC38A9.1-mediated amino acid transport or amino acid-induced sodium currents in live cells in which SLC38A9.1 was so highly overexpressed that some reached the plasma membrane (FIG. 10, A-E). Because these experiments were confounded by the presence of endogenous transporters or relied on indirect measurements of transport, respectively, we reconstituted SLC38A9.1 or SLC38A9-A110 into liposomes to directly assay the transport of radiolabelled amino acids.

HEK-293T cells stably expressing FLAG-SLC38A9.1 were harvested as described above for immunoprecipitations, except cells were lysed in 40 mM HEPES pH 7.4, 0.5% Triton X-100, 1 mM DTT, and protease inhibitors. Following a 3 hr. immunoprecipitation, FLAG-affinity beads were washed twice for 5 min each in lysis buffer supplemented with 500 mM NaCl. Beads were equilibrated with inside buffer (20 mM MES pH 5, 90 mM KCl 10 mM NaCl) supplemented with 10% glycerol by washing them 5 times. FLAG-affinity purified SLC38A9.1 protein was eluted in glycerol-supplemented inside buffer containing 1 mg/mL FLAG peptide by rotation for 30 min. Protein was concentrated using Amicon centrifuge filters to about 1 mg/mL and snap-frozen in liquid nitrogen and stored at −80° C.

Purification of SLC38A9-Δ110 was performed as follows. Two liters of suspension 293F cells transiently transfected with His-SLC38A9-Δ110 were pelleted and the resulting cell paste went through 3 rounds of homogenization using a dounce homogenizer in 25 mM Tris, 10 mM $MgCl_2$, 20 mM KCl, pH 7.5 followed by ultra-centrifugation. After the third round, the resulting cell pellet went through 3 additional rounds of homogenization using a dounce homogenizer in 25 mM Tris, 1M NaCl, 10 mM $MgCl_2$, 20 mM KCl, pH 7.5 followed by ultra-centrifugation. The resulting pellet was then suspended in 25 mM Hepes, 150 mM NaCl, 5% glycerol, 2% DDM, pH7.5 (plus protease inhibitor tablets) and incubated overnight before ultra-centrifugation and collection of the resulting supernatant. His-SLC38A9-Δ110 was purified from the resulting supernatant by cobalt affinity column and eluted in 250 mM imidazole in 25 mM Hepes, 150 mM NaCl, 5% glycerol, 0.05% DDM, pH7.5.

To form liposomes, chloroform-dissolved phosphatidylcholine (PC, 50 mg) was evaporated using dry nitrogen to yield a lipid film in a round bottom flask and desiccated overnight under vacuum. Lipids were hydrated in inside buffer at 50 mg/mL with light sonication in a water bath (Branson M2800H) and split into 100 μL aliquots in Eppendorf tubes. Aliquoted lipids were clarified using water bath sonication and recombined and extruded through a 100 nm membrane with 15 passes (Avanti 61000). Reconstitution reaction (15 μg FLAG-SLC38A9.1 protein or 15 μg His-SLC38A9-Δ110, 7.5 mg Triton X-100, 10 mg extruded PC, 1 mM DTT in inside buffer up to 700 μL) was initiated by rotating at 4° C. for 30 min. Glycerol-supplemented inside buffer was used in lieu of SLC38A9.1 protein in liposome only controls. Bio-beads (200 mg/reaction) were prepared by washing 1 time in methanol, 5 times in water and 2 times in inside buffer. Reconstitution reaction was applied to Bio-beads for 1 hr, transferred to fresh Bio-beads overnight, and transferred again to fresh Biobeads for 1 hr.

To assay for amino acid transport, all buffers were chilled and assays performed in a 4° C. cold room. For time course experiments, SLC38A9.1 proteoliposomes or liposome controls were applied to PD10 columns equilibrated with outside buffer (20 mM Tris pH 7.4, 100 mM NaCl) and eluted according to manufacturer's instructions. Amino acid uptake was initiated by the addition of 0.5 μM [$^3$H]arginine and incubated in a 30° C. water bath. Time points were collected by taking a fraction of the assay reaction and applying it to PD10 columns pre-equilibrated with outside buffer. Columns were eluted in fractions or a single elution of 1.75 mL and added to 5 mL of scintillation fluid. To obtain accurate measures of amino acid concentrations, equal volumes of outside buffer was added to scintillation fluid in the standards.

For competition experiments with unlabeled amino acids, high concentrations of amino acids were required due to the high $K_m$ (~39 mM) of SLC38A9.1 import activity. SLC38A9.1 proteoliposomes or liposome controls were centrifuged at 100,000 g for 30 min. in a TLA-100.3 rotor and resuspended in a smaller volume of outside buffer such that they could be added to a larger volume of 100 mM unlabeled amino acid (final concentration) supplemented with outside buffer components. We had to resort to this procedure due to the solubility limit of leucine at ~130 mM. At such high concentrations, it is important to adjust all amino acid solutions to pH 7.4. Assays were initiated by addition of 0.5 μM [$^3$H]arginine to the amino acid buffer solution followed by the addition of SLC38A9.1 proteoliposomes or liposome controls.

For steady-state kinetics experiments, time points were collected as described above and to assess substrate specificity, competition experiments were collected at 75 min. For efflux experiments, SLC38A9.1 proteoliposomes or liposome controls were loaded with [$^3$H]arginine as described above for an import assay for 1.5 hrs. To remove external amino acids, the reactions were applied to PD10 columns pre-equilibrated with outside buffer, and time points were collected as described above. Scintillation counts from liposome controls were subtracted from that of SLC38A9.1 proteoliposomes.

Figure 5A:
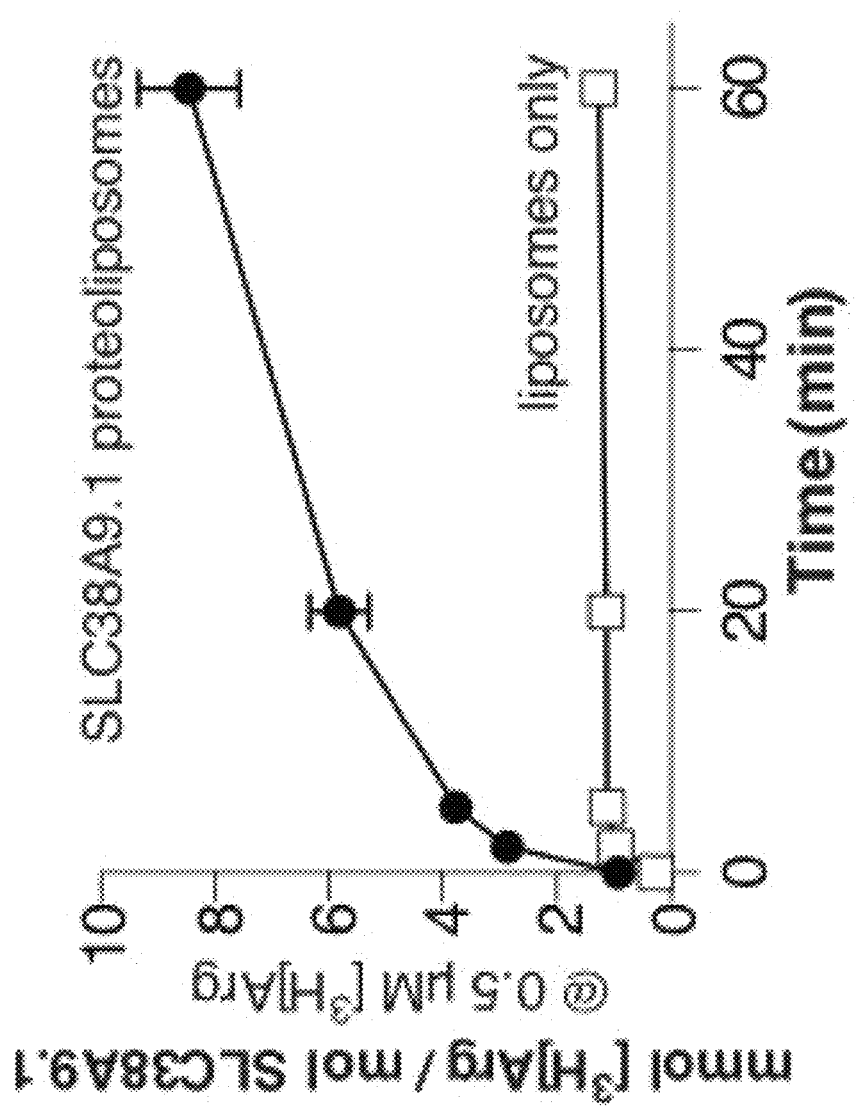
FIGS. 5A-5E depict the results of experiments arginine and related immunoblots depicting impairment of induced activation of the mTORC1 pathway.
Figure 5B:
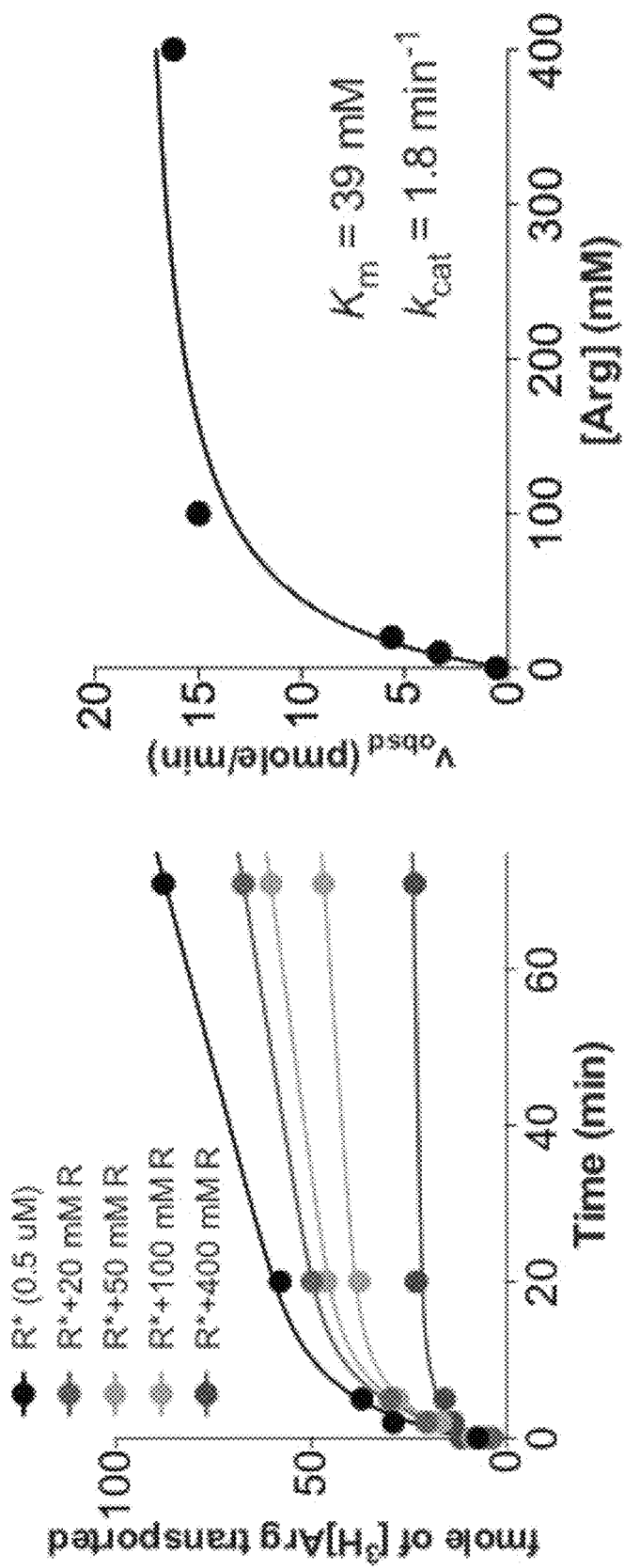
Figure 5C:
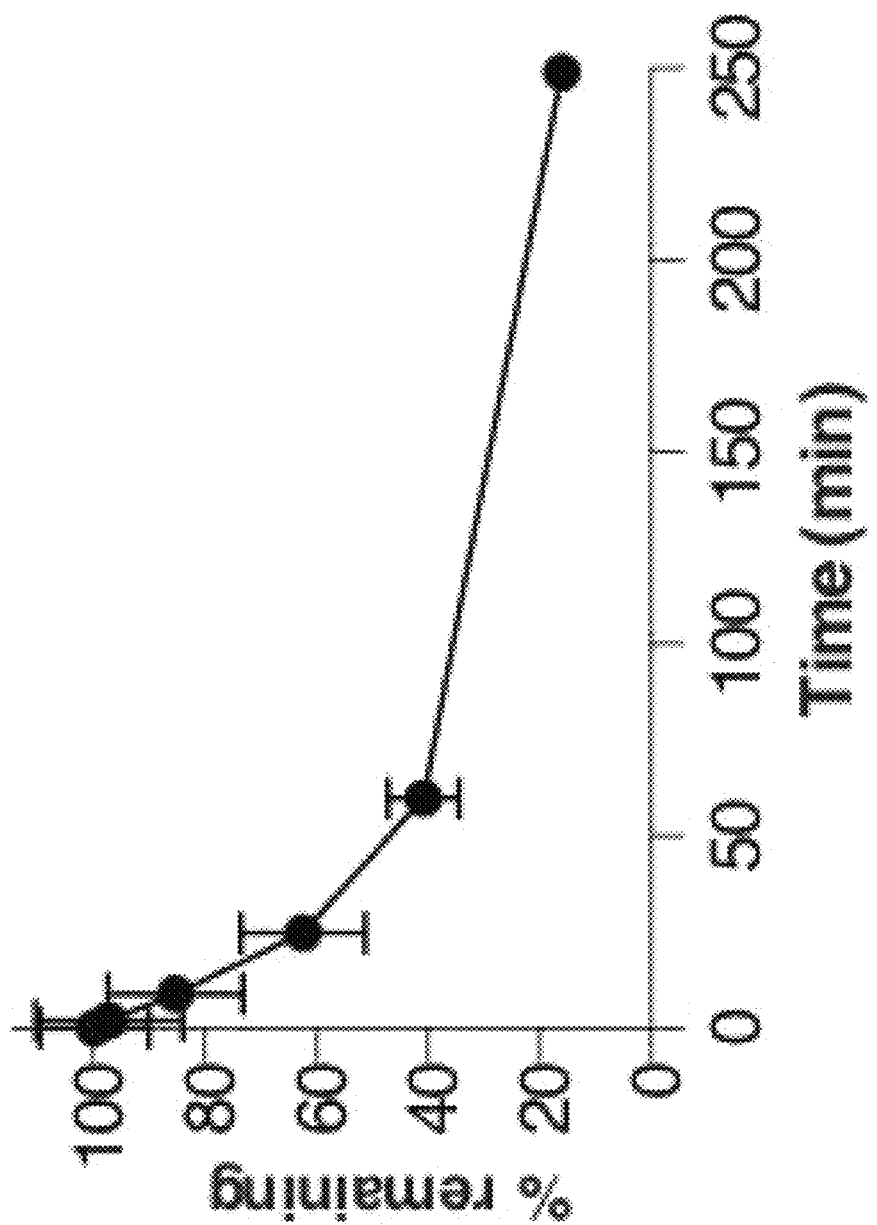
Figure 10A:
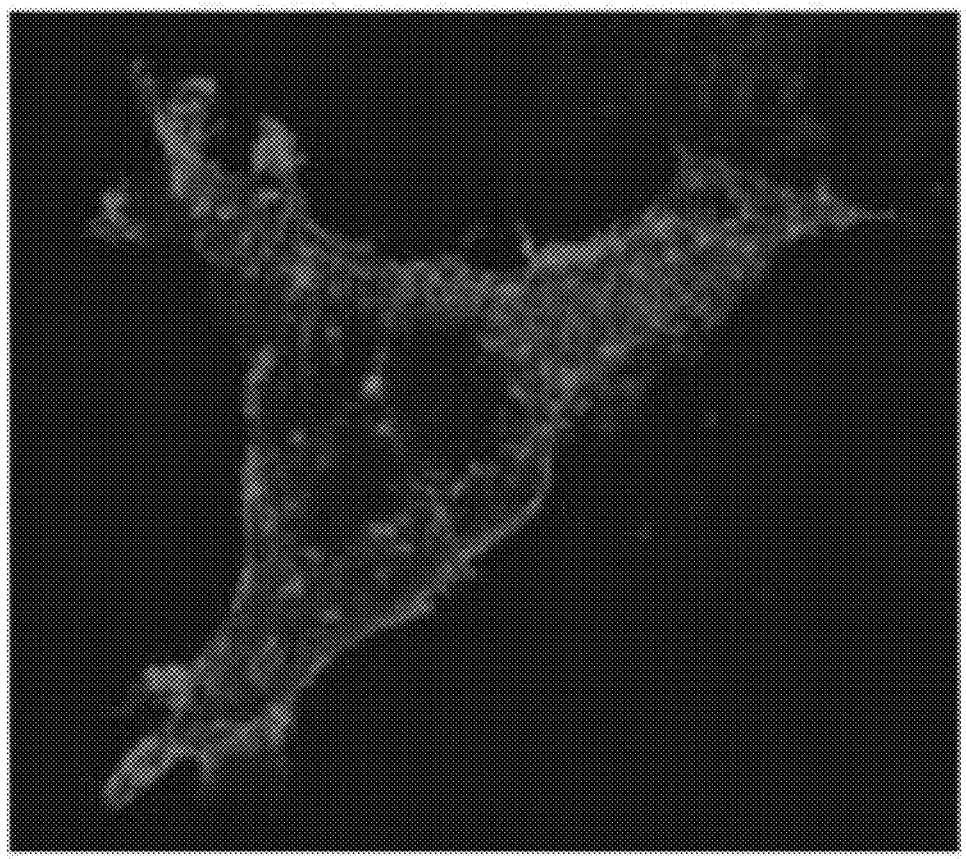
FIGS. 10A-10F depict the results of studies performed, for example, in HEK-293T cells.
Figure 10B:
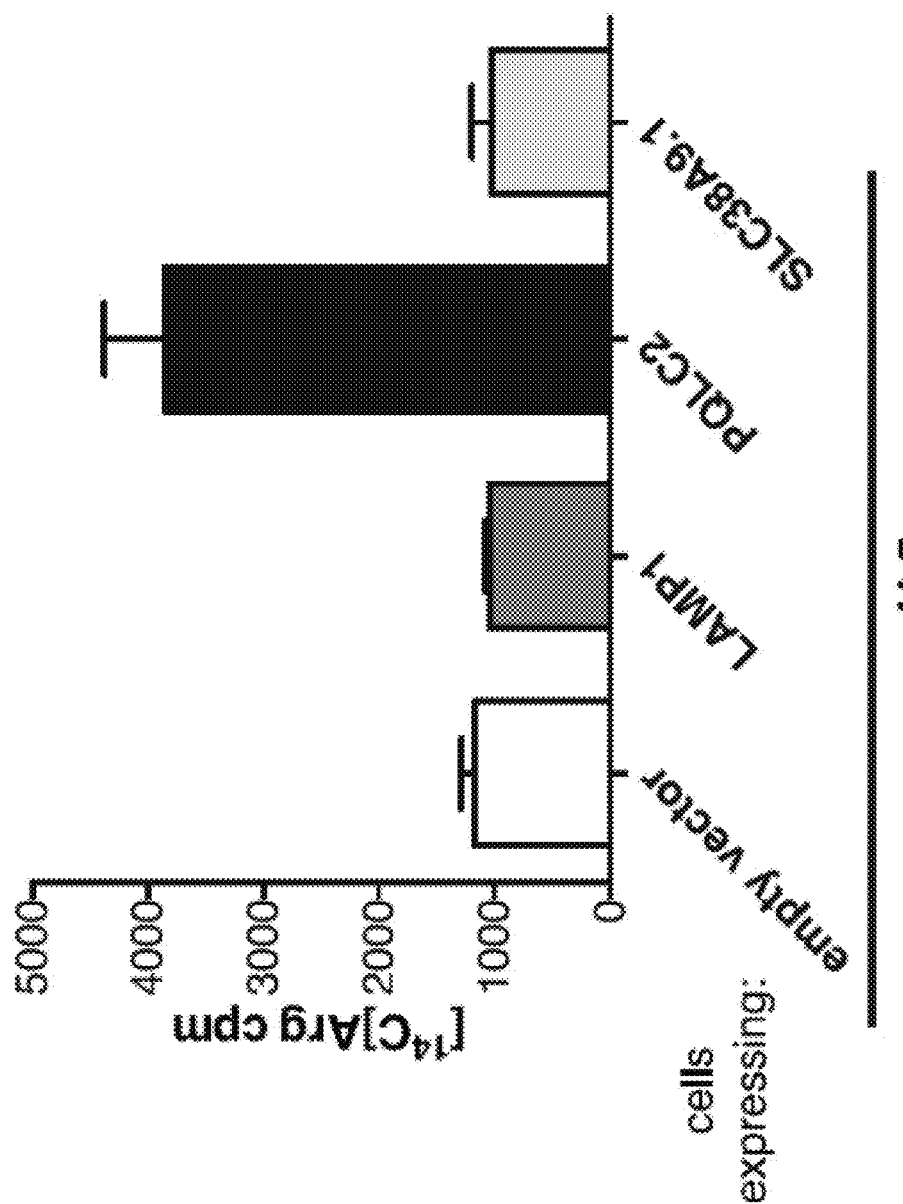
Figure 10C:
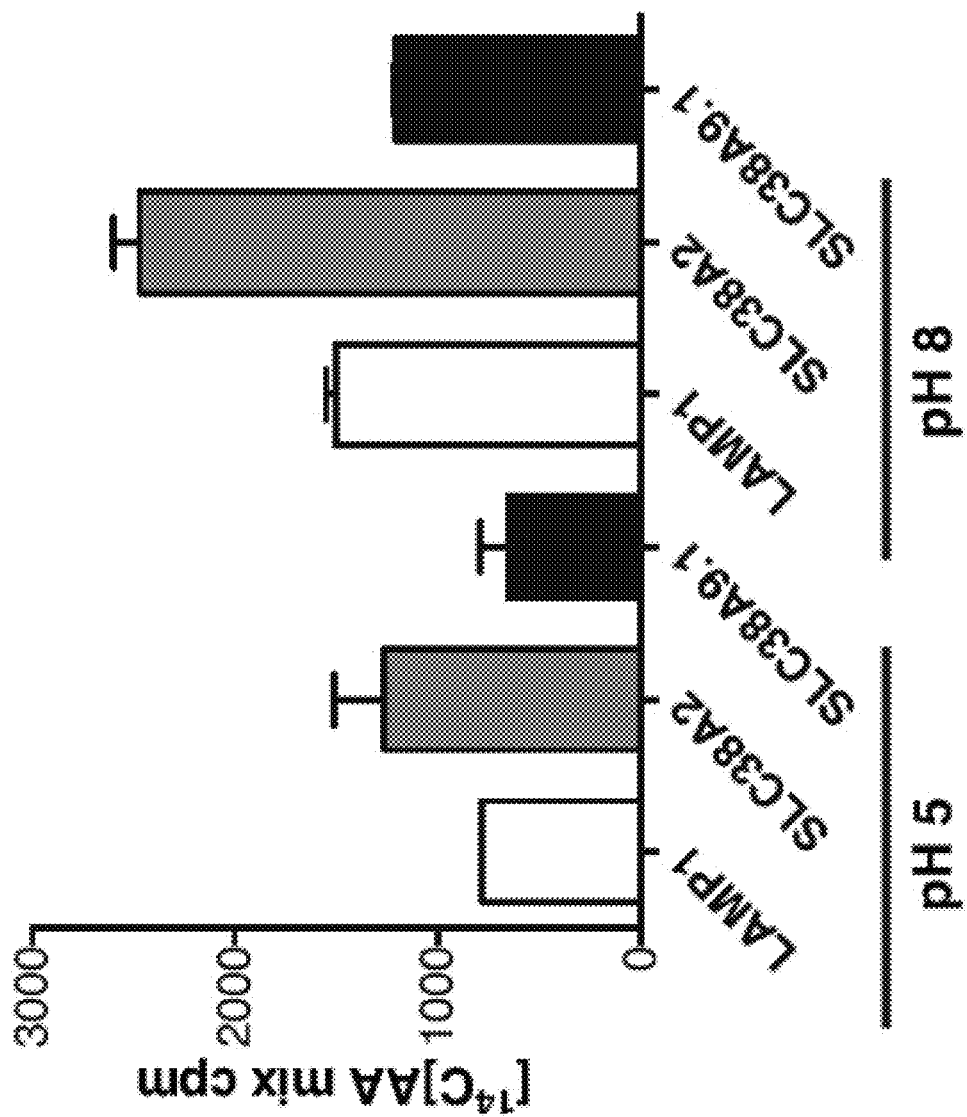
Figure 10D:
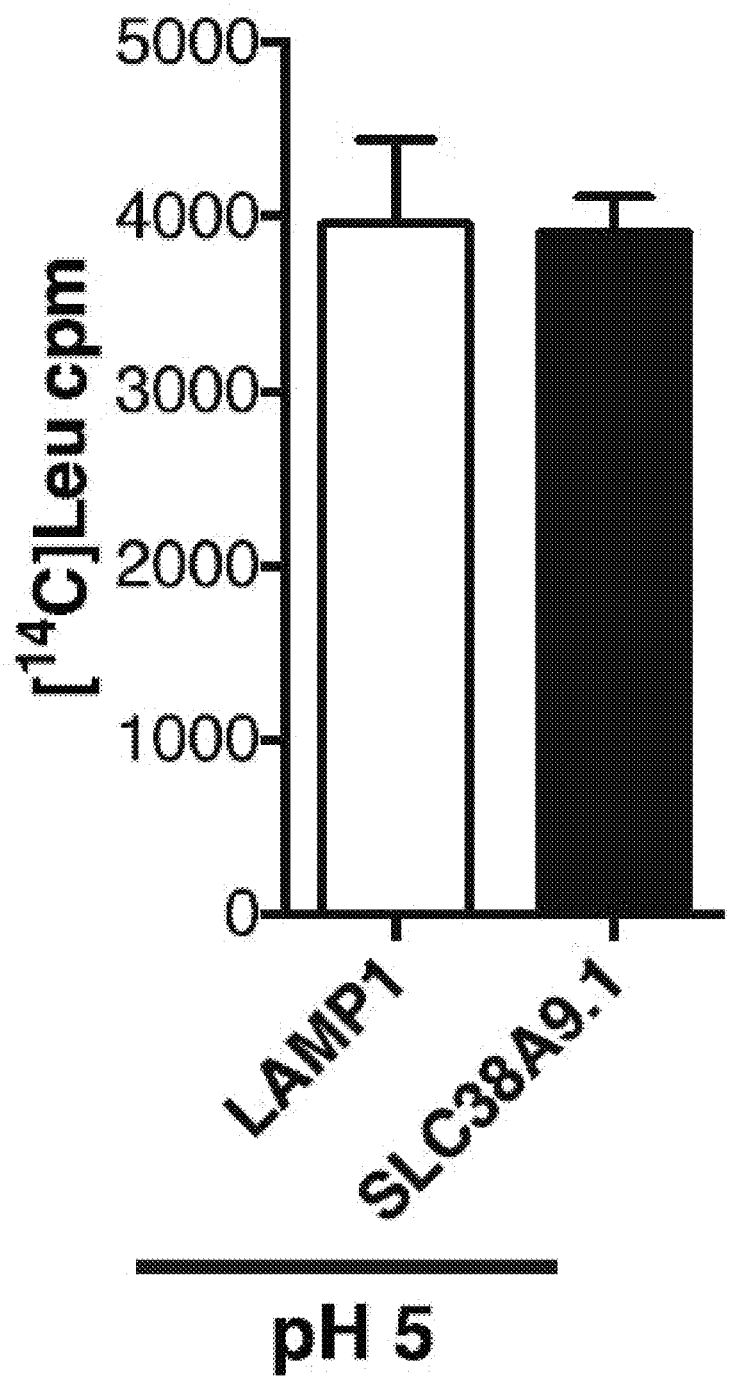
Figure 10E:
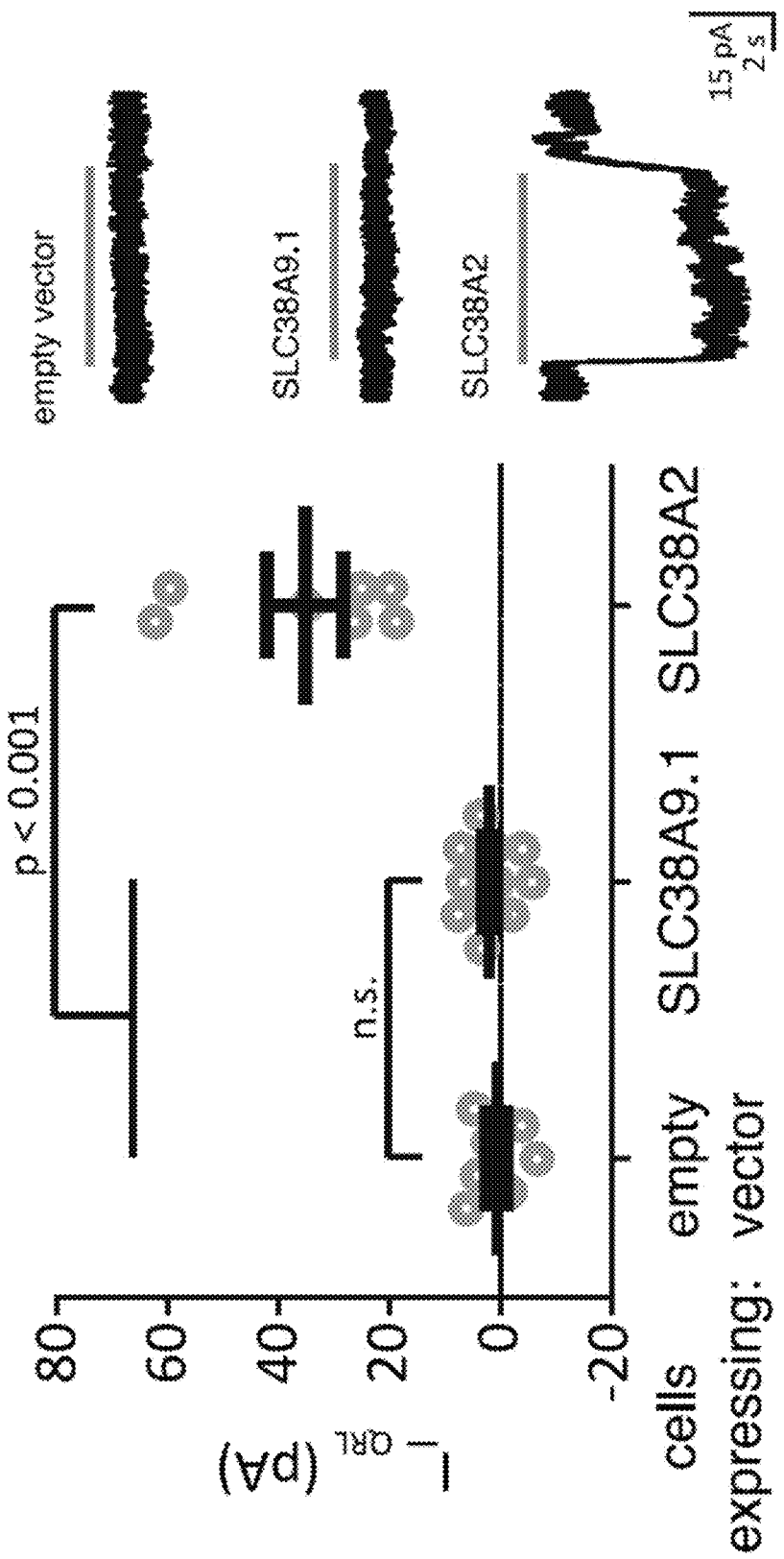
Figure 10F:
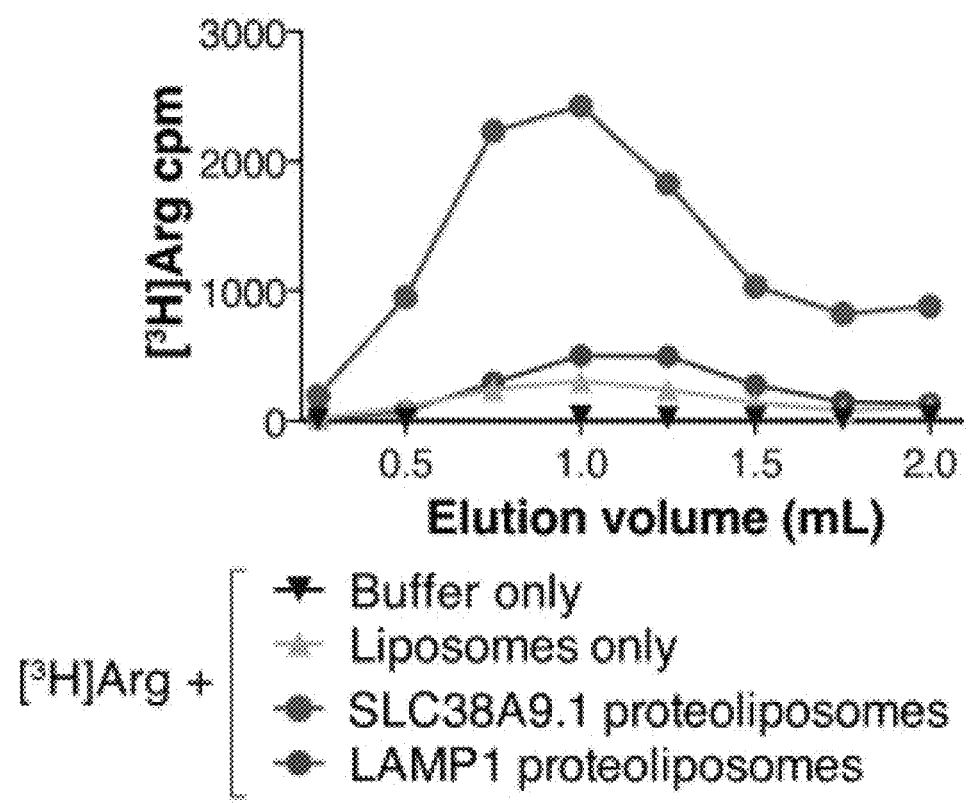
Figure 11:
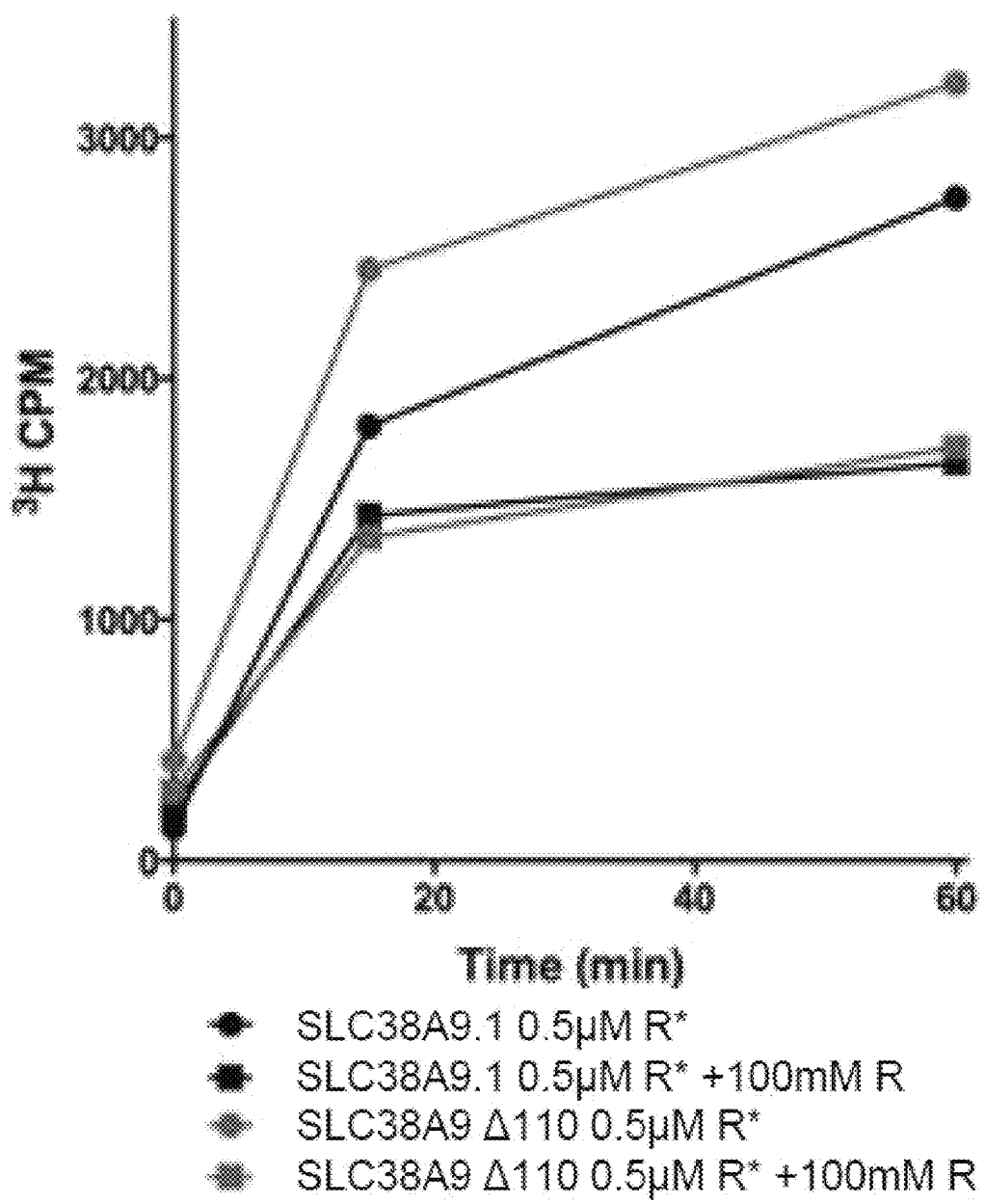
FIG. 11 depicts the time course of [$^3$H]arginine uptake by SLC38A9.1 ("38A9") liposomes or SLC38A9.1 Δ110 ("38A9 delta 110") liposomes, given fixed [$^3$H]arginine (0.5 μM) in the presence or absence of 100 mM unlabeled arginine.

Affinity-purified SLC38A9.1 or SCL38A9 Δ110 inserted unidirectionally into liposomes each exhibited time-dependent uptake of radiolabelled arginine while those containing LAMP1 interacted with similar amounts of arginine as liposomes (FIG. 5A, FIG. 11, FIG. 10F). Steady-state kinetic experiments revealed that SLC38A9.1 has a Michaelis constant ($K_m$) of ~39 mM and a catalytic rate constant ($k_{cat}$) of ~1.8 $min^{-1}$ (FIG. 5B), indicating that SLC38A9.1 is a low-affinity amino acid transporter. SLC38A9.1 can also efflux arginine from the proteoliposomes (FIG. 5C), but its orientation in liposomes makes it impossible to obtain accurate $K_m$ and $k_{cat}$ measurements for this activity. It is likely that by having to assay the transporter in the 'backwards' direction we are underestimating its affinity for amino acids during their export from lysosomes.

Figure 5D:
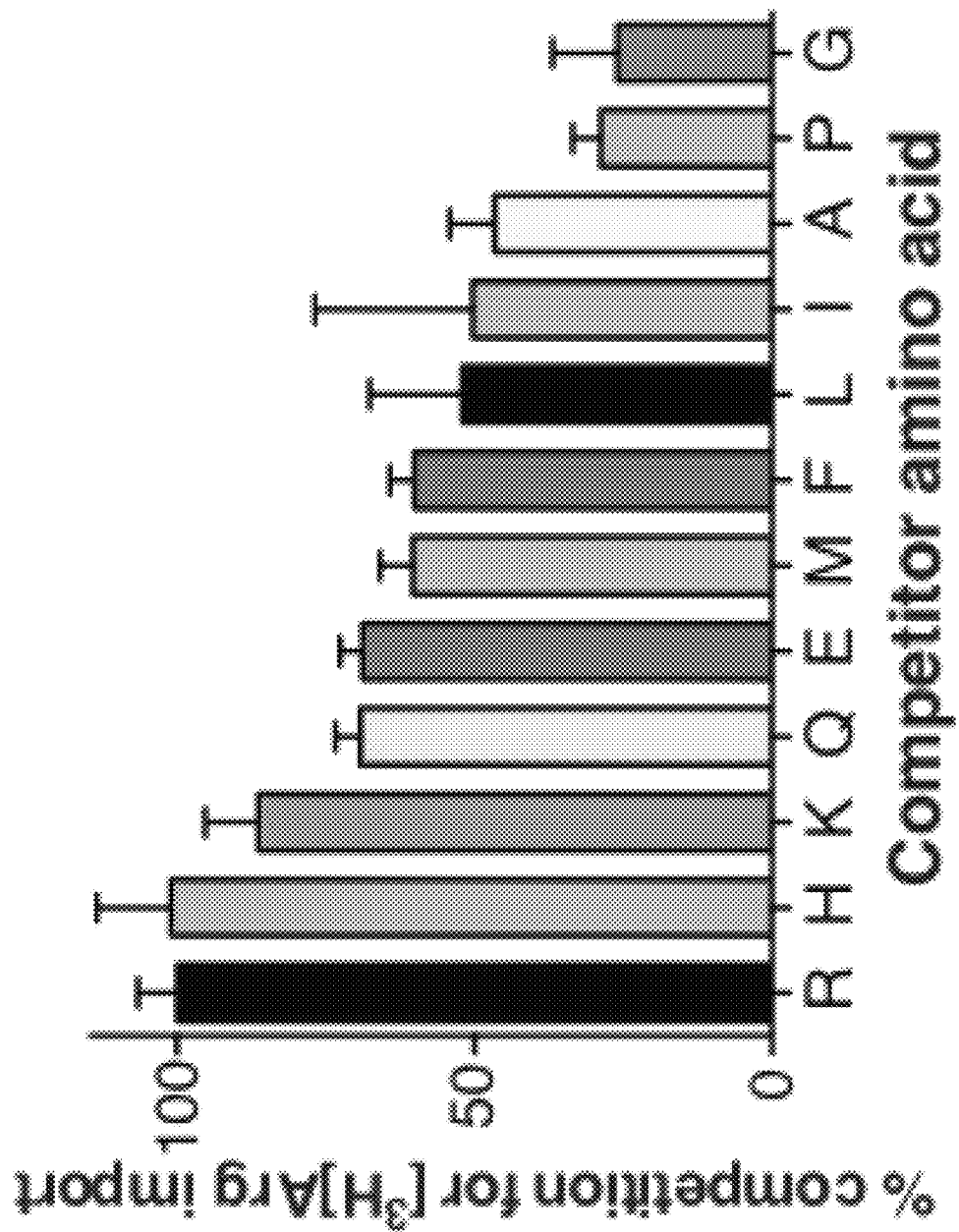
Figure 5E:
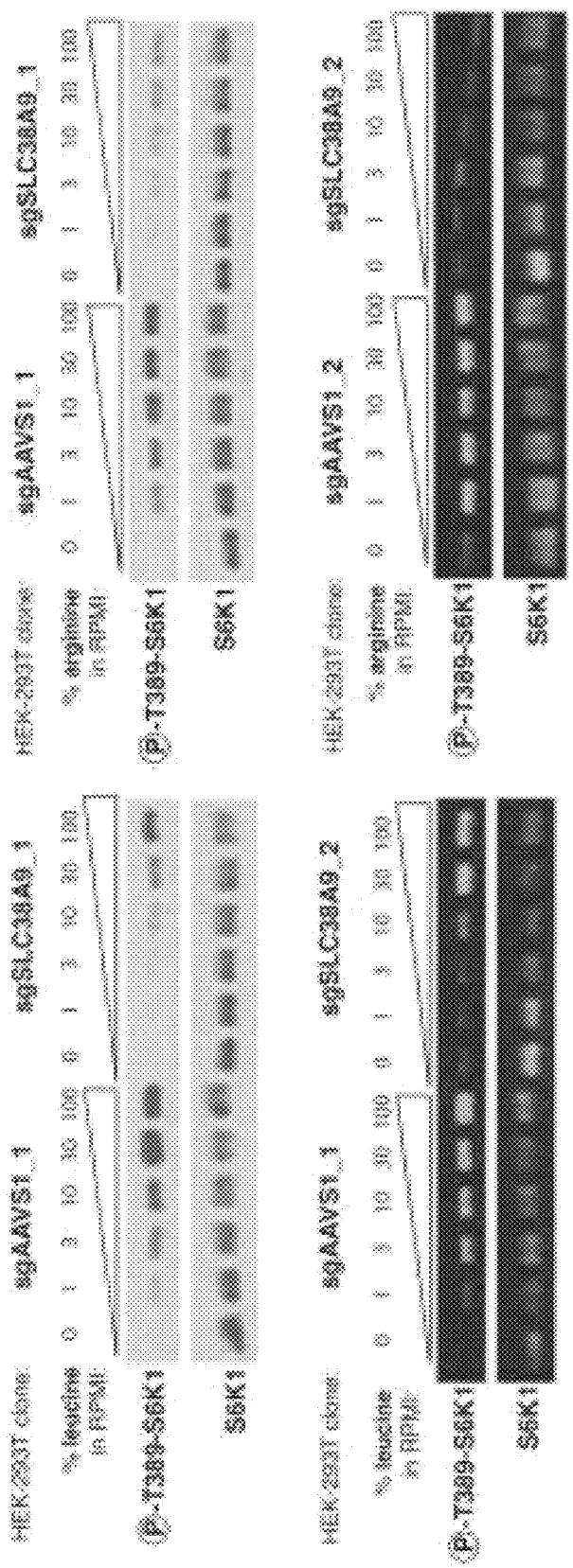

To assess the substrate specificity of SLC38A9.1, we performed competition experiments using unlabeled amino acids (FIG. 5D). The positively charged amino acids histidine and lysine competed radiolabelled arginine transport to similar degrees as arginine, while leucine had a modest effect and glycine was the least effective competitor. Thus, it appears that SLC38A9.1 has a relatively non-specific substrate profile with a preference for polar amino acids.

Given the preference of SLC38A9.1 for the transport of arginine and that arginine is highly concentrated in rat liver lysosomes and yeast vacuoles, we asked whether SLC38A9.1 may have an important role in transmitting arginine levels to mTORC1. Towards this end we examined how mTORC1 signaling responded to a range of arginine or leucine concentrations in HEK-293T cells in which we knocked out SLC38A9 using CRISPR/CAS9 genome editing as described above in Example 4. Interestingly, activation of mTORC1 by arginine was strongly repressed at all arginine concentrations in SLC38A9 knockouts, while the response to leucine was only blunted so that high leucine concentrations activated mTORC1 equally well in null and control cells (FIG. 5F).

Based on the findings described above, and without being bound by theory, we believe SLC38A9 binds sodium and specific amino acids, and in response likely undergoes conformational changes that result in mTORC1 activation through its interaction with Ragulator. Regarding amino acid substrate specificity, we believe SLC38A9 binds amino acids important to mTORC1 such as leucine, arginine, lysine and/or natural or synthetic derivatives of these, but we believe that SLC38A9.1 is a strong candidate for being a lysosome-based arginine sensor for the mTORC1 pathway. Binding of amino acids by SLC38A9 may also result in their transport across the lysosomal membrane. Given the pH sensitivity of other SLC38 family members as well as the pH sensitivity of amino acid sensing by mTORC1, we believe that increasing the intra-lysosomal pH is likely to inhibit signaling of SLC38A9 to mTORC1, while fluctuations in pH of the lysosome may be important for modulating the activity of SLC38A9 to mTORC1. Furthermore, the sodium binding site characteristic of the SLC38 family is present in SLC38A9; therefore, we speculate that it may also conduct a sodium current at the lysosomal membrane and that such a current may be modulated by amino acids and may be important for mTORC1 function.

Example 7. Assays to Measure Interaction Between SLC38A9 or Amino Acids 1-119 of SEQ ID NO:1 with the Rag C/B Heterodimer or Ragulator Test compounds that modulate mTORC1 activity can be identified via assays that determine its effect on the interaction between SLC38A9.1 (or amino acids 1-119 of SEQ ID NO:1) and the Rag heterodimer. Test compounds are incubated for a period of time with a cultured cell line that stably expresses either:
(i) endogenous SLC38A9.1 and either Rag heterodimers or Ragulator components; or
(ii) a combination of epitope tagged SLC38A9.1 (or amino acids 1-119 of SEQ ID NO:1) and/or epitope tagged RagA or RagB or RagC or RagD, and/or epitope tagged Ragulator components (p18, MP1, p14, HBXIP, C7orf59), wherein the tags do not prevent exogenous amino acids from modulating mTORC1 signaling.

After compound treatment, cells are lysed and endogenous or epitope-tagged Rag or Ragulator component(s) are immunoprecipitated as described in the art (Sancak et. al. Cell 141, 290-303, Apr. 16, 2010). Samples are then deglycosylated, processed for SDS-PAGE and immunoblotted for endogenous or epitope-tagged SLC38A9.1 or epitope-tagged-SLC38A9.1 or epitope tagged amino acids 1-119 of SEQ ID NO:1 as described above.

In another embodiment of this assay, endogenous or epitope-tagged Rag or Ragulator component(s) are captured on an immobilized surface via the appropriate antibody, and a sandwich ELISA is then performed for endogenous or epitope-tagged SLC38A9.1 or amino acids 1-119 of SEQ ID NO:1, as described according to the art (Daniele et al. Scientific Reports 4, Article number: 4749, 2014).

In still another version of this assay, the ELISA is performed with either fluorescent or luminescent substrates as described in the art (See, http://esmedia2.corning.com/Life-Sciences/media/pdf/elisa5.pdf).

The assays described in this Example 7 are be performed in cells that are starved for all amino acids, cells starved for arginine, cells starved for all amino acids and stimulated with all amino acids, cells starved for arginine and stimulated with arginine, and/or cells starved for all amino acids and stimulated with arginine.

Example 8. Assay to Identify Modulators of SLC38A9 Activity

A. Localization of SLC38A9 or SLC38A9 Δ110 to the Plasma Membrane.

Certain assays that are performed in live cells that require expression and localization of SLC38A9 to the plasma membrane. To localize SLC38A9 to the plasma membrane, the N- or C-terminus of SLC38A9 is fused to the last 25 amino acids of H-Ras (QHKLRKLNPPDESGPGCMSCK-CVLS). Alternatively, this 25 amino acid portion of H-Ras can be fused to the N or C-terminus of any peptide or polypeptide fragment or mutant of SLC38A9 that binds and is capable of transporting amino acids across a membrane, such as SLC38A9 Δ110. Such fusion proteins are targeted to and expressed at the plasma membrane.

Alternatively, the lysosomal localization sequence of SLC38A9 or any peptide or polypeptide fragment or mutant of SLC38A9 that binds and is capable of transporting amino acids across a membrane, such as SLC38A9 Δ110, is mutagenized. This would also target the resulting peptides, polypeptides or proteins to the plasma membrane as demonstrated in the art (Biochem J. 434(2):219-31, 2011).

Any of the above-described constructs are either transiently transfected or stably expressed in a cell line of choice, such as HEIS-239 cells.

B. Radiolabeled Substrate Uptake Assay:

Radiolabeled substrate uptake assays are performed in adherent or suspension cells expressing SLC38A9 or any peptide or polypeptide fragment or mutant of SLC38A9 that binds and is capable of transporting amino acids across a membrane, such as SLC38A9 Δ110, as described in the art (The Journal of Neuroscience, 14: 5559-5569, 1994). Briefly, cells are incubated in Dulbecco's phosphate buffered saline (D-PBS) in the presence or absence of a test compound at room temperature for a period of time prior to or concurrently with the addition of radiolabeled amino acid substrates. For testing of transport of SLC38A9 or SLC38A9 Δ110, transport is assessed for tritiated ($^3$H)-arginine, ($^3$H)-histidine and ($^3$H)-lysine at different concentrations and for different periods of time. At termination of the assay, adherent cells are washed three times in ice-cold D-PBS, solubilized in 0.1% SDS and processed for scintillation counting in an appropriate scintillation fluid (for example, ScintiVerse from Fisher Scientific). For suspension cells, at termination of the assay, the suspension are passed through Whatman GF/F micro-fiber filters (or a similar style filter), washed, and processed for scintillation counting in a standard manner. The values from these experiments may be used to calculate the substrate affinity constant. Compounds that result in lower scintillation counts are considered inhibitors of SLC38A9, while compounds that increased scintillation counts are considered SLC38A9 agonists.

C. Fluorescent Substrate Uptake Assay:

Transport of fluorescently labeled amino acid substrates for SLC38A9 is also measured in intact cells. The assay is the same as described for $^3$H-substrate uptake, with the test compound being added to the cells prior to or simultaneously with fluorescent amino acid substrates. Upon termination of the assay, the amount of fluorescent substrate taken up by cells is measured by a fluorescence microplate reader, fluorescent microscope or by flow cytometry as is performed in the art (Journal of Neuroscience Methods 169, 168-176, 2008). Changes in substrate uptake in response to compound are measured by changes in intra-cellular fluorescent intensity.

D. Intact Cell-Based Scintillation Proximity Assay:

Real-time analysis of $^3$H-substrate uptake by cells expressing plasma-membrane localized SLC38A9 or SLC38A9 Δ110 is accomplished using scintillant coated 96 or 384-well tissue-culture treated microwell plates (such as Cytostar-T plates from Perkin Elmer) according to the state of the art (Anal Biochem. 366(2):117-25, 2007). Briefly, adherent or suspension cells are grown to confluency in the scintillating microwell plates, washed and incubated with Hank's balanced salt solution or D-PBS containing $^3$H-amino acids substrates at different concentrations. Test compounds are added to cell-containing wells at various concentrations prior to or simultaneously with $^3$H-substrates. Real-time uptake of radiolabeled substrate is measured for a given amount of time by placing plate in a photomultiplier tube-based radiometric detector instrument capable of reading signals from a 96 or 384 well plate.

E. Fluorescent-Based Transporter Assays to Detect Sodium Transport:

SLC38A9 belongs to a family of sodium-dependent amino acid transporters and contains the amino acids required to coordinate and transport sodium. Transporter assays that detect the uptake of sodium are performed using sodium sensitive fluorescent dyes such as sodium-binding benzofuran isophthalate (SBFI) (J Biol Chem. 264(32): 19449-57, 1989), CoroNa Green (J Physiol 498, 295-307, 1997), or Asante NaTRIUM Green 1 (Neurolmage, Volume 58:2, 572-578, 2011). Briefly, cells expressing SLC38A9, SLC38A9 Δ110, or control proteins at the plasma membrane are pre-loaded with cell-permeable acetoxymethyl esters of the sodium-sensitive fluorescent dye as determined in the art, (Methods Enzymol 192:38-81, 1990), washed, and then incubated with test compounds at various concentrations either prior to or simultaneously with substrate amino acids and sodium chloride. When comparing cells overexpressing plasma membrane localized SLC38A9 or SLC38A9 Δ110 to cells expressing a negative control protein, an increase in fluorescence signal upon incubation with amino acid substrate and sodium chloride indicates increased sodium uptake due to transport via SLC38A9 or SLC38A9 Δ110. Changes in fluorescent intensity can be measured either via flow cytometry, fluorescence microplate or a spectrofluorophotometer.

F. Membrane Potential Assays:

The transport of sodium across a membrane by SLC38A9 may also lead to changes in membrane potential. There are multiple dyes available that, when pre-incubated with cells, allow changes in membrane protein to be measured by changes in fluorescence (such as FLIPR membrane potential dyes by Molecular Devices). Briefly, adherent cells are grown in black opaque microwell plates, washed, incubated in Hank's Balanced Salt Solution and membrane potential dye for a period of time sufficient to allow cells to be loaded with dye. The cells are then incubated with test compound. After incubation with test compound, the dye-loaded cell plate is loaded onto a FLIPR workstation, which allows for real-time detection of plasma membrane potential changes upon addition of amino acid substrates and sodium chloride (Assay and Drug Development Technologies, 6:2, 2008). Test compounds that prevent changes in membrane potential upon incubation with substrate and sodium chloride are considered inhibitors of SLC38A9 while compounds that lead to greater membrane depolarization are considered SLC38A9 agonists.

G. Whole-Cell Patch Clamping:

Transport of amino acids and sodium by SLC38A9 may generate an electrical current that can be detected by whole cell patch clamping. Neurons or cells overexpressing SLC38A9 or SLC38A9 Δ110 at the plasma membrane are first starved for amino acids before being subjected to whole cell patch clamping with borosilicate glass recording pipettes (3-5 μM). External and internal solutions are formulated to be compatible with recording currents from sodium-dependent amino acid transporters of the SLC38 family as described in the art (The Journal of Biological Chemistry 284, 11224-11236, 2009). The frequency and amplitude of miniature excitatory postsynaptic currents (mEPSC) are recorded under voltage clamp (at a holding potential of -70 mV) in the presence or absence test compound and the presence or absence of amino acid substrate in the external solution. Compounds that subsequently decrease frequency or amplitude of excitatory currents are considered inhibitors of SLC38A9 while compounds that increased frequency or amplitude of excitatory currents are considered agonists of SLC38A9.

H. Endolysosomal Patch Clamping:

Direct patching of endolysosomes isolated from cells expressing wild-type SLC38A9 or SLC38A9 Δ110 fused to a fluorescent protein, such as green fluorescent protein (GFP), is employed as described in the art (Cell. 152(4): 778-790, 2013). Briefly cells expressing SLC38A9 or SLC38A9 Δ110 fused to a fluorescent protein are cut at the plasma membrane and lysosomes, identified by their fluorescent staining of SLC38A9 or SLC38A9 Δ110 are pushed out for patch clamp recordings. Cytosolic and luminal buffers are formulated according to the art for measuring activity of other SLC38A family members (Cell. 152(4): 778-790, 2013) and excitatory recordings are taken in the presence or absence of SLC38A9 substrates and in the presence or absence of test compounds. Test compounds that modulate excitatory signals from the clamp are considered modulators of SCL38A9.

I. Oocyte-Based Transporter Assays:

*Xenopus oocytes* are isolated and microinjected according to the art (J. Biol. Chem. 286:20500-20511, 2011) with in vitro transcribed mRNA corresponding to a plasma-membrane directed form of SLC38A9, SLC38A9 Δ110 or a control protein. Resulting *oocytes* are placed into wells of a 96-well plate, incubated with Krebs-Ringer HEPES (KRH) buffer. The *oocytes* are incubated with test compounds added prior to or simultaneously with a combination of unlabeled and $^3$H-labeled amino-acid substrate and sodium chloride for 1 hour at 30° C. before termination of the assay with the addition of cold KRH buffer (J. Biol. Chem. 286:20500-20511, 2011). After termination, cells are lysed in 10% SDS and transferred to a scintillation tube for quantification of radiolabeled amino acid uptake. Compounds that inhibited uptake of $^3$H-substrates are considered inhibitors of SLC38A9 while compounds that increased uptake of $^3$H-substrates are considered SLC38A9 agonists J. Scintillation Proximity Assay:

Binding of radiolabeled amino acid substrates to SLC38A9 or SLC38A9 Δ110 is measured using a Scintillation Proximity Assay (SPA). Briefly, N-terminal His-tagged SLC38A9 or N-terminal His-tagged SLC38A9 Δ110 is immobilized onto copper chelate fluoromicrosphere beads containing scintillate. The radiolabeled substrate binding assay is then performed with this protein/bead complex plus appropriate controls as described in the art (Nature Protocols, 7:9, 1569-1578, 2012). Test compounds are added prior to or simultaneously with radiolabeled substrates. Compounds that decrease the scintillate count are considered inhibitors of SLC38A9 while compounds that increased binding of the radiolabeled substrate are considered SLC38A9 agonists.

K. Nanodisc Based Direct Binding Assays:

SLC38A9 or SLC38A9 Δ110 are assembled into Nanodiscs as described in the art (FEBS Lett. 584(9):1721-7, 2010). Once assembled into Nanodiscs, the polypeptide become amenable to a wide range of biophysical assays measuring direct binding of small molecules and amino acid substrates including:

1. Solid phase surface plasmon resonance. Nanodiscs containing SLC38A9 or SLC38A9 Δ110 are immobilized onto a matrix plate either via direct amine coupling or through an avidity tag fused to the Nanodisc or the N-terminus of SLC38A9 or SLC38A9 Δ110. Once immobilized, small molecule binding is measured as described previously (Analytical Biochemistry 408, 46-52, 2011).

2. Solution phase measurement of small molecule binding. Nanodisc containing N-terminal epitope tagged SLC38A9 or SLC38A9 Δ110 are incubated with test compounds for a period of time. The Nanodisc containing protein is immunoprecipitated, and the small molecules remaining in solution are subjected to analysis via mass spectrometry. This allows detection and identification of small molecules that are depleted upon incubation with Nanodiscs containing SLC38A9, but not negative control proteins. The degree of compound depletion from the solution is correlated to test compound affinity to protein.

Sequences

```
>gi|222418629|ref|NP_775785.2|putative sodium-coupled
neutral amino acid transporter 9 isoform 1 [Homo sapiens]
                                              SEQ ID NO: 1
MANMNSDSRHLGTSEVDHERDPGPMNIQFEPSDLRSKRPFCIEPTNIVNVNHVIQRV

SDHASAMNKRIHYYSRLITPADKALIAPDHVVPAPEECYVYSPLGSAYKLQSYTEGY

GKNTSLVTIFMIWNTMMGTSILSIPWGIKQAGFTTGMCVIILMGLLTLYCCYRVVKS

RTMMFSLDTTSWEYPDVCRHYFGSFGQWSSLLFSLVSLIGAMIVYWVLMSNFLFNIG

KFIFNFIHHINDTDTILSTNNSNPVICPSAGSGGHPDNSSMIFYANDTGAQQFEKWW

DKSRTVPFYLVGLLLPLLNFKSPSFFSKFNILGTVSVLYLIFLVTFKAVRLGFHLEF

HWFIPTEFFVPEIRFQFPQLTGVLTLAFFIHNCIITLLKNNKKQENNVRDLCIAYML

VTLTYLYIGVLVFASFPSPPLSKDCIEQNFLDNFPSSDTLSFIARIFLLFQMMTVYP

LLGYLARVQLLGHIFGDIYPSIFHVLILNLIIVGAGVIMACFYPNIGGIIRYSGAAC

GLAFVFIYPSLIYIISLHQEERLTWPKLIFHVFIIILGVANLIVQFFM

>gi|23273813|gb|AAH36301.1|TMEM192 protein [Homo sapiens]
                                              SEQ ID NO: 2
MAAGGRMEDGSLDITQSIEDDPLLDAQLLPHHSLQAHFRPRFHPLPTVIIVNLLWFI

HLVFVVLAFLTGVLCSYPNPNEDKCPGNYTNPLKVQTVIILGKVILWILHLLLECYI

QYHHSKIRNRGYNLIYRSTRHLKRLALMIQSSGNTVLLLILCMQHSFPEPGRLYLDL

ILAILALELICSLICLLIYTVKIRRFNKAKPEPDILEEEKIYAYPSNITSETGFRTI

SSLEEIVEKQGDTIEYLKRHNALLSKRLLALTSSDLGCQPSRT

>gi|74752435|sp|Q9BXP2.1|S12A9_HUMAN Solute carrier
family 12 member 9;
                                              SEQ ID NO: 3
MASESSPLLAYRLLGEEGVALPANGAGGPGGASARKLSTFLGVVVPIVLSMFSIVVF

LRIGFVVGHAGLLQALAMLLVAYFILALTVLSVCAIATNGAVQGGGAYFMISRTLGP

EVGGSIGLMFYLANVCGCAVSLLGLVESVLDVFGADATGPSGLRVLPQGYGWNLLYG

SLLLGLVGGVCTLGAGLYARASFLTFLLVSGSLASVLISFVAVGPRDIRLTPRPGPN

GSSLPPRFGHFTGFNSSTLKDNLGAGYAEDYTTGAVMNFASVFAVLFNGCTGIMAGA

NMSGELKDPSRAIPLGTIVAVAYTFFVYVLLFFLSSFTCDRTLLQEDYGFFRAISLW

PPLVLIGIYATALSASMSSLIGASRILHALARDDLFGVILAPAKVVSRGGNPWAAVL

YSWGLVQLVLLAGKLNTLAAVVTVFYLVAYAAVDLSCLSLEWASAPNFRPTFSLFSW

HTCLLGVASCLLMMFLISPGAAGGSLLLMGLLAALLTARGGPSSWGYVSQALLFHQV

RKYLLRLDVRKDHVKFWRPQLLLLVGNPRGALPLLRLANQLKKGGLYVLGHVTLGDL

DSLPSDPVQPQYGAWLSLVDRAQVKAFVDLTLSPSVRQGAQHLLRISGLGGMKPNTL

VLGFYDDAPPQDHFLTDPAFSEPADSTREGSSPALSTLFPPPRAPGSPRALNPQDYV

ATVADALKMNKNVVLARASGALPPERLSRGSGGISQLHHVDVWPLNLLRPRGGPGYV

DVCGLFLLQMATILGMVPAWHSARLRIFLCLGPREAPGAAEGRLRALLSQLRIRAEV

QEVVWGEGAGAGEPEAEEEGDFVNSGRGDAEAEALARSANALVRAQQGRGTGGGPGG
```

-continued

PEGGDAEGPITALTFLYLPRPPADPARYPRYLALLETLTRDLGPTLLVHGVTPVTCT

DL

>gi|12644301|sp|P51798.2|CLCN7_HUMAN Full = H(+)/Cl(-)
exchange transporter 7; AltName: Full = Chloride channel
7 alpha subunit; AltName: Full-Chloride channel protein
7; Short = ClC-7

SEQ ID NO: 4

MANVSKKVSWSGRDRDDEEAAPLLRRTARPGGGTPLLNGAGPGAARQSPRSALFRVG

HMSSVELDDELLDPDMDPPHPFPKEIPHNEKLLSLKYESLDYDNSENQLFLEEERRI

NHTAFRTVEIKRWVICALIGILTGLVACFIDIVVENLAGLKYRVIKGNIDKFTEKGG

LSFSLLLWATLNAAFVLVGSVIVAFIEPVAAGSGIPQIKCFLNGVKIPHVVRLKTLV

IKVSGVILSVVGGLAVGKEGPMIHSGSVIAAGISQGRSTSLKRDFKIFEYFRRDTEK

RDFVSAGAAAGVSAAFGAPVGGVLFSLEEGASFWNQFLTWRIFFASMISTFTLNFVL

SIYHGNMWDLSSPGLINFGRFDSEKMAYTIHEIPVFIAMGVVGGVLGAVFNALNYWL

TMFRIRYIHRPCLQVIEAVLVAAVTATVAFVLIYSSRDCQPLQGGSMSYPLQLFCAD

GEYNSMAAAFFNTPEKSVVSLFHDPPGSYNPLTLGLFTLVYFFLACWTYGLTVSAGV

FIPSLLIGAAWGRLFGISLSYLTGAAIWADPGKYALMGAAAQLGGIVRMTLSLTVIM

MEATSNVTYGFPIMLVLMTAKIVGDVFIEGLYDMHIQLQSVPFLHWEAPVTSHSLTA

REVMSTPVTCLRRREKVGVIVDVLSDTASNHNGFPVVEHADDTQPARLQGLILRSQL

IVLLKHKVFVERSNLGLVQRRLRLKDFRDAYPRFPPIQSIHVSQDERECTMDLSEFM

NPSPYTVPQEASLPRVFKLFRALGLRHLVVVDNRNQVVGLVTRKDLARYRLGKRGLE

ELSLAQT

SEQ ID NO: 5
QHKLRKLNPPDESGPGCMSCKCVLS

SEQ ID NO: 6
GCCTTGACAACAGTTCTATAT

SEQ ID NO: 7
CCTCTACTGTTTGGGACAGTA

SEQ ID NO: 8
TGCCCGACAACCACTACCTGA

SEQ ID NO: 9
GGGGCCACTAGGGACAGGAT

SEQ ID NO: 10
GGCTCAAACTGGATATTCATAGG

SEQ ID NO: 11
GGAGCTGGAACTACATGGTCTGG

SEQ ID NO: 12
EHNNALRYRL--YNRLD-PGGEHLTMPDHVLPPN

---

What is claimed is:

1. A method of identifying a test compound as a modulator of the interaction between SLC38A9 and a component of Ragulator or a RagGTPase comprising the steps of:
   a. contacting the test compound; the component of Ragulator or a RagGTPase; and a polypeptide comprising the polypeptide of SEQ ID NO: 1, a fragment of SEQ ID NO: 1 comprising at least amino acids 1-119 thereof, or a polypeptide variant having at least 90% sequence identity to either of the foregoing, wherein the variant comprises amino acids I68, Y71, L74, P85, and P90 of SEQ ID NO: 1;
   b. measuring the extent to which the component of Ragulator or a RagGTPase binds to the polypeptide of SEQ ID NO: 1, the fragment of SEQ ID NO: 1, or the polypeptide variant; and
   c. comparing the binding determined in step b to the binding of Ragulator or a RagGTPase to the polypeptide of SEQ ID NO: 1, the fragment of SEQ ID NO: 1, or the polypeptide variant under the same conditions as step a and in the absence of the test compound, thereby determining if the test compound is modulates the interaction between SLC38A9 and the component of Ragulator or a RagGTPase.

2. The method of claim 1, wherein the polypeptide comprising the polypeptide of SEQ ID NO: 1, the fragment of SEQ ID NO: 1, or the polypeptide variant further comprises a heterologous fusion partner.

3. The method of claim 2, wherein the heterologous fusion partner is selected from a N-terminal His tag, a N-terminal poly-His tag, an epitope tag, a ligand tag, a N- or C-terminal plasma membrane signal sequence, a fluorescent polypeptide, or a luminescent polypeptide.

4. A method of identifying a test compound as a modulator of the interaction between SLC38A9 and an amino acid comprising the steps of:

a. contacting the test compound; the amino acid; and a polypeptide comprising the polypeptide of SEQ ID NO: 1, a fragment of SEQ ID NO: 1 comprising at least amino acids 111-564 thereof, or a polypeptide variant having at least 90% sequence identity to either of the foregoing;

b. measuring the extent to which the amino acid binds to the polypeptide of SEQ ID NO: 1, the fragment of SEQ ID NO: 1, or the polypeptide variant; and c. comparing the binding determined in step b to the binding of the amino acid to the polypeptide of SEQ ID NO: 1, the fragment of SEQ ID NO: 1, or the polypeptide variant under the same conditions as step a and in the absence of the test compound, thereby determining if the test compound modulates the interaction between SLC38A9 and the amino acid.

5. The method of claim 4, wherein the polypeptide comprising the polypeptide of SEQ ID NO: 1, the fragment of SEQ ID NO: 1, or the polypeptide variant further comprises a heterologous fusion partner.

6. The method of claim 5, wherein the heterologous fusion partner is selected from a N-terminal His tag, a N-terminal poly-His tag, an epitope tag, a ligand tag, a N- or C-terminal plasma membrane signal sequence, a fluorescent polypeptide, or a luminescent polypeptide.

* * * * *